United States Patent
Katzman et al.

(10) Patent No.: US 11,309,077 B2
(45) Date of Patent: Apr. 19, 2022

(54) DISTRIBUTED PROCESSING OF SCAN DATA FOR FABRICATING DENTAL ALIGNERS

(71) Applicant: SmileDirectClub LLC, Nashville, TN (US)

(72) Inventors: Jordan Katzman, Nashville, TN (US); Alex Fenkell, Nashville, TN (US); David Katzman, Nashville, TN (US); Christopher Yancey, Nashville, TN (US); Josh Chapman, Nashville, TN (US); Jessica Cicurel, Nashville, TN (US)

(73) Assignee: SmileDirectClub LLC, Nashville, TN (US)

( * ) Notice: Subject to any disclaimer, the term of this patent is extended or adjusted under 35 U.S.C. 154(b) by 0 days.

(21) Appl. No.: 17/248,103

(22) Filed: Jan. 8, 2021

(65) Prior Publication Data

US 2021/0134450 A1    May 6, 2021

Related U.S. Application Data

(63) Continuation of application No. 17/247,296, filed on Dec. 7, 2020, now Pat. No. 11,094,414, which is a
(Continued)

(51) Int. Cl.
*G16H 40/20* (2018.01)
*A61C 7/00* (2006.01)
(Continued)

(52) U.S. Cl.
CPC ............ *G16H 40/20* (2018.01); *A61C 7/002* (2013.01); *A61C 7/08* (2013.01); *G06Q 10/02* (2013.01);
(Continued)

(58) Field of Classification Search
CPC ........ G16H 40/20; G16H 10/60; G16H 20/40; G16H 80/00; G06Q 10/02; G06Q 10/1095;
(Continued)

(56) References Cited

U.S. PATENT DOCUMENTS

| 4,002,162 A | 1/1977 | Weisser |
| 4,003,132 A | 1/1977 | Beck |

(Continued)

FOREIGN PATENT DOCUMENTS

| AU | 2015100268 | 5/2015 |
| BE | 1016074 | 2/2006 |

(Continued)

OTHER PUBLICATIONS

"Startup Story and Hiring Help from SmileDirect Club Founder Doug Hudson" on relode.com, published Aug. 11, 2015, available at https://www.relode.com/blog/startup-story-and-hiring-help-from-smilecareclub-founder-doug-hudson/ (Year: 2015).*

(Continued)

*Primary Examiner* — Mark Holcomb
(74) *Attorney, Agent, or Firm* — Foley & Lardner LLP

(57) ABSTRACT

Systems and methods directed to technological improvements in coordinated and distributed processing of intraoral scan data for fabricating clear aligners for dental realignment include an appointment management system that schedules an appointment at an intraoral scanning site and generates and causes transmission of a message to a computing device of a user. An intraoral scan that generates three-dimensional data of a mouth of the user is conducted at the intraoral scanning site using an intraoral scanner. Clear aligners that are specific to the user for repositioning the user's teeth are fabricated based on a treatment plan generated based on the three-dimensional data by thermoforming
(Continued)

material over three-dimensional printed molds. The clear aligners are sent to the user all at once. The user receives orthodontic treatment without ever having physically seen a dentist or an orthodontist that approves the treatment plan.

28 Claims, 58 Drawing Sheets

Related U.S. Application Data continuation of application No. 16/859,950, filed on Apr. 27, 2020, now Pat. No. 10,861,599, which is a continuation of application No. 16/130,762, filed on Sep. 13, 2018, now Pat. No. 10,636,522, which is a continuation-in-part of application No. 15/725,430, filed on Oct. 5, 2017.

(60) Provisional application No. 62/660,141, filed on Apr. 19, 2018, provisional application No. 62/522,847, filed on Jun. 21, 2017.

(51) Int. Cl.
*A61C 7/08* (2006.01)
*G06Q 10/02* (2012.01)
*G16H 10/60* (2018.01)
*G16H 20/40* (2018.01)
*G06Q 10/10* (2012.01)
*G16H 80/00* (2018.01)
*A61B 6/14* (2006.01)
*A61C 9/00* (2006.01)

(52) U.S. Cl.
CPC ......... *G06Q 10/1095* (2013.01); *G16H 10/60* (2018.01); *G16H 20/40* (2018.01); *A61B 6/145* (2013.01); *A61C 9/0053* (2013.01); *G16H 80/00* (2018.01)

(58) Field of Classification Search
CPC ........... A61B 6/145; A61C 7/002; A61C 7/08; A61C 9/0053
USPC ........................................................ 705/2–4
See application file for complete search history.

(56) References Cited

U.S. PATENT DOCUMENTS

| | | | |
|---|---|---|---|
| 4,200,089 A | 4/1980 | Inoue | |
| 4,763,791 A | 8/1988 | Halverson et al. | |
| 5,093,901 A | 3/1992 | Cree et al. | |
| 5,190,168 A | 3/1993 | French et al. | |
| 5,385,155 A | 1/1995 | Kittelsen et al. | |
| 5,816,255 A | 10/1998 | Fishman et al. | |
| 5,882,192 A | 3/1999 | Bergersen | |
| 5,975,893 A | 11/1999 | Chishti et al. | |
| 6,121,565 A | 9/2000 | Allott, III | |
| 6,227,851 B1 | 5/2001 | Chishti et al. | |
| 6,394,801 B2 | 5/2002 | Chishti et al. | |
| 6,450,807 B1 | 9/2002 | Chishti et al. | |
| 6,488,499 B1 | 12/2002 | Miller | |
| 6,582,225 B1 | 6/2003 | Bergersen | |
| 6,632,089 B2 | 10/2003 | Rubbert et al. | |
| 6,699,037 B2 | 3/2004 | Chishti et al. | |
| 6,732,103 B1 | 5/2004 | Strick et al. | |
| 6,761,560 B2 | 7/2004 | Miller | |
| 7,037,108 B2 | 5/2006 | Chishti et al. | |
| 7,077,647 B2 | 7/2006 | Choi et al. | |
| 7,156,661 B2 | 1/2007 | Choi et al. | |
| 7,188,073 B1 | 3/2007 | Tam et al. | |
| 7,192,275 B2 | 3/2007 | Miller | |
| 7,225,170 B1 | 5/2007 | Ryan, Jr. | |
| 7,383,198 B1 | 6/2008 | Sepe | |
| 7,467,022 B2 | 12/2008 | Bhagwat et al. | |
| 7,523,044 B2* | 4/2009 | Rosenblood | G06Q 30/02 705/2 |
| 7,578,674 B2 | 8/2009 | Chishti et al. | |
| 7,597,245 B1 | 10/2009 | Tillery | |
| 7,716,062 B2 | 5/2010 | Bergersen | |
| 7,738,989 B2 | 6/2010 | Taub et al. | |
| 7,904,307 B2 | 3/2011 | Abolfathi et al. | |
| 7,916,900 B2 | 3/2011 | Lanier | |
| 7,967,145 B2 | 6/2011 | Tchouangang | |
| 8,015,049 B1 | 9/2011 | Tam et al. | |
| 8,075,306 B2 | 12/2011 | Kitching et al. | |
| 8,087,932 B2 | 1/2012 | Liu | |
| 8,092,215 B2 | 1/2012 | Stone-Collonge et al. | |
| 8,145,340 B2 | 3/2012 | Taub et al. | |
| 8,287,275 B2 | 10/2012 | Knutson | |
| 8,303,301 B2 | 11/2012 | Bergersen | |
| 8,562,338 B2 | 10/2013 | Kitching et al. | |
| 8,577,493 B2 | 11/2013 | Taub et al. | |
| 8,591,225 B2 | 11/2013 | Wu et al. | |
| 8,636,510 B2 | 1/2014 | Kitching et al. | |
| 8,651,859 B2 | 2/2014 | Chishti et al. | |
| 8,731,280 B2 | 5/2014 | Kuo et al. | |
| 8,740,614 B2 | 6/2014 | Wen et al. | |
| 8,765,031 B2 | 7/2014 | Li et al. | |
| 8,899,978 B2 | 12/2014 | Kitching et al. | |
| 9,017,072 B2 | 4/2015 | Kitching et al. | |
| 9,107,722 B2 | 8/2015 | Matov et al. | |
| 9,168,113 B2 | 10/2015 | Wu et al. | |
| 9,256,962 B2 | 2/2016 | Berry et al. | |
| 9,364,297 B2 | 6/2016 | Kitching et al. | |
| D764,061 S | 8/2016 | Furdui-Carr | |
| 9,655,693 B2 | 5/2017 | Li et al. | |
| 9,715,753 B2 | 7/2017 | Berry et al. | |
| 9,757,065 B1 | 9/2017 | Suri et al. | |
| 9,855,123 B2 | 1/2018 | Wolgin | |
| 9,922,170 B2 | 3/2018 | Trosien et al. | |
| 10,052,174 B2 | 8/2018 | Kitching et al. | |
| 10,085,823 B2 | 10/2018 | Cao et al. | |
| 10,136,972 B2 | 11/2018 | Sabina et al. | |
| 10,231,801 B2 | 3/2019 | Korytov et al. | |
| 10,342,638 B2 | 7/2019 | Kitching et al. | |
| 10,383,705 B2 | 8/2019 | Shanjani et al. | |
| 10,504,386 B2 | 12/2019 | Levin et al. | |
| 10,595,966 B2 | 3/2020 | Carrier et al. | |
| 10,636,105 B2 | 4/2020 | Pumphrey | |
| 2001/0027481 A1 | 10/2001 | Whyel | |
| 2002/0007290 A1 | 1/2002 | Gottlieb | |
| 2002/0014357 A1 | 2/2002 | Hammonds | |
| 2002/0028418 A1 | 3/2002 | Farag et al. | |
| 2002/0029161 A1 | 3/2002 | Brodersen et al. | |
| 2002/0116232 A1 | 8/2002 | Rapp et al. | |
| 2002/0131565 A1 | 9/2002 | Scheuring et al. | |
| 2002/0143574 A1 | 10/2002 | Karras et al. | |
| 2002/0188478 A1* | 12/2002 | Breeland | G16H 10/60 705/3 |
| 2003/0138752 A1 | 7/2003 | Bergersen | |
| 2003/0207227 A1 | 11/2003 | Abolfathi | |
| 2003/0225594 A1 | 12/2003 | Bergersen | |
| 2004/0073611 A1 | 4/2004 | Atwood | |
| 2004/0091835 A1 | 5/2004 | Roetzer | |
| 2004/0152036 A1 | 8/2004 | Abolfathi | |
| 2004/0185415 A1 | 9/2004 | Ghim | |
| 2004/0197728 A1 | 10/2004 | Abolfathi et al. | |
| 2004/0250359 A1 | 12/2004 | Spivey | |
| 2005/0159986 A1 | 7/2005 | Breeland et al. | |
| 2005/0182654 A1 | 8/2005 | Abolfathi et al. | |
| 2006/0019216 A1 | 1/2006 | Priluck et al. | |
| 2006/0026051 A1 | 2/2006 | Rose | |
| 2006/0040230 A1 | 2/2006 | Blanding et al. | |
| 2006/0057541 A1 | 3/2006 | Kahwaty | |
| 2006/0064329 A1 | 3/2006 | Abolfathi et al. | |
| 2006/0093982 A1 | 5/2006 | Wen | |
| 2006/0141416 A1 | 6/2006 | Knutson | |
| 2006/0154198 A1 | 7/2006 | Durbin et al. | |
| 2006/0167724 A1 | 7/2006 | Petersen et al. | |
| 2006/0173708 A1 | 8/2006 | Vining et al. | |
| 2006/0275731 A1 | 12/2006 | Wen et al. | |
| 2006/0275736 A1 | 12/2006 | Wen et al. | |

(56) References Cited

U.S. PATENT DOCUMENTS

| | | |
|---|---|---|
| 2007/0005406 A1 | 1/2007 | Assadian et al. |
| 2007/0036320 A1 | 2/2007 | Mandalia et al. |
| 2007/0037116 A1 | 2/2007 | Knutson |
| 2007/0061166 A1 | 3/2007 | Ramasubramanian et al. |
| 2007/0102946 A1 | 5/2007 | Blackwell et al. |
| 2007/0128574 A1 | 6/2007 | Kuo et al. |
| 2007/0134613 A1 | 6/2007 | Kuo et al. |
| 2007/0238065 A1 | 10/2007 | Sherwood et al. |
| 2008/0059227 A1 | 3/2008 | Clapp |
| 2008/0159798 A1 | 7/2008 | Culp et al. |
| 2008/0206705 A1 | 8/2008 | Kaza et al. |
| 2008/0305454 A1 | 12/2008 | Kitching et al. |
| 2008/0306724 A1 | 12/2008 | Kitching et al. |
| 2008/0308450 A1 | 12/2008 | Tchouangang |
| 2009/0061381 A1 | 3/2009 | Durbin et al. |
| 2009/0081604 A1* | 3/2009 | Fisher ............... A61C 9/0006 433/24 |
| 2009/0081611 A1 | 3/2009 | Hines et al. |
| 2009/0136893 A1 | 5/2009 | Zegarelli |
| 2009/0215003 A1 | 8/2009 | Swain et al. |
| 2010/0036682 A1 | 2/2010 | Trosien et al. |
| 2010/0068676 A1 | 3/2010 | Mason et al. |
| 2010/0070297 A1 | 3/2010 | Kharraz Tavakol et al. |
| 2010/0082391 A1 | 4/2010 | Soerensen et al. |
| 2010/0105011 A1 | 4/2010 | Karkar et al. |
| 2010/0145754 A1 | 6/2010 | Rahman |
| 2010/0153162 A1 | 6/2010 | Tam et al. |
| 2010/0179854 A1 | 7/2010 | Shafer et al. |
| 2010/0203466 A1 | 8/2010 | Lawrence |
| 2011/0084093 A1 | 4/2011 | Nehren et al. |
| 2011/0106557 A1 | 5/2011 | Gazula |
| 2011/0161249 A1 | 6/2011 | Whitehouse |
| 2011/0183293 A1 | 7/2011 | Tchouangang |
| 2011/0215933 A1 | 9/2011 | Darling et al. |
| 2012/0065985 A1 | 3/2012 | Royal et al. |
| 2012/0083549 A1 | 4/2012 | Kamohara et al. |
| 2012/0267811 A1 | 10/2012 | Weitzman |
| 2012/0330677 A1 | 12/2012 | Velimesis |
| 2013/0028617 A1 | 1/2013 | Fukuoka et al. |
| 2013/0035955 A1 | 2/2013 | Torres |
| 2013/0087157 A1 | 4/2013 | Hawkins et al. |
| 2013/0089828 A1 | 4/2013 | Borovinskih et al. |
| 2013/0122448 A1 | 5/2013 | Kitching |
| 2013/0215116 A1 | 8/2013 | Siddique et al. |
| 2013/0230300 A1 | 9/2013 | Saleh et al. |
| 2013/0286174 A1 | 10/2013 | Urakabe |
| 2014/0052661 A1 | 2/2014 | Shakes et al. |
| 2014/0122100 A1 | 5/2014 | Fillmore |
| 2014/0199653 A1 | 7/2014 | Kurthy |
| 2014/0249878 A1 | 9/2014 | Kaufman |
| 2014/0278679 A1 | 9/2014 | Navani et al. |
| 2014/0315153 A1 | 10/2014 | Kitching et al. |
| 2014/0330577 A1* | 11/2014 | Herman ............... G16H 20/10 705/2 |
| 2014/0356798 A1 | 12/2014 | Parker |
| 2014/0379356 A1 | 12/2014 | Sachdeva et al. |
| 2015/0010879 A1 | 1/2015 | Kurthy |
| 2015/0202025 A1 | 7/2015 | Kaza et al. |
| 2015/0205921 A1 | 7/2015 | Dick et al. |
| 2015/0220887 A1 | 8/2015 | Peres et al. |
| 2015/0238283 A1 | 8/2015 | Tanugula et al. |
| 2015/0257859 A1 | 9/2015 | Akl |
| 2015/0310387 A1 | 10/2015 | Friedman et al. |
| 2016/0012182 A1 | 1/2016 | Golay |
| 2016/0034871 A1 | 2/2016 | Vargas et al. |
| 2016/0132893 A1 | 5/2016 | Bisges et al. |
| 2016/0158627 A1 | 6/2016 | Layzell |
| 2016/0242871 A1 | 8/2016 | Morton et al. |
| 2016/0253464 A1* | 9/2016 | Balwani ............... G06Q 10/00 705/2 |
| 2016/0256240 A1 | 9/2016 | Shivapuja et al. |
| 2016/0263732 A1 | 9/2016 | Lourenco et al. |
| 2016/0287198 A1 | 10/2016 | Abramovich et al. |
| 2016/0317264 A1 | 11/2016 | Derraugh et al. |
| 2017/0010252 A1 | 1/2017 | Bearup et al. |
| 2017/0020642 A1 | 1/2017 | Mah |
| 2017/0039423 A1 | 2/2017 | Cork et al. |
| 2017/0046486 A1 | 2/2017 | Cunningham |
| 2017/0156830 A1 | 6/2017 | Wallace |
| 2017/0165040 A1 | 6/2017 | Wolgin |
| 2017/0231721 A1 | 8/2017 | Akeel et al. |
| 2017/0239018 A1 | 8/2017 | Kim |
| 2017/0281313 A1 | 10/2017 | Kim |
| 2017/0300207 A1 | 10/2017 | Wen et al. |
| 2017/0340414 A1 | 11/2017 | Janzadeh et al. |
| 2017/0347953 A1 | 12/2017 | Suri et al. |
| 2017/0364637 A1 | 12/2017 | Kshepakaran et al. |
| 2017/0365025 A1 | 12/2017 | Pumphrey |
| 2018/0014914 A1 | 1/2018 | Raghavan et al. |
| 2018/0110589 A1* | 4/2018 | Gao ..................... A61C 7/002 |
| 2018/0121875 A1 | 5/2018 | Satyanarayana Rao et al. |
| 2018/0125610 A1 | 5/2018 | Carrier et al. |
| 2018/0206940 A1* | 7/2018 | Kopelman ............ A61C 7/002 |
| 2018/0228359 A1 | 8/2018 | Meyer et al. |
| 2018/0263731 A1 | 9/2018 | Pokotilov et al. |
| 2018/0263733 A1 | 9/2018 | Pokotilov et al. |
| 2018/0285801 A1 | 10/2018 | Alde et al. |
| 2018/0303580 A1 | 10/2018 | Salah et al. |
| 2018/0353073 A1 | 12/2018 | Boucher et al. |
| 2018/0368943 A1 | 12/2018 | Katzman et al. |
| 2018/0368953 A1 | 12/2018 | Katzman et al. |
| 2018/0368954 A1 | 12/2018 | Katzman et al. |
| 2019/0013098 A1 | 1/2019 | Katzman et al. |
| 2019/0019187 A1 | 1/2019 | Miller et al. |
| 2019/0026598 A1 | 1/2019 | Salah et al. |
| 2019/0038383 A1 | 2/2019 | Webber et al. |
| 2019/0083219 A1 | 3/2019 | Sharer |
| 2019/0175303 A1 | 6/2019 | Akopov et al. |
| 2019/0223983 A1 | 7/2019 | Mah |
| 2019/0252066 A1 | 8/2019 | Katzman et al. |
| 2019/0333622 A1 | 10/2019 | Levin et al. |
| 2019/0388188 A1 | 12/2019 | Kaza et al. |
| 2020/0035353 A1 | 1/2020 | Katzman et al. |
| 2020/0066391 A1 | 2/2020 | Sachdeva et al. |
| 2020/0081413 A1 | 3/2020 | Georg et al. |
| 2020/0113650 A1 | 4/2020 | Lemchen et al. |
| 2020/0289238 A1 | 9/2020 | Levine |
| 2020/0306011 A1 | 10/2020 | Chekhonin et al. |
| 2020/0401976 A1 | 12/2020 | Nelson et al. |
| 2021/0196434 A1 | 7/2021 | Cramer et al. |

FOREIGN PATENT DOCUMENTS

| | | |
|---|---|---|
| CN | 201370648 | 12/2009 |
| CN | 204472650 | 7/2015 |
| CN | 106326681 | 1/2017 |
| EP | 0 278 626 | 8/1988 |
| EP | 2 425 734 | 3/2012 |
| EP | 3 595 572 | 1/2020 |
| GB | 0 338 822 | 11/1930 |
| JP | 09-038117 | 2/1997 |
| WO | WO-2006/118771 | 11/2006 |
| WO | WO-2009/085752 | 7/2009 |
| WO | WO-2015/054746 | 4/2015 |
| WO | WO-2019/036677 | 2/2019 |

OTHER PUBLICATIONS

Kravitz, Neal D., et al. "Teledentistry, do-it-yourself orthodontics, and remote treatment monitoring." Journal of clinical orthodontics: JCO 50.12 (2016): 718-726. (Year: 2016).*

From Home Dental website, published on Oct. 21, 2016, available at https://web.archive.org/web/20161021220200/https:/fromhomedental.com/ (Year: 2016).*

"203221—SmileCareClub" video, uploaded to YouTube on Jun. 10, 2014, https://www.youtube.com/watch?v=B43vT_1GnR0, 33 pages of screenshots.

"Affordable Clear Braces—Smile Care Club" video, uploaded to YouTube on Mar. 30, 2015, https://www.youtube.com/watch?v=Qk-VhbH1RVM, 97 pages of screenshots.

"Clear Braces . . . At HOME??! Review—Before & After—Cost" video, uploaded to YouTube on Oct. 7, 2014, https://www.youtube.

(56) References Cited

OTHER PUBLICATIONS com/watch?v=9wrwhRTPjtk&t, 132 pages of screenshots.
"Invisalign Manufacturing Process English" video, uploaded to YouTube on Apr. 7, 2014, https://www.youtube.com/watch?v=vsR0_wTR2a8, 125 pages of screenshots.
"Smile Care Club Unboxing, Review, Tutorial" video, uploaded to YouTube on May 1, 2015, https://www.youtube.com/watch?v=p7Y5fMRnJWE, 126 pages of screenshots.
"Smile Direct Club SmileShop Visit" video, uploaded to YouTube on Nov. 2, 2016, https://www.youtube.com/watch?v=wYQdNHPJb18, 420 pages of screenshots.
"Speak Out Game—Ellen Show with Khloe Kardashian and Kevin Hart", uploaded to YouTube on Oct. 11, 2016, https://www.youtube.com/watch?v=RDILAiBFRLY, 50 pages of screenshots.
"Startup Story and Hiring Help from Smile Direct Club Founder Doug Hudson" on relode.com, published Aug. 11, 2015, available at https://www.relode.com/blog/startup-story-and-hiring-help-from-smilecareclub-founder-doug-hudson, 2 pages.
"Step 1! Working on my Smile . . . Smile Care Club" video, uploaded to YouTube on Jan. 4, 2015, https://www.youtube.com/watch?v=T_F3Xt4Og7w, 87 pages of screenshots.
Albert et al., "Smile Care Club Review—My experience straightening my teeth with smile care", https://smilecareclubreview.wordpress.com/page/1/, relevant web posts published from Jan. 9-Mar. 4, 2015, accessed online Dec. 30, 2019 (Year: 2015), 8 pages.
Buschang et al., "Comparative Time Efficiency of Aligner Therapy and Conventional Edgewise Braces", Angle Orthodontist, vol. 84, No. 3, 2014, 6 pages.
Candid Care Co., https:/www.candidco.com/how-it-works/, webpage printed as existed on Sep. 2, 2018, located using the Internet Archive WayBack Machine, 10 pages.
Complaint for Patent Infringement, *SMILEDIRECTCLUB, LLC* v. *CANDID CARE CO.*, Case No. Case 1:20-cv-00583-UNA, Apr. 29, 2020, 45 pages.
Defendant Candid Care Co's Opening Brief in Support of its Motion to Dismiss, *SMILEDIRECTCLUB, LLC* v. *CANDID CARE CO.*, Case No. Case 1:20-cv-00583-CFC, Jun. 19, 2020, 147 pages.
Defendant Candid Care Co's Reply Brief in Support of its Motion to Dismiss, *SMILEDIRECTCLUB, LLC* v. *CANDID CARE CO.*, Jul. 31, 2020, 17 pages.
Do It Yourself Dental Impression Kit, Apr. 30, 2016, 2 pages.
Grindguard, "How to use your dental impression kit", http://www.grindguardpm.com/support/how-to-use-your-dental-impression-kit/ Feb. 9, 2017, accessed online Jan. 3, 2020 (Year: 2017), 5 pages.
Hoabie et al., "Evaluation Kit in Mail", https://smilecareclub.wordpress.com/ Mar. 27, 2015, accessed online Jan. 2, 2020 (Year: 2015), 3 pages.
International Search Report and Written Opinion for International Application No. PCT/US2018/038459, dated Oct. 22, 2018, 13 pages.
International Search Report and Written Opinion for International Application No. PCT/US2019/054958, dated Dec. 17, 2019, 8 pages.
International Search Report in International Patent Application PCT/US2018/065133 dated Apr. 22, 2019 (2 pages).
ITero Element Orthodontic Patient Video, Uploaded to YouTube Apr. 4, 2016, https://www.youtube.com/watch?v=Ca69CuWqHCw, 33 pages of screenshots.
Kravitz et al., "Teledentistry, Do-It-Yourself Orthodontics, and Remove Treatment Monitoring", JCO, Dec. 2016, 9 pages.
Memorandum Opinion, *SMILEDIRECTCLUB, LLC* v. *CANDID CARE CO.*, Case 1:20-cv-00583-CFC, Dec. 7, 2020, 25 pages.
Mouthpiece Guy et al.: "Mouthpiece Guy vs. The Competition: Impression Kits", www.youtube.com/watch?v=tYOjMtYWQOQ&feature=youtu.be, Feb. 23, 2018, 20 pages of screenshots.
Notice of Appeal, *SMILEDIRECTCLUB, LLC* v. *CANDID CARE CO.*, Case 1:20-cv-00583-CFC, Dec. 8, 2020, 2 pages.
Smile Care Club Review, URL: https://www.youtube.com/watch?v=jpAjhJqi6vc, Mar. 26, 2016, 260 pages of screenshots.

Smile Care Club, "Impression Kit", Jul. 21, 2014, available for retrieval at URL https://vimeo.com/wmvproductions/review/115725718/28854a7f49, 43 pages of screenshots.
Smile Care Club, "Impressions—New Box", 2015,available for retrieval at URL https://vimeo.com/wmvproductions/review/137176701/d45be82d56, 24 pages of screenshots.
Smile Care Club, "Impressions—Old Box", 2015,available for retrieval at URL https://vimeo.com/wmvproductions/review/137176599/0b8020929d, 21 pages of screenshots.
Smile Care Club, "Impressions ReEdit", 2016,available for retrieval at URL https://vimeo.com/wmvproductions/review/168249998/0b75310374, 32 pages of screenshots.
Smile Care Club, "Impressions", 2015,available for retrieval at URL https://vimeo.com/wmvproductions/review/136533463/1a8515abf5, 10 pages of screenshots.
Smile Care Club, "Making Dental Impressions" video, Mar. 2016, 74 pages of screenshots.
Smile Care Club, "Promo", 2014, available for retrieval at URL https://vimeo.com/wmvproductions/review/115725719/9c8235cdf2, 25 pages of screenshots.
Smile Direct Club "smile evaluation kit instruction guide" https://s3.amazonaws.com/static.smiledirectclub.com/evaluation_kit_instructions_5_2_16_email .pdf.
Smile Direct Club Impression Guide (available online Nov. 14, 2016, https://www.sharperimage.com/si/pdf/manuals/203221.pdf accessed Sep. 3, 2019 (Year: 2016), 24 pages.
Smile Direct Club Vimeo online video uploaded publicly on Mar. 2, 2016 (https://vimeo.com/157450883, pdf attachment of screen captures published online (Year: 2016) accessed and recorded on Dec. 13, 2018.
SmileCareClub promo video uploaded on Jun. 6, 2014 https://www.youtube.com/watch?v=h7x8BwWXUsk, 33 pages of screenshots.
Smiledirectclub, "What's a Smile Shop?", https://blog.smiledirectclub.com/what-is-smiledirectclub-smileshop/ Apr. 6, 2017, 7 pages.
SmileDirectClub, LLC's Opposition to Candid Care Co.'s Motion to Dismiss, *SMILEDIRECTCLUB, LLC* v. *CANDID CARE CO.*, Case No. Case 1:20-cv-00583-CFC, Jul. 17, 2020, 29 pages.
Summerfelt, Fred F., "Teledentisty-Assisted, Affiliated Practice for Dental Hygienists: An Innovative Oral Health Workforce Model", Journal of Dental Education, vol. 75, No. 6, Jun. 2011, pp. 733-742.
SwankySmiles advertisement from Feb. 8, 2019, located at www.swankysmiles.com, 5 pages of screenshots.
"Why I am Straightening My Teeth With SmileDirectClub", Gluesticks Blog, https://gluesticksblog.com/smiledirectclub-review/, Aug. 26, 2015, 19 pages.
Beers et al., "Computer-assisted treatment planning and analysis", Orthod Caniofacial Res 6(Suppl. 1), 2003; 117-125.
Bhambal et al., "Teledentistry: potentials unexplored!", J. Int Oral Health, Oct. 2010, vol. 2 (Issue 3).
Cooper et al.,"Knowledge, attitudes, and confidence levels of dental hygiene students regarding teledentistry: A pilot study." The Internet Journal of Allied Health Sciences and Practice. Oct. 2007, vol. 5 No. 4.
Ercoli et al., "A comparative study of two different clear aligner systems", Progress in Orthodontics, 2014.
Fabels et al., "Interexaminer and intraexaminer reliabilites of 3-dimensional orthodontic digital setups", American Journal of Orthodontics and Dentofacial Orthopedics, Dec. 2014, vol. 146, Issue 6.
Forever Aligned Club, "Straight Teeth Forever", https://www.foreveralignedclub.com/straight-teeth-forever/, May 26, 2017, 3 pages.
Garino et al., "The iTero Intraoral Scanner in Invisalign Treatment: A Two-year Report", JCO, Feb. 2014.
Groth et al., "Three-Dimensional Printing Technology", JCO, 2014.
Hayashi et al., "Assessment of the accuracy and reliability of new 3-dimensional scanning devices", American Journal of Orthodontics and Dentofacial Orthopedics, Oct. 2013, vol. 144, Issue 4.
Jain et al., "Teledentistry: Upcoming Trend in Dentistry", J Adv Med Dent Scie 2013; 1(2): 112-115.
James Hunt; SmileDirectClub impression kit, https://www.youtube.com/watch?v=3u2KI9Mphey, uploaded Jan. 16, 2017, 19 pages of screenshots.

(56) References Cited

OTHER PUBLICATIONS

Jampani et al., "Applications of teledentistry: A literature review and update", Journal of Int Society of Preventive & Community Dentistry, Jul.-Dec. 2011; 1(2): 37-44.
Jones, Perry "The iTero optical scanner for use with Invisalign: A descriptive review", ineedce.com, Feb. 2012.
Kravitz et al., "Intraoral Digital Scanners", JCO, 2014, vol. 48, No. 6.
Kuncio, Daniel A. "Invisalign: Current guidelines for Effective Treatment", NY State Dental Journal, Mar. 2014.
Lau et al., "Computerised Imaging, Virtual Treatment Planning and Orthodontic Treatment of Dental Malocclusions Using the Invisalign Appliance", The Hong Kong Medical Diary, vol. 9, No. 10, Oct. 2004.
Lin et al., "3D CAD tor Design or Invisible Tooth Aligner", Proceedings of the 2005 IEEE Int Conf on Mechanics, Jul. 10-12, Taipei, Taiwan.
Martin et al., "Orthodontic scanners: what's available?", Journal of Orthodontics, vol. 000, 2014, 000-000.
Martorelli et al., "A comparison between customized clear and removable orthodontic appliances manufactured using RP and CNC techniques", Elsevier, Dental Materials 29 (2013).
Monika et al., "Teledentistry: An Overview." J Adv Med Dent Scie Res 2015;3(2):88-91.
Shailee et al., "Teledentistry the future of dental practice", Indian J Dent Adv 2013; 5(2): 1195-1199.
Smiledirectclub; Frequent Questions https://web.archive.org/web/20170409175711/https://smiledirectclub.com/faq/ Apr. 9, 2017, 7 pages.
Snapcorrect, "What Does My Impression Evaluation Kit Include", https://support.snapcorrect.com/support/solutions/articles/32000019500-what-does-my-impression-evaluation-kit-include, Sep. 18, 2017 1 page.
Snapcorrect, "What Does the 'Return by' Sticker Date Mean", https://support.snapcorrect.com/support/solutions/articles/32000022084-what-does-the-return-by-sticker-date-mean, Feb. 5, 2018 1 page.
Snapcorrect, Snap Correct Impressions, https://www.youtube.com/watch?v=yywqIDSabew, uploaded Oct. 6, 2017, 6 pages of screenshots.
Snapcorrect, SnapCorrect Truly Invisible Aligners, https://youtube.com/watch?v=yywqIDSabew, uploaded Jul. 27, 2017, 8 pages of screenshots.
Summerfelt, Fred F."Teledentistry-Assisted, Affiliated Practice for Dental Hygienists: An Innovative Oral Health Workforce Model", Journal of Dental Education, 2011.
Szuhanek et al., "Application of Thermoplastic Materials in the Fabrication of Orthodontic Aligners", Materiale Plastice, 52, No. 3, 2015.
Szuhanek et al., "The Role of Digital Setup in the Orthodontic Treatment with Plastic Aligners", Materiale Plastice, 52, No. 4, 2015.
Taneva et al., "3D Scanning, Imaging, and Printing in Orthodontics", IntechOpen, 2015.
Thukral et al., "Invisalign: Invisible Orthodontic Treatment—A Review." J Adv Med Dent Scie Res 2015;3(5):S42-S44.
Align Technology, Inc., "Invisalign Outcome Simulator 4.1," 2017, https://www.rdentalab.com/resources/clinical-information-guides/ (50 pages).
Align Technology, Inc., "iTero Element 2 and Flex Brochure for Orthodontists," 2018, https://global.itero.com/en-gb/training/literature (6 pages).
Dental Review, "New Itero Element 2 and iTero Element Flex," 2018, https://www.dentalreview.news/technology/24-dental-cad-cam-technology / 3 25 5-new-itero-element-2-and-itero-element-flex (4 pages).
Federal Circuit Affirmance on the '522 patent Case No. 2021-1446 dated Aug. 17, 2021.
Decision on Appeal for U.S. Appl. No. 15/725,430, dated Sep. 23, 2021, 11 Pages.
CVS Health and Smile Direct Club Team Up to Expand Access and Affordability to Innovative Solution for Achieving A Straighter Smile (Apr. 25, 2019). PR Newswire Retrieved from https://dialog.proquest.com/professional/docview/2213815454?accountid=131444 (Year: 2019).

* cited by examiner

FREE SMILE ASSESSMENT

THE FOLLOWING QUESTIONS WILL HELP OUR DENTAL STAFF ASSESS IF COMPANY IS RIGHT FOR YOU.

① HAVE YOU WORN BRACES OR INVISIBLE ALIGNERS IN THE PAST?

| YES | NO |

② CHOOSE THE OPTION THAT BEST DESCRIBES YOUR BIGGEST CONCERN WITH YOUR SMILE:

FIX A SPACING ISSUE ▼

③ OF THE IMAGES BELOW, WHICH ONE BEST DESCRIBES YOUR TEETH CROWDING?

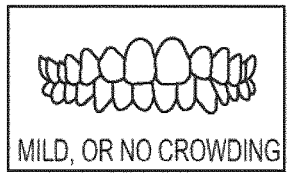 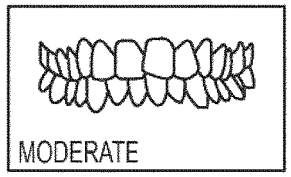 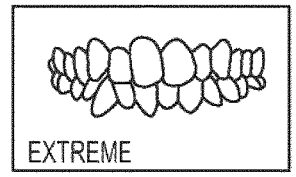

MILD, OR NO CROWDING | MODERATE | EXTREME

④ OF THE IMAGES BELOW, WHICH ONE BEST DESCRIBES YOUR TEETH SPACING?

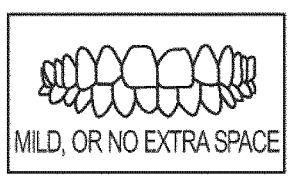 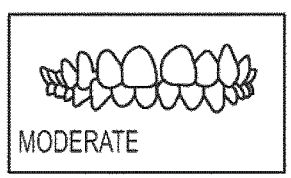 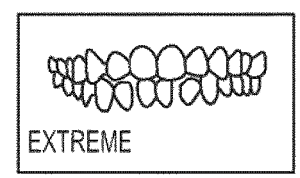

MILD, OR NO EXTRA SPACE | MODERATE | EXTREME

• • •

GET YOUR RESULTS

*FIG. 26*

MY ACCOUNT
WELCOME BACK, MAGGIE!

USER:

YOUR NEXT STEP:

WHERE'S YOUR CAMERA? WITHOUT PHOTOS OF YOUR TEETH YOUR SMILE IS IN LIMBO. WE CAN'T BUILD YOUR CUSTOM TREATMENT PLAN AND WE CAN'T MOVE FORWARD. GET THAT CAMERA AND LET'S GET THOSE PHOTOS UPLOADED. IF YOU'RE HAVING ISSUES UPLOADING YOUR PHOTOS YOU CAN EMAIL THEM TO SUPPORT@COMPANY.COM

YOU'RE SCHEDULED FOR AN APPOINTMENT AT THE DENTIST AT 11:00 AM CDT, TUESDAY, MARCH 14, 2017.

THANK YOU FOR BOOKING YOUR SCAN. WE ARE LOCATED AT ADDRESS.

HELPFUL HINTS:

- YOU CAN ALWAYS CALL US AT 555-555-5555 IF YOU NEED HELP WITH DIRECTIONS.
- MAKE SURE TO BRUSH YOUR TEETH BEFORE YOUR APPOINTMENT.
  - ARRIVE A LITTLE EARLY FOR PARKING
  - THE SMILESHOP IS LOCATED INSIDE THE BUILDING.

MAGGIE

[COMPLETE YOUR PHOTO ASSESSMENT] 1602

FEEL FREE TO CALL US AT 555-555-5555 FOR QUESTIONS REGARDING SCHEDULING.

*FIG. 27*

YOU'RE ON YOUR WAY TO A BETTER SMILE.

THE BELOW INFORMATION WILL HELP OUR DENTAL PROFESSIONALS EVALUATE YOUR SMILE AND CREATE YOUR CUSTOM TREATMENT PLAN.

I HAVE A BONDED RETAINER

| YES | NO |

I HAVE BRIDGEWORK

| YES | NO |

1800

1802

I HAVE CROWNS

| YES | NO |

I HAVE AN IMPACTED TOOTH

| YES | NO |

I HAVE AN IMPLANT

| YES | NO |

I HAVE PRIMARY (BABY) TEETH

| YES | NO |

I HAVE VENEERS

| YES | NO |

PRIMARY COMPLAINT

TELL US WHAT YOU WANT TO CHANGE ABOUT YOUR SMILE (EXAMPLE: "PLEASE FIX THE GAP IN MY FRONT TEETH," "PLEASE ROTATE MY BOTTOM RIGHT TOOTH," ETC.). OUR PROVIDERS NEED EXAMPLES OF WHAT YOU'D LIKE TO CHANGE IN ORDER TO PRESCRIBE TREATMENT. PLEASE BE AS SPECIFIC AS POSSIBLE.

WRITE YOUR COMMENTS HERE

SUBMIT

TREATMENT OPTIONS:

✓ ------
BOTH
UPPER
LOWER

| | | |
|---|---|---|
| I HAVE BRIDGEWORK: | ○ YES | ○ NO |
| I HAVE CROWNS: | ○ YES | ○ NO |
| I HAVE AN IMPACTED TOOTH: | ○ YES | ○ NO |
| I HAVE AN IMPLANT: | ○ YES | ○ NO |
| I HAVE PRIMARY (BABY) TEETH: | ○ YES | ○ NO |
| I HAVE VENEERS: | ○ YES | ○ NO |
| DO YOU FEEL PAIN IN ANY OF YOUR TEETH?: | ○ YES | ○ NO |
| DO YOU CURRENTLY HAVE ANY HEAD, NECK, OR JAW INJURIES?: | ○ YES | ○ NO |
| DO YOU HAVE ANY SORES OR LUMPS IN OR NEAR YOUR MOUTH?: | ○ YES | ○ NO |
| DO YOU CURRENTLY EXPERIENCE: JAW CLICKING, PAIN, DIFFICULTY OPENING AND/OR CLOSING OR DIFFICULTY CHEWING?: | ○ YES | ○ NO |
| HAVE YOU NOTICED ANY LOOSENING OF YOUR TEETH OR DO YOU HAVE UNTREATED PERIODONTAL DISEASE?: | ○ YES | ○ NO |

| | | |
|---|---|---|
| DO YOU HAVE ANY KNOWN ALLERGIES TO ANY DENTAL MATERIALS?: | ◯ YES | ◯ NO |
| I HAVE A HISTORY OF IV BISPHOSPHONATE TREATMENT.: | ◯ YES | ◯ NO |
| I AM CURRENTLY ON ACUTE CORTICOSTEROIDS OR IN IMMUNOSUPPRESSION, CHEMOTHERAPY, OR RADIATION OF HEAD/NECK.: | ◯ YES | ◯ NO |
| I HAVE HAD A BONE MARROW TRANSPLANT OR TREATMENT OF HEMATOLOGICAL MALIGNANCIES (BLOOD CANCERS) WITHIN THE PAST 2 YEARS.: | ◯ YES | ◯ NO |

CHIEF COMPLAINT:

[ SUBMIT ] [ CANCEL ]

| QUESTION | ANSWER |
| --- | --- |
| ALLOW REFERRAL | NONE |
| HAS BONDED RETAINER | NO |
| HAS BRIDGEWORK | NO |
| HAS CROWNS | NO |
| HAS IMPACTED TOOTH | NO |
| HAS IMPLANT | NO |
| HAS PRIMARY TOOTH | NO |
| HAS VENEERS | NO |

HISTORY

EDIT HISTORY

| JOURNAL | | |
|---|---|---|
| DATE | NOTE | AUDIENCE |
| MONDAY, MARCH 6, 2017 12:28 P.M. UTC | E-MAILED *** TO REVIEW THE TP BY: *@* | STAFF |
| FRIDAY, MARCH 3, 2017 12:28 P.M. UTC | FRENECTOMY CONSENT: EMAIL_VIEWED BY:ECHOSIGN | |
| FRIDAY, MARCH 3, 2017 12:28 P.M. UTC | FRENECTOMY CONSENT: EMAIL_VIEWED BY:ECHOSIGN | |
| THURSDAY, MARCH 2, 2017 10:15 P.M. UTC | STATUS CHANGED FROM SETUP IN PROGRESS TO SETUP READY FOR REVIEW BY: ***@* | |
| THURSDAY, MARCH 2, 2017 10:14 P.M. UTC | NATHAN CRUTCH NEW SMILE PLAN REVISION UPLOADED BY: ***@* | |
| THURSDAY, MARCH 2, 2017 4:07 P.M. UTC | TREATMENT PLAN REVISION REQUESTED BY: ****** | ALL |
| THURSDAY, MARCH 2, 2017 4:07 P.M. UTC | STATUS CHANGED FROM SETUP READY FOR REVIEW TO SETUP IN PROGRESS BY: ****** | |
| THURSDAY, MARCH 2, 2017 3:35 P.M. UTC | STATUS CHANGED FROM SECOND OPINION (TREATMENT PLAN REJECTED) TO SETUP READY FOR REVIEW BY: ***@* | |
| THURSDAY, MARCH 2, 2017 3:35 P.M. UTC | CASE SUBMITTED TO *** BY: *@* | |
| THURSDAY, MARCH 2, 2017 3:35 P.M. UTC | FRENECTOMY CONSENT: SIGNATURE_REQUESTED BY:ECHOSIGN | |
| THURSDAY, MARCH 2, 2017 3:35 P.M. UTC | FRENECTOMY CONSENT: CREATED BY:ECHOSIGN | |
| THURSDAY, MARCH 2, 2017 2:36 P.M. UTC | TREATMENT PLAN REJECTED BY: ***** | ALL |
| THURSDAY, MARCH 2, 2017 2:36 P.M. UTC | STATUS CHANGED FROM SETUP READY FOR REVIEW TO SECOND OPINION (TREATMENT PLAN REJECTED) BY: ***** | |
| THURSDAY, MARCH 2, 2017 12:31 P.M. UTC | HYGIENIST RECOMMENDATION:APPROVE (WAITING ON OFFICAL RESPONSE FROM DOCTOR) BY:***@* | ALL |
| THURSDAY, MARCH 2, 2017 2:45 A.M. UTC | STATUS CHANGED FROM SETUP IN PROGRESS TO SETUP READY FOR REVIEW BY: ***@* | |

ALL CASE MESSAGES

TREATMENT PLAN REVISION 1
CREATED BY ****** ON 03-12-17 2:45AM

FROM: ******
TO: PROV
DATE: 03-02-17 10:15PM

LAB ID: CA734723
CASE: CFA5D9990BD4D2
PATIENT: ******
MRN: M269FA0A8B9A23

YOUR REVISION REQUEST HAS BEEN COMPLETED, PLEASE REVIEW THE NEW TREATMENT PLAN.

NASHVILLE, TN 37219

[REPLY]

TREATMENT PLAN REVISION 1
CREATED BY ****** ON 03-12-17 2:45AM

FROM: ******
TO: SUPPORT
DATE: 03-02-17 2:36PM

LAB ID: CA734723
CASE: CFA5D9990BD4D2
PATIENT: ******
MRN: M269FA0A8B9A23

TREATMENT PLAN REJECTED.
PERIODONTAL CLEARANCE
NEED PERIO CLEARANCE MUST HAVE CLEANING PRIOR TO ALIGNER TREATMENT

NASHVILLE, TN 37219

[REPLY]

FROM: ******
TO: SUPPORT
DATE: 03-02-17 2:36PM

LAB ID: CA734723
CASE: CFA5D9990BD4D2
PATIENT: ******
MRN: M269FA0A8B9A23

NEED PERIO CLEARANCE MUST HAVE CLEANING PRIOR TO ALIGNER TREATMENT.

[REPLY]

FROM: ******
TO: PROV
DATE: 03-02-17 2:41PM

PLEASE NOTICE THAT SPACE WAS LEFT DISTAL FROM UPPER LATERALS, IN ORDER TO AVOID AFFECTING CANINE RELATIONSHIP.

*FIG. 34E*

| FILES | | | |
|---|---|---|---|
| NAME | KIND | UPLOAD DATE | UPLOADED BY |
| NEW SMILE PLAN REVISION | TREATMENTPLAN | 03-02-2017 10:14PM(UTC) | ********** |
| NEW SMILE PLAN | TREATMENTPLAN | 03-02-2017 2:44AM(UTC) | ************ |
| LOWER | 3DSCAN | 03-01-2017 2:16AM(UTC) | ********** |
| UPPER | 3DSCAN | 03-01-2017 2:15AM(UTC) | ********** |
| BEFORE | OTHER | 02-28-2017 10:22PM(UTC) | ********* |
| | PURCHCONSENT | 02-28-2017 10:22PM(UTC) | ********* |
| | HXCONSENT | 02-28-2017 10:15PM(UTC) | ********* |

2318

| CASE DOCUMENTS |
|---|
| FRENECTOMY CONSENT (03-02-2017 3:35PM) |
| VIEW DOCUMENTS |
| REMINDER  REMOVE |

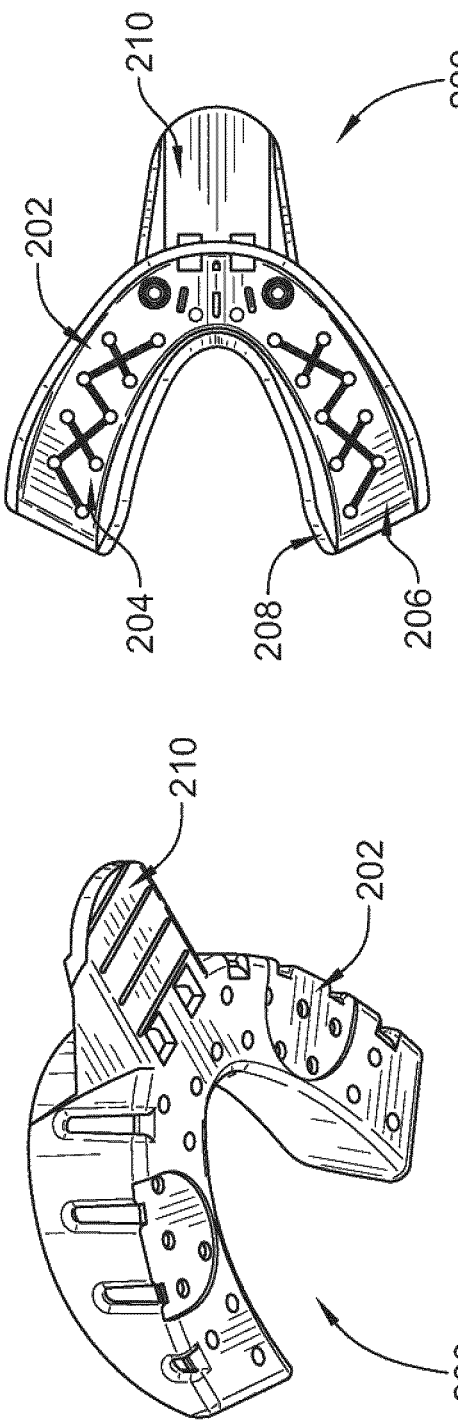
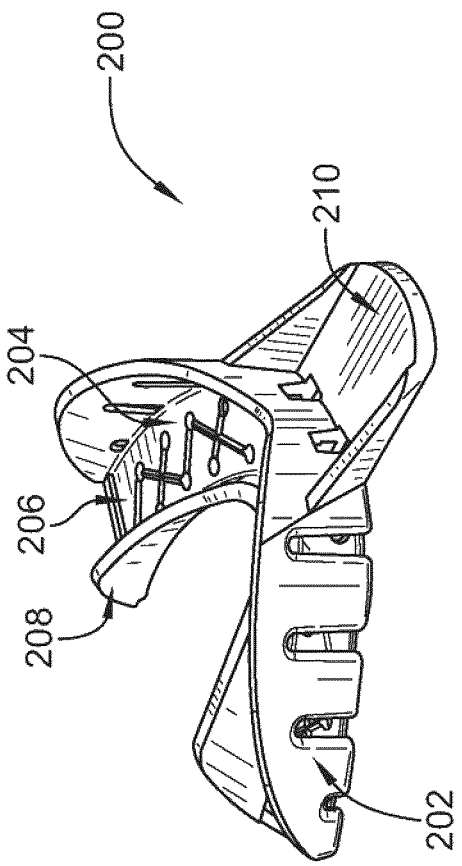

*2700*

| FILES | | | |
|---|---|---|---|
| NAME | KIND | UPLOAD DATE | UPLOADED BY |
| 90 DAY PROGRESS NOTE | 90DAYNOTE | 06-14-2017 5:40 PM (UTC) | ERMINIA SARLEY |
| 90 DAY PROGRESS PHOTO | 90DAYPHOTO | 06-14-2017 5:39 PM (UTC) | ERMINIA SARLEY |
| UPPER | 3DSCAN | 02-18-2017 4:54 PM (UTC) | F792D1AFBO@399DCE4753.COM |
| LOWER | 3DSCAN | 02-18-2017 4:53 PM (UTC) | F792D1AFBO@399DCE4753.COM |
| LOWER | 3DSCAN | 02-20-2017 3:54 PM (UTC) | F792D1AFBO@399DCE4753.COM |
| UPPER | 3DSCAN | 02-20-2017 3:57 PM (UTC) | F792D1AFBO@399DCE4753.COM |

| 90 DAY REVIEW | | |
|---|---|---|
| SEND 90 DAY REVIEW TO PROVIDER PORTAL | | |
| DATE SENT | SENT BY | STATUS |
| WEDNESDAY, JUNE 14, 2017 5:41 P.M. UTC | *@* | READY |

- LOCATION — 3202
  - SCANNING SITE 1 (LOCATION) (DISTANCE)
  - SCANNING SITE 2 (LOCATION) (DISTANCE)
  - ...
  - SCANNING SITE N (LOCATION) (DISTANCE)

- DATE — 3204, 3200
  - TODAY - FRIDAY, MO. DAY
  - TOMORROW - SATURDAY, MO. DAY
  - SUNDAY, MO. DAY
  - ...
  - DAY, DATE

PLEASE SELECT A TIME:

FIRST NAME

LAST NAME

3332

PHONE NUMBER

E-MAIL ADDRESS

☒ SEND ME MESSAGES WITH MY APPOINTMENT REMINDER, DIRECTIONS, AND DETAILS ABOUT MY NEW SMILE

3304

ORDER SUMMARY: FREE

SUBTOTAL $0.00
TAX $0.00

GRAND TOTAL $0.00

( BOOK MY SCAN )

3306

DISTRIBUTED PROCESSING OF SCAN DATA FOR FABRICATING DENTAL ALIGNERS

CROSS-REFERENCE TO RELATED APPLICATIONS

This application a continuation of U.S. patent application Ser. No. 17/247,296, filed Dec. 7, 2020, which is a continuation of U.S. patent application Ser. No. 16/859,950, filed Apr. 27, 2020, which is a continuation of U.S. patent application Ser. No. 16/130,762, filed Sep. 13, 2018, which claims the benefit of U.S. Provisional Patent Application No. 62/660,141, filed Apr. 19, 2018, and is a continuation-in-part of U.S. patent application Ser. No. 15/725,430, filed Oct. 5, 2017, which claims the benefit of U.S. Provisional Patent Application No. 62/522,847, filed Jun. 21, 2017, each of which are incorporated herein by reference in their entirety.

TECHNICAL FIELD

The present disclosure relates generally to the field of intraoral scanning, and more specifically, to intraoral scanning for generating a three-dimensional image of a user's teeth that is used in treating misalignment of the user's teeth.

BACKGROUND

Dental impressions and associated physical or digital reproductions of a patient's teeth can be used by dentists or orthodontists to diagnose or treat an oral condition, such as the misalignment of the patient's teeth. For example, to take a dental impression, a dental tray having a viscous, thixotropic impression material is fit over the dental arches of the patient, and then the impression material sets to a solid over time, thereby providing an imprint of the patient's dental arches once the dental trays are removed from the patient's mouth. The impressions provide a detailed and stable negative of the patient's teeth and tissues in their mouth. The negative impressions may then be utilized to produce a physical or digital reproduction of the patient's teeth and surrounding tissues.

Traditionally, dental impressions are made in a dental office and require significant time. Dental offices typically deliver the dental impressions to an outside vendor that utilizes the impressions to form a positive model of the teeth and surrounding tissue. If the dental impressions includes any errors (e.g., incomplete impression of the teeth and tissues), the patient may be required to return to the dental office to have a second impression made. Furthermore, if the dental impressions are used by the dental professional in the course of administering a continuing treatment plan, the patient is typically required to undergo many check-up appointments at the dental office so that the dental professional can track the patient's treatment and modify the treatment plan as necessary. Each of these examples results in significant inconvenience to the patient and increases the cost of the treatment plan to both the dental professional and the patient.

SUMMARY

According to one aspect of the disclosure, a method of producing aligners for repositioning one or more teeth of a user is disclosed. The method includes receiving, by an appointment management system, a request to schedule an appointment at an intraoral scanning site having an intraoral scanner configured to conduct an intraoral scan of a mouth of a user. The method includes scheduling, by the appointment management system, the appointment in accordance with the request. The method includes generating and communicating, by the appointment management system, a message to the user. The message includes a confirmation confirming the scheduled appointment. The method includes conducting, using the intraoral scanner, the intraoral scan at the intraoral scanning site during the scheduled appointment. The intraoral scan generates three-dimensional data of the mouth of the user. The method includes generating, by a treatment plan computing system at a treatment plan site, a treatment plan for the user based on the three-dimensional data of the mouth of the user. The method includes receiving an approval of the treatment plan by a dental or orthodontic professional. The approval is received without the dental or orthodontic professional physically seeing the user in person. The method includes producing, at a fabrication site, a plurality of aligners based on the treatment plan. The plurality of aligners are specific to the user and are configured to reposition one or more teeth of the user in accordance with the treatment plan. The method includes sending the plurality of aligners to the user.

According to another aspect of the disclosure, a method of administering aligners for repositioning one or more teeth of a user is disclosed. The method includes requesting, via a web portal or mobile application, an appointment at an intraoral scanning site having an intraoral scanner configured to conduct an intraoral scan of a mouth of a user. The method includes receiving, from an appointment management system, a confirmation message confirming the scheduled appointment. The method includes receiving, via the intraoral scanner, the intraoral scan at the intraoral scanning site during the scheduled appointment. The intraoral scanner generates three-dimensional dimensional data of the mouth of the user. The method includes receiving a plurality of aligners which are generated in accordance with a treatment plan. The treatment plan is generated at a computing system by a dental or orthodontic professional without physically seeing the user. The treatment plan is generated based on the three-dimensional data of the mouth of the user. The plurality of aligners are specific to the user and configured to reposition one or more teeth of the user in accordance with the treatment plan. The method includes administering the plurality of aligners in a predetermined sequence to reposition the one or more teeth of the user in accordance with the treatment plan.

According to another aspect of the disclosure, a system for generating aligners for modifying an alignment of a user's teeth is disclosed. The system includes an appointment management system, an intraoral scanning site, and a fabrication site. The appointment management system is configured to receive a receive a request to schedule an appointment for receiving an intraoral scan of a mouth of a user. The appointment management system is further configured to schedule the appointment. The appointment management system is further configured to generate and communicate a message to a user device associated with the user. The message includes a confirmation confirming the scheduled appointment. The intraoral scanning site includes an intraoral scanner configured to generate three-dimensional data from an intraoral scan of the mouth of the user. The intraoral scanning site includes one or more computing systems configured to communicate the three-dimensional data from the intraoral scan for generation of a treatment plan. The fabrication site includes one or more computing systems configured to receive data corresponding to the treatment plan. The fabrication site includes thermoforming equipment configured to produce a plurality of aligners based on the treatment plan data. The plurality of aligners are specific to the user and are configured to reposition one or more teeth of the user in accordance with the treatment plan. The one or more aligners are sent to the user for repositioning the one or more teeth of the user.

Various other embodiments and aspects of the disclosure will become apparent based on the drawings and detailed description of the following disclosure.

BRIEF DESCRIPTION OF THE DRAWINGS

FIG. 26 is a screen shot of a smile assessment user interface that may be generated by the application server of FIGS. 22-23;

FIG. 27 is a screen shot of an account status user interface that may be generated by the application server of FIGS. 22-23;

FIGS. 29A-29E are screen shots of a dental history questionnaire user interface that may be generated by the application server of FIGS. 22-23;

FIGS. 30A and 30B are screen shots of a photo assessment user interface that may be generated by the application server of FIGS. 22-23;

FIGS. 31A-31E are screen shots of a provider portal user interface that may be generated by the application server of FIGS. 22-23;

FIGS. 34A-34F are screen shots of a staff portal user interface that may be generated by the application server of FIGS. 22-23;

FIGS. 35-37 are views of another embodiment of a dental tray;

FIGS. 38A-38D are screen shots of a check-in process user interface that may be generated by the application server of FIGS. 22-23;

FIG. 40 shows a reservations screen associated with the appointment management system of FIG. 39 according to an exemplary embodiment;

FIG. 41 shows a booking screen associated with the appointment management system of FIG. 39 according to an exemplary embodiment;

DETAILED DESCRIPTION

The present disclosure is directed to systems and methods for conducting an intraoral scan of a user at a location. A user can request an appointment at an intraoral scanning site. For example, the user can request an appointment in advance of the requested appointment time (e.g., online, via a mobile application, via a telephone call) or the user can request an appointment at the time of requested appointment (e.g., a "walk in"). In requesting the appointment at the intraoral scanning site, the user can provide various information for reserving the appointment, such as a reason for making the appointment (e.g., misaligned teeth) or a dental condition of the patient (e.g., having crowns, an impacted tooth). The user can make the request online (e.g., via an internet scheduling website associated with the intraoral scanning site). When the appointment timeslot is held for the user, one or more scheduling alerts can be communicated to the user (e.g., confirmation notification, reminder notification, appointment modification query). Upon arriving at the appointment, the user can provide health history and consent information. The user can receive the intraoral scan, and upon confirmation from the user to purchase the aligners, one or more sets of aligners configured to modify the alignment of the user's teeth can be sent to the user.

The systems and methods described herein may have many benefits including, but not limited to, increasing user excitement about the alignment process, increasing the likelihood of a user showing up for their appointment, and increasing the likelihood of a user purchasing aligners at the intraoral scanning site, as will be discussed in greater detail below.

Figure 1:
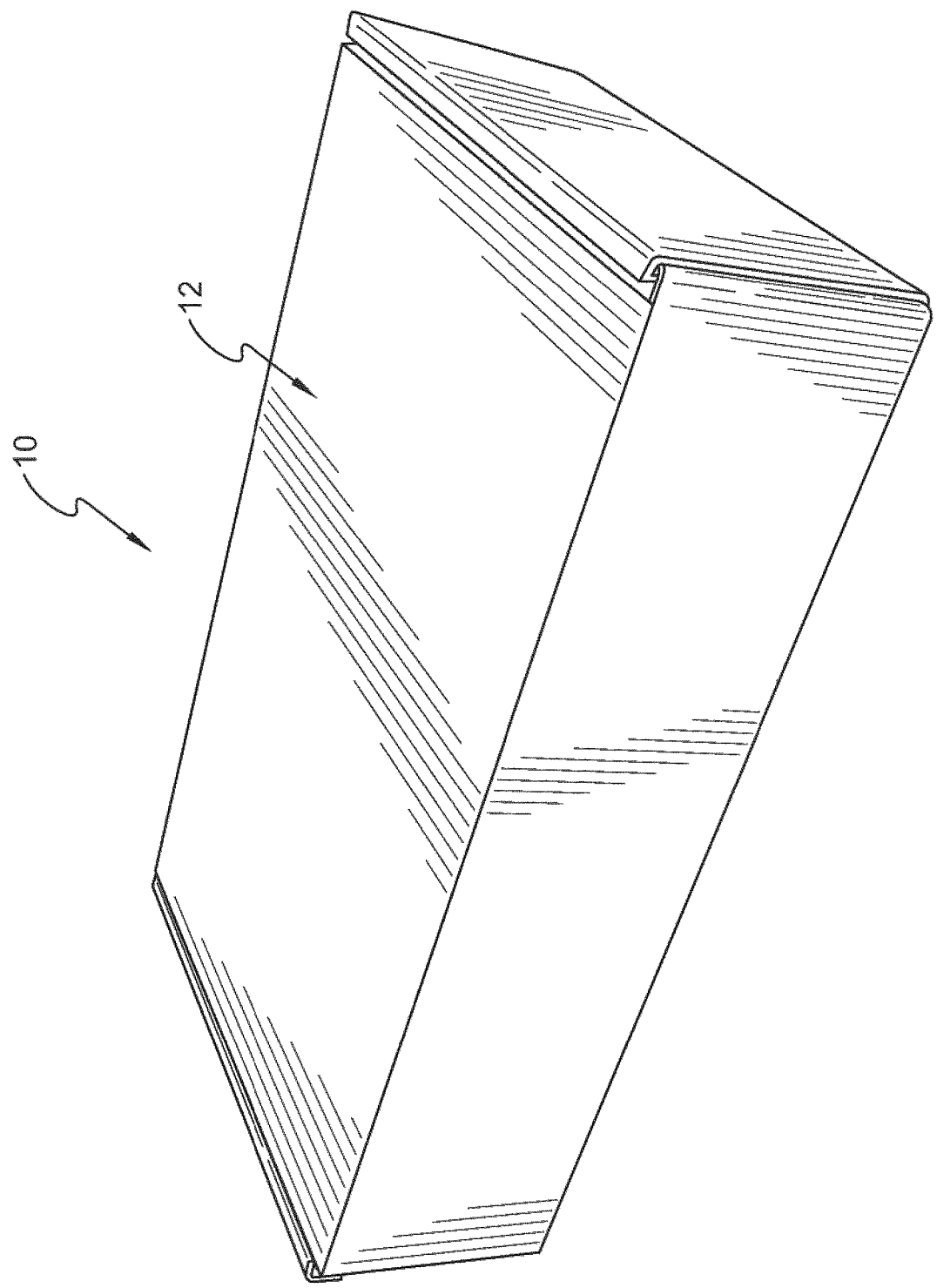
FIG. 1 is a perspective view of a container that contains the contents of a dental impression kit.

Referring to FIG. 1, a dental impression kit 10 is shown having dental assemblies (discussed in more detail below) therein. The dental impression kit 10 may be ordered by a customer and shipped in a container or box 12, shown in FIG. 1, from a vendor. After administering the dental impression kit 10 at home, the customer may ship the dental impression kit 10 in the box 12 back to the vendor for analysis. The box 12 is sized for standard shipping and is likewise sized for delivery into the customer's mailbox. Accordingly, additional fees for shipment of the dental impression kit 10 in the box 12 may not be required.

Figure 2:
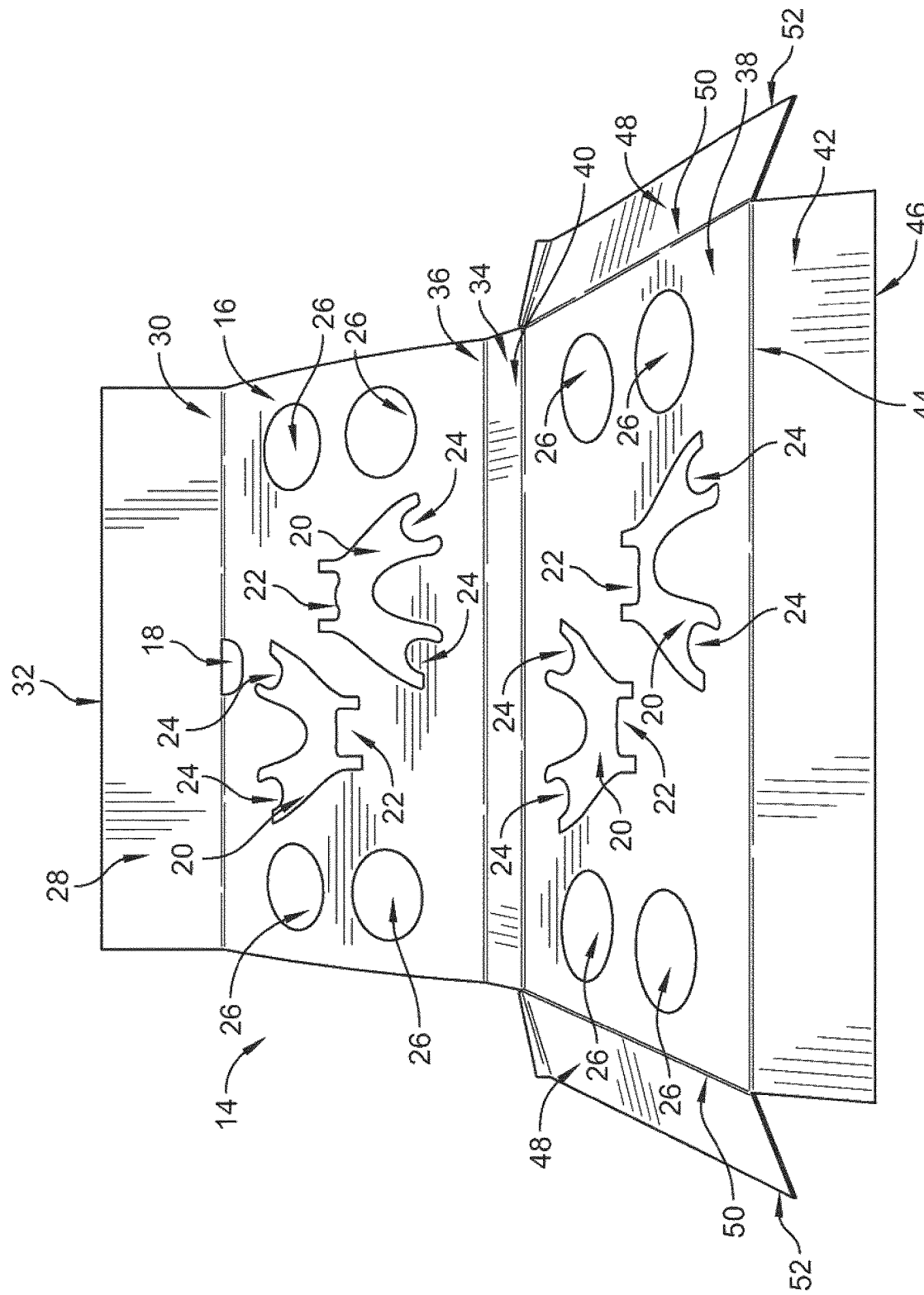
FIG. 2 is a perspective view of an insert that is positioned within the container shown in FIG. 1.

Referring to FIG. 2, the box 12 includes an insert 14 therein that is configured to retain the dental assemblies. The insert 14 includes a top layer 16 having a plurality of cutouts formed therein. A front cutout 18 is sized and shaped to receive a user's finger to lift the top layer 16 from the box 12. A pair of tray cutouts 20 are sized and shaped to retain dental trays (described below). The tray cutouts 20 include a flange 22 that is sized and shaped to retain a front flange of the dental tray. A pair of flanges 24 retain rear ends of the dental tray. Circular cutouts 26 are sized and shaped to retain containers of putty (described below).

A front flap 28 is joined to the top layer 16 along a fold line 30. The front flap 28 is configured to be folded such that an end 32 of the front flap 28 engages a bottom of the box 12, when the insert 14 is positioned within the box 12. The front flap 28 supports the top layer 16 within the box 12. A center flap 34 extends from the top layer 16 along a fold line 36. The center flap 34 is also connected to a second or bottom layer 38 along a fold line 40. When the insert 14 is positioned within the box 12, the center flap 34 supports the top layer 16 within the box.

The bottom layer 38 is configured to be positioned below the top layer 16, when the insert 14 is positioned within the box 12. The bottom layer 38 also includes a plurality of cutouts formed therein. A pair of tray cutouts 20 are sized and shaped to retain dental trays. The tray cutouts 20 include a flange 22 that is sized and shaped to retain a front flange of the dental tray. A pair of flanges 24 retain rear ends of the dental tray. Circular cutouts 26 are sized and shaped to retain containers of putty.

A front flap 42 extends from the bottom layer 38 along a fold line 44. The front flap 42 is configured to be folded such that an end 46 of the front flap 42 engages a bottom of the box 12, when the insert 14 is positioned within the box 12. A pair of side flaps 48 extends from the bottom layer 38 along fold lines 50. The side flaps 48 are configured to be folded such that an end 52 of each side flap 48 engages a bottom of the box 12, when the insert 14 is positioned within the box 12. Accordingly, the front flap 42 and the side flaps 48 support the bottom layer 38 within the box 12, when the insert 14 is positioned within the box 12.

In some embodiments, the top layer 16 and the bottom layer 38 are not integrally formed. In such an embodiment, the top layer 16 is configured to be positioned on top of the bottom layer 38 such that the top layer is individually removable while the bottom layer 38 remains within the box 12.

Figure 3:
FIG. 3 is a perspective view of the container shown in FIG. 1 in an open configuration to expose an instruction manual.

Referring to FIG. 3, when the box 12 is opened, an instruction manual 54 is positioned at a top of the box contents. The instruction manual 54 provides step-by-step instructions for administering the contents of the dental impression kit 10. A method for administering the dental impression kit 10 according to the instructions is described in more detail with respect to FIG. 10.

Figure 4:
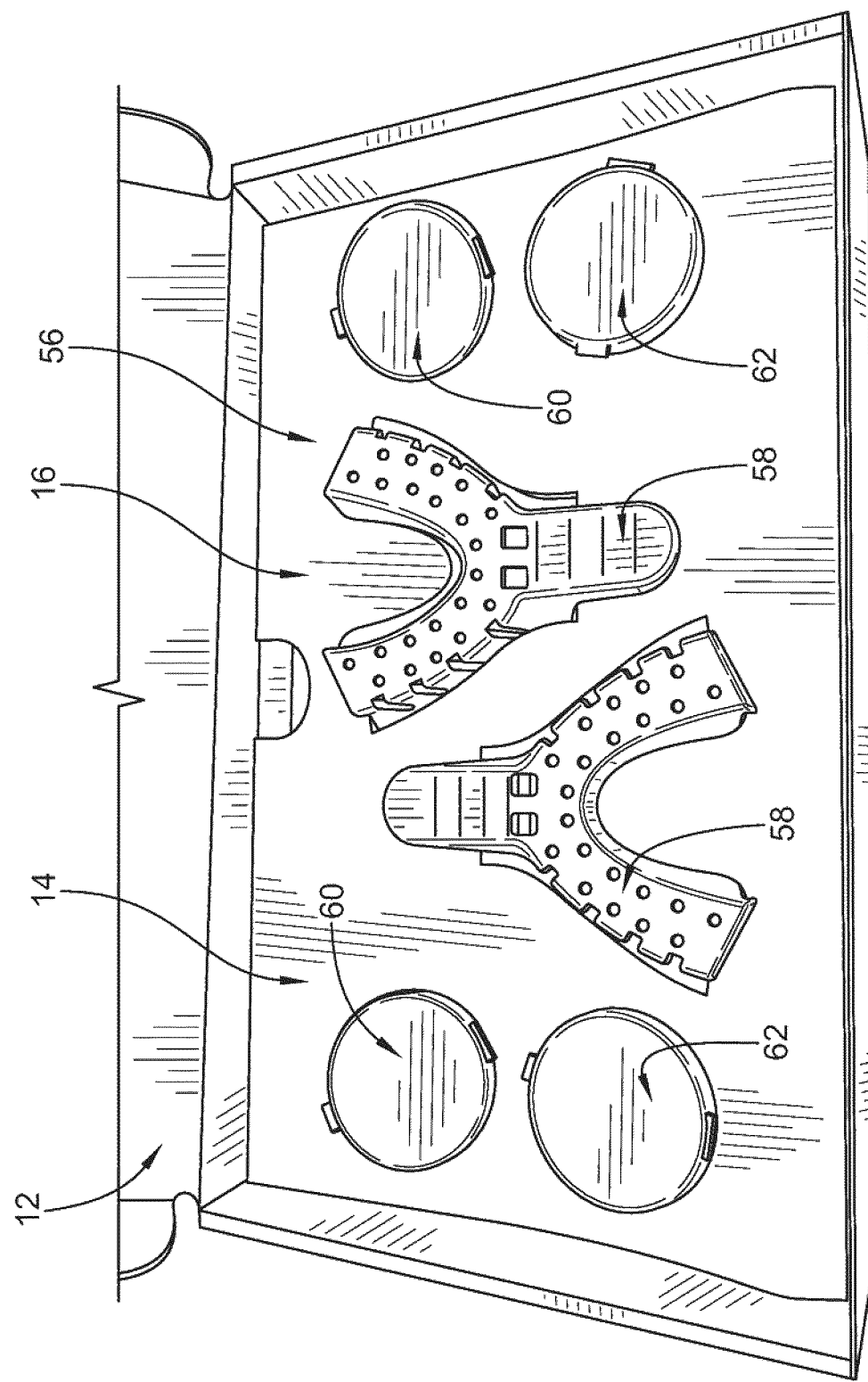
FIG. 4 is a perspective view of a top layer of the insert shown in FIG. 2 and having part of the dental impression kit therein.
Figure 7:
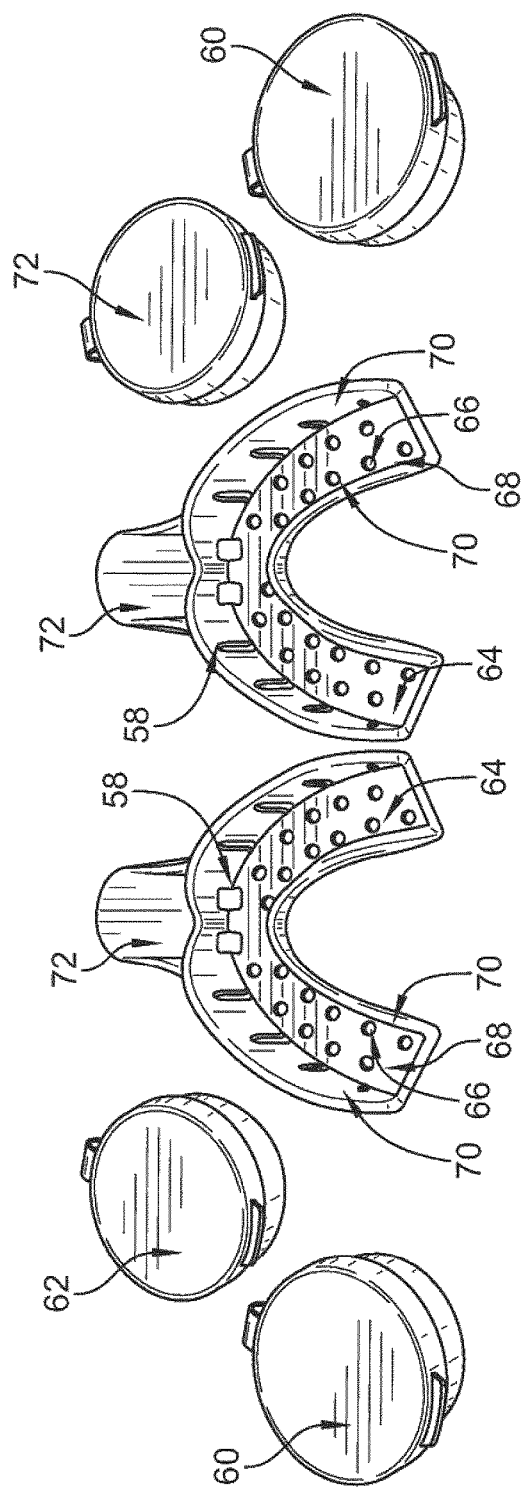
FIG. 7 is a perspective view of part of the dental impression kit including dental trays, base putty containers, and catalyst putty containers.

Referring to FIG. 4, when the instruction manual 54 is removed from the box 12, the top layer 16 of the insert 14 is exposed. The top layer 16 includes the contents of an initial dental assembly 56. Referring to FIG. 7, the initial dental assembly 56 includes two initial dental trays 58, two containers of an initial base putty 60, and two containers of an initial catalyst putty 62. The instruction manual 54 includes initial instructions for administering the initial dental assembly 56. Generally, in use, a container of initial base putty 60 is mixed with a container of initial catalyst putty 62 to form a putty mixture. The putty mixture is then positioned in one of the initial dental trays 58 to form a dental impression of the upper teeth. The second container of initial base putty 60 is then mixed with the second container of initial catalyst putty 62 to form another putty mixture that is positioned in the second initial dental tray 58 to form a dental impression of the lower teeth. This process is explained in more detail below with respect to FIG. 10.

Still referring to FIG. 7, the initial dental trays 58 include a substantially arched mouth insert 64 that is sized and shaped to be inserted into the user's mouth. Particularly, the insert 64 is sized and shaped to be received into either an upper portion or a lower portion of the user's mouth. The insert 64 includes a cavity 66 defined by a bottom wall 68 and a pair of sidewalls 70 extending upward from the bottom wall 68. The cavity 66 is sized to receive the putty mixture. When the initial dental tray 58 is inserted into the user's mouth, the user bites down on the initial dental tray 58 so that the user's teeth are within the cavity 66 and bite into the putty mixture. A flange 72 extends from a front of the initial dental tray 58. The flange 72 is configured to be gripped by the user to insert and remove the initial dental tray 58 from the user's mouth.

In some embodiments, the initial catalyst putty 62 is a polyvinyl siloxane that provides a predetermined period of time to set when mixed with the initial base putty 60. The predetermined period of time is based on a period of time necessary for a user to administer the dental impression kit 10 at home. That is, the predetermined period of time is selected to allow the user enough time to prepare the putty mixture and dental impression, while also preventing the putty mixture from deforming when the initial dental tray 58 having the putty mixture therein is removed from the user's mouth. In some embodiments, the initial base putty 60 and the initial catalyst putty 62 may be required to be at room temperature before mixing.

Referring back to FIG. 4, after the initial dental assembly 56 is used to form an initial set of dental impressions of both the upper and lower teeth, the user may grip the top layer 16 by the front cutout 18 and lift the top layer 16 from the box 12. Specifically, the top layer 16 folds back along the fold line 36 to expose the bottom layer 38.

Figure 5:
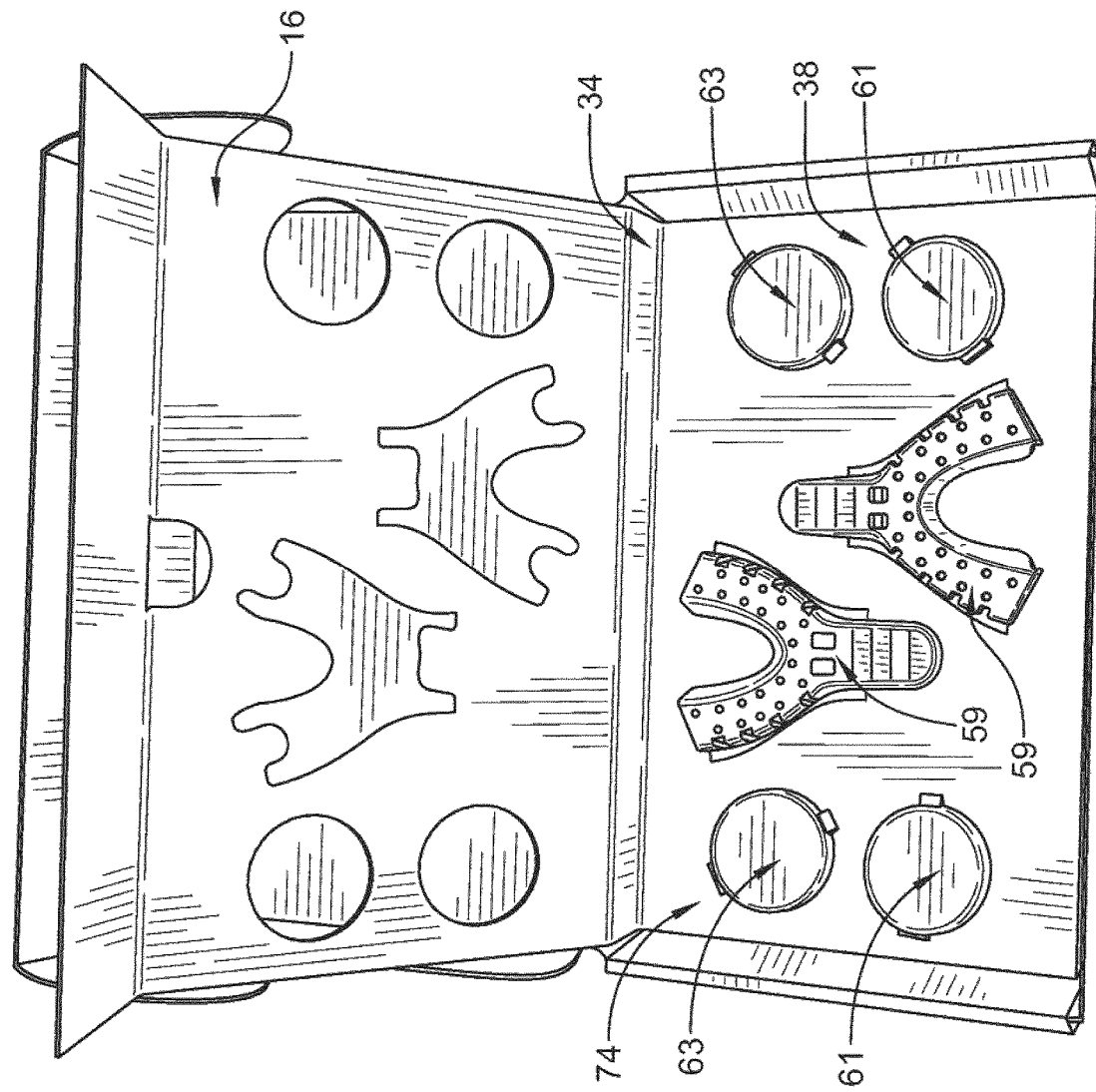
FIG. 5 is a perspective view of a bottom layer of the insert shown in FIG. 2 and having part of the dental impression kit therein.

FIG. 5 shows, the top layer 16 folded back to expose the bottom layer 38. Notably, the top layer 16 is still connected to the bottom layer 38 by the center flap 34; however, the top layer 16 is folded back so that the bottom layer 38 may be accessed. The bottom layer 38 includes a redundant dental assembly 74. The redundant dental assembly 74 is identical to the initial dental assembly 56, described with respect to FIG. 7, and includes two redundant dental trays 59 that are identical to the initial dental trays 58 described with respect to FIG. 7, two containers of a redundant base putty 61 that are identical to the containers of initial base putty 60 described with respect to FIG. 7, and two containers of a redundant catalyst putty 63 that are identical to the containers of initial catalyst putty described with respect to FIG. 7. The instruction manual 54 includes redundant instructions for administering the redundant dental assembly 74. The redundant dental assembly 74 is utilized to form a second set of dental impressions of the upper and lower teeth (as described below). Accordingly, the redundant dental assembly 74 provides redundancy in administering the dental impression kit 10. This redundancy enables the user to "practice" forming the dental impression with the initial dental assembly 56. Alternatively or in addition to, the redundancy provides for two sets of dental impressions if one of the impressions is not properly achieved.

Figure 6:
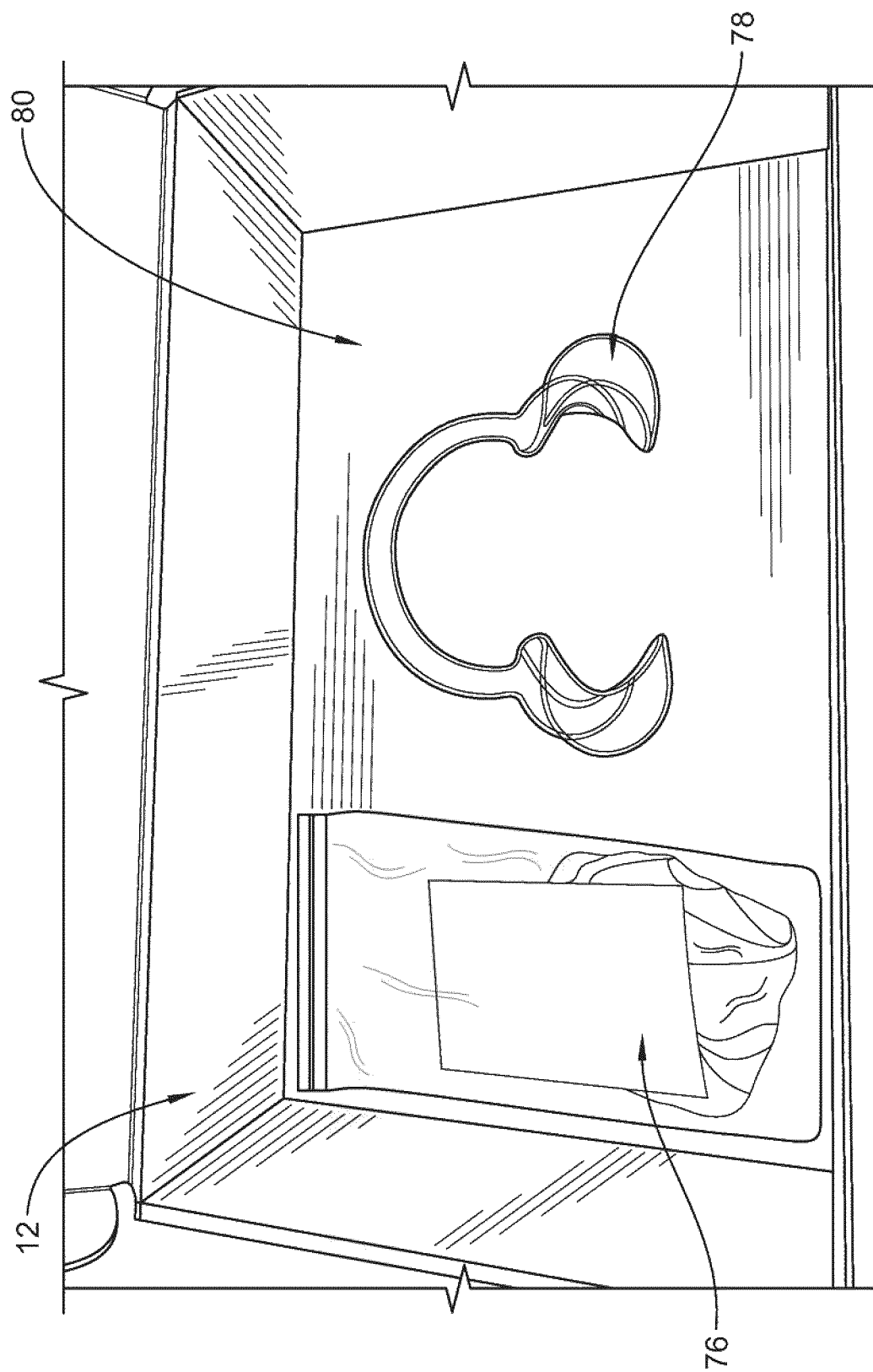
FIG. 6 is a perspective view of a bottom of the container shown in FIG. 1 and having part of the dental impression kit therein.

Referring to FIG. 6, a pair of gloves 76 and a dental appliance 78 are included at a bottom 80 of the box 12. Particularly, the pair of gloves 76 and the dental appliance 78 are positioned below the insert 14. When opening the dental impression kit 10, the user may first remove the instruction manual 54 and the insert 14 to gain access to the pair of gloves 76 and the dental appliance 78. The insert 14 may then be positioned back into the box so that the user may appropriately follow the instructions in the instruction manual 54, as described in more detail below.

Figure 8:
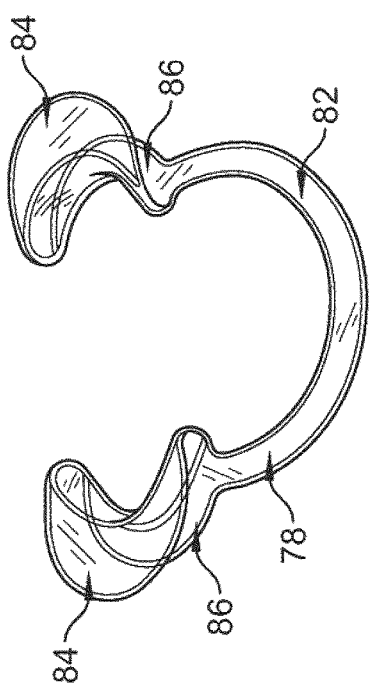
FIG. 8 is a perspective view of a dental appliance that is included in the dental impression kit.

Referring to FIG. 8, the dental appliance 78 includes a handle 82 having a pair of flanges 84 at each end. The flanges 84 are generally U-shaped and form a cavity 86. The instruction manual 54 includes appliance instructions for utilizing the dental appliance 78. The cavity 86 is configured to receive the user's lips at the sides of the user's mouth. The dental appliance 78 is configured to separate the user's lips to open the user's mouth. In this position, the user may photograph his/her teeth, as described in more detail below.

Figure 9:
FIG. 9 is a perspective view of gloves that are included in the dental impression kit.

FIG. 9 shows the pair of gloves 76. In some embodiments, the gloves 76 are formed from a non-latex, hypo-allergenic material. The gloves 76 may also be sized and stretchable for any user's hands. The gloves 76 are used to protect the user's hands from the initial base putty 60 and the initial catalyst putty 62. The gloves 76 also prevent contamination of the initial base putty 60 and the initial catalyst putty 62.

Figure 10:
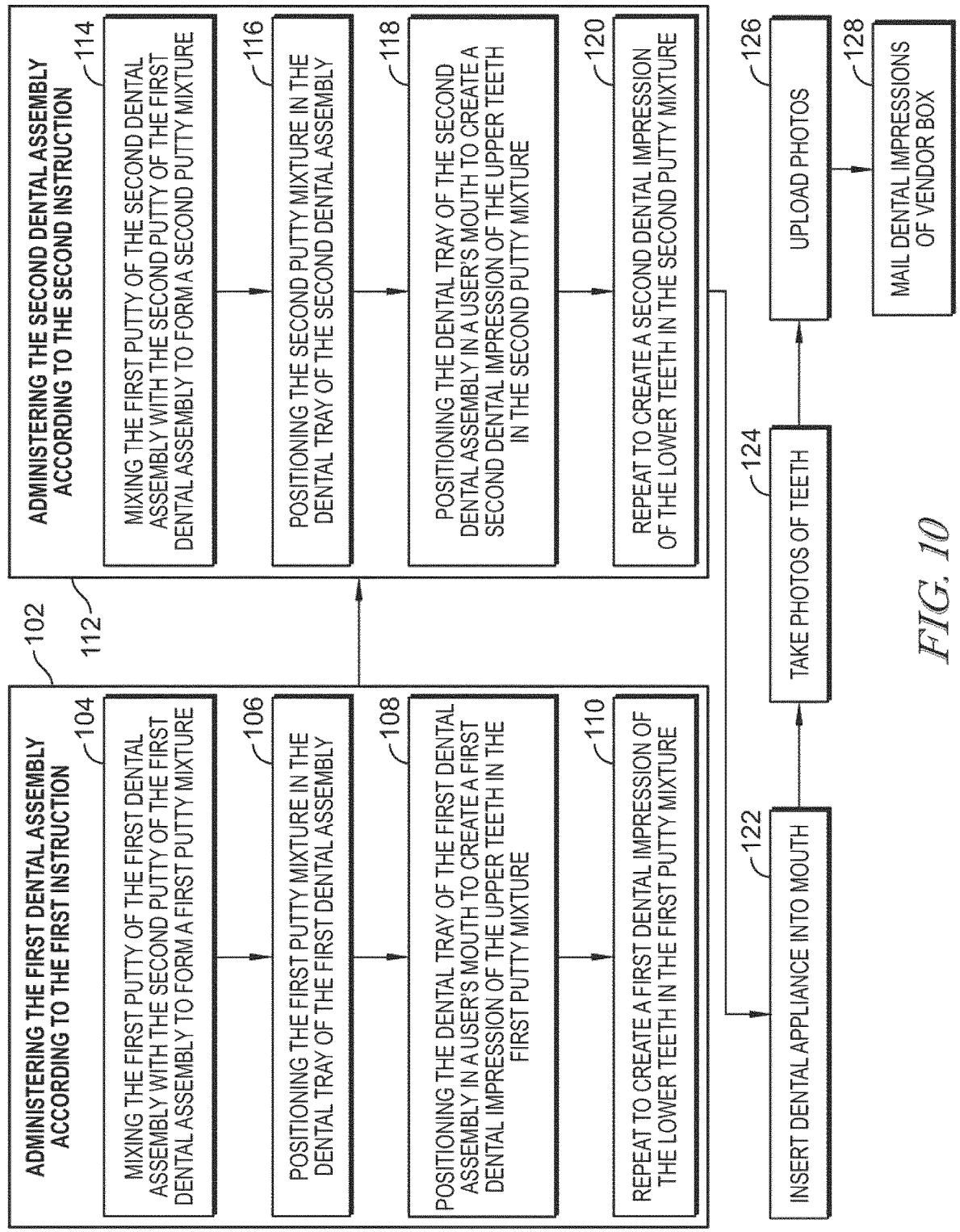
FIG. 10 is a flowchart of a method for administering the dental impression kit shown in FIGS. 1-9.

Referring to FIG. 10, a method 100 for administering the dental impression kit 10 includes receiving from a vendor the dental impression kit 10 in the box 12 in the mail. The box 12 is opened so that the user may obtain the instruction manual 54 for the dental impression kit 10. After removing the instruction manual 54, the entire insert 14 may be removed to expose the gloves 76 and the dental appliance 78. After the gloves 76 and dental appliance 78 are removed from the box 12, the insert 14 is positioned back into the box 12 so that the instruction manual 54 may be properly followed. The user is instructed to wash his/her hands and put the gloves 76 on before proceeding.

With the insert 14 positioned back into the box 12, the top layer 16 is exposed. The initial dental assembly 56 is then administered, at step 102, by following the initial instruction of the instruction manual 54. At step 104, the initial base putty 60 is mixed with the initial catalyst putty 62 to form an initial putty mixture. In some embodiments, the initial base putty 60 is mixed with the initial catalyst putty 62 for approximately 20 seconds to form the initial putty mixture. In other embodiments, the initial base putty 60 is mixed with the initial catalyst putty 62 for a time period required by the putty type and/or environmental conditions. For example, the mixing time may vary based on geographical region or the time of year, e.g. summer or winter. At step 106, the initial putty mixture is then positioned within the cavity 66 of the initial dental tray 58. In some embodiments, the user is instructed to position the initial putty mixture within the cavity 66 of the initial dental tray 58 within a time frame of approximately less than or equal to one minute from the time the initial base putty and 60 the initial catalyst putty 62 are opened. In other embodiments, the initial putty mixture is positioned within the cavity 66 of the initial dental tray 58 within a time period required by the putty type and/or environmental conditions. For example, the time may vary based on geographical region or the time of year, e.g. summer or winter. With the initial putty mixture positioned within the cavity 66 of the initial dental tray 58, the user then inserts the initial dental tray 58 into his/her mouth and bites down so that the user's upper teeth are positioned within the initial putty mixture to form an initial dental impression, at step 108. In some embodiments the initial dental tray 58 is retained within the user's mouth for a time period of approximately 2.5 to 3.5 minutes to create the initial dental impression. In other embodiments, the initial dental tray 58 is retained within the user's mouth for a time period required by the putty type and/or environmental conditions. For example, the time may vary based on geographical region or the time of year, e.g. summer or winter. At step 110, steps 104-108 are repeated using the second initial dental tray 58, the second container of initial base putty 60, and the second container of initial catalyst putty 62 to form an initial dental impression of the user's lower teeth.

After the initial set of dental impressions has been made, the user folds the top layer 16 back to expose the bottom layer 38 and the redundant dental assembly 74. The redundant dental assembly 74 is then administered, at step 112, by following the redundant instruction of the instruction manual 54. At step 114, the redundant base putty 61 is mixed with the redundant catalyst putty 63 to form a redundant putty mixture. In some embodiments, the redundant base putty 61 is mixed with the redundant catalyst putty 63 for approximately 20 seconds to form the redundant putty mixture. In other embodiments, the redundant base putty 61 is mixed with the redundant catalyst putty 63 for a time period required by the putty type and/or environmental conditions. For example, the time may vary based on geographical region or the time of year, e.g. summer or winter. The redundant putty mixture is then positioned within the cavity 66 of the redundant dental tray 59, at step 116. In some embodiments, the user is instructed to position the redundant putty mixture within the cavity 66 of the redundant dental tray 59 within a time frame of approximately less than or equal to one minute from the time the redundant base putty 61 the redundant catalyst putty 63 are opened. In other embodiments, the redundant putty mixture is positioned within the cavity 66 of the redundant dental tray 59 within a time period required by the putty type and/or environmental conditions. For example, the time may vary based on geographical region or the time of year, e.g. summer or winter. With the redundant putty mixture positioned within the cavity 66 of the redundant dental tray 59, the user then inserts the redundant dental tray 59 into his/her mouth and bites down so that the user's upper teeth are positioned within the redundant putty mixture to form a redundant dental impression, at step 118. In some embodiments the redundant dental tray 59 is retained within the user's mouth for a time period of approximately 2.5 to 3.5 minutes to create the redundant dental impression. In other embodiments, the redundant dental tray 59 is retained within the user's mouth for a time period required by the putty type and/or environmental conditions. For example, the time may vary based on geographical region or the time of year, e.g. summer or winter. At step 120, steps 114-118 are repeated using the second redundant dental tray 59, the second container of redundant base putty 61, and the second container of redundant catalyst putty 63 to form a redundant dental impression of the user's lower teeth.

After administering the initial dental assembly 56 and the redundant dental assembly 74, the user has created two sets of dental impressions of both his/her upper teeth and his/her lower teeth. The insert 14 may be removed from the box 12 and discarded. The dental appliance 78 is then inserted into the user's mouth to separate the user's lips and expose the user's teeth, at step 122. With the dental appliance 78 in his/her mouth, the user takes a series of photos of his/her teeth in accordance with an appliance instruction in the instruction manual 54, at step 124. These photos may then be uploaded to the vendor's website via a web portal or the like, at step 126. The user then positions both sets of dental impressions, i.e. the upper and lower initial dental impressions from the initial dental assembly 56 and the upper and lower redundant dental impressions from the redundant dental assembly 74 into the empty box 12. It should be noted that the dental impressions are not removed from the dental trays 58, 59. That is, the dental trays 58, 59 with the dental impressions therein are positioned in the box 12. The box is then sealed with a sticker included within the dental impression kit 10. At step 128, the box 12 with the dental impressions sealed therein is mailed back to the vendor using a return mailing label that is included in the dental impression kit 10.

Figure 11:
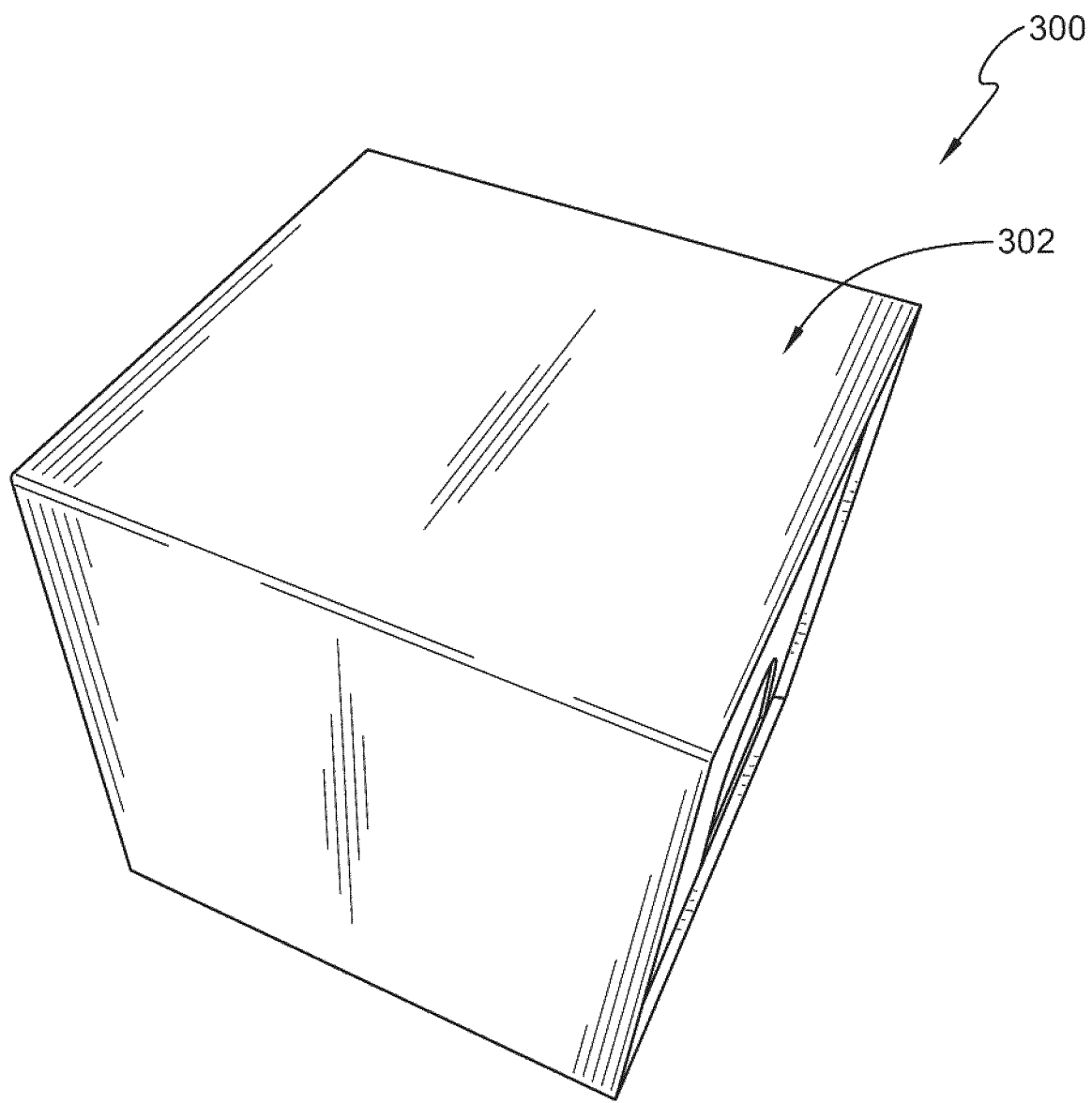
FIG. 11 is a perspective view of another container that contains the contents of a dental impression kit.

Referring to FIG. 11, a dental impression kit 300 is shown having dental assemblies (discussed in more detail below) therein. The dental impression kit 300 may be ordered by a customer and shipped in a container or box 302, shown in FIG. 11, from a vendor. After administering the dental impression kit 300 at home, the customer may ship the dental impression kit 300 in the box 302 back to the vendor for analysis. The box 302 is sized for standard shipping and is likewise sized for delivery into the customer's mailbox. Accordingly, additional fees for shipment of the dental impression kit 300 in the box 302 may not be required.

Figure 12:
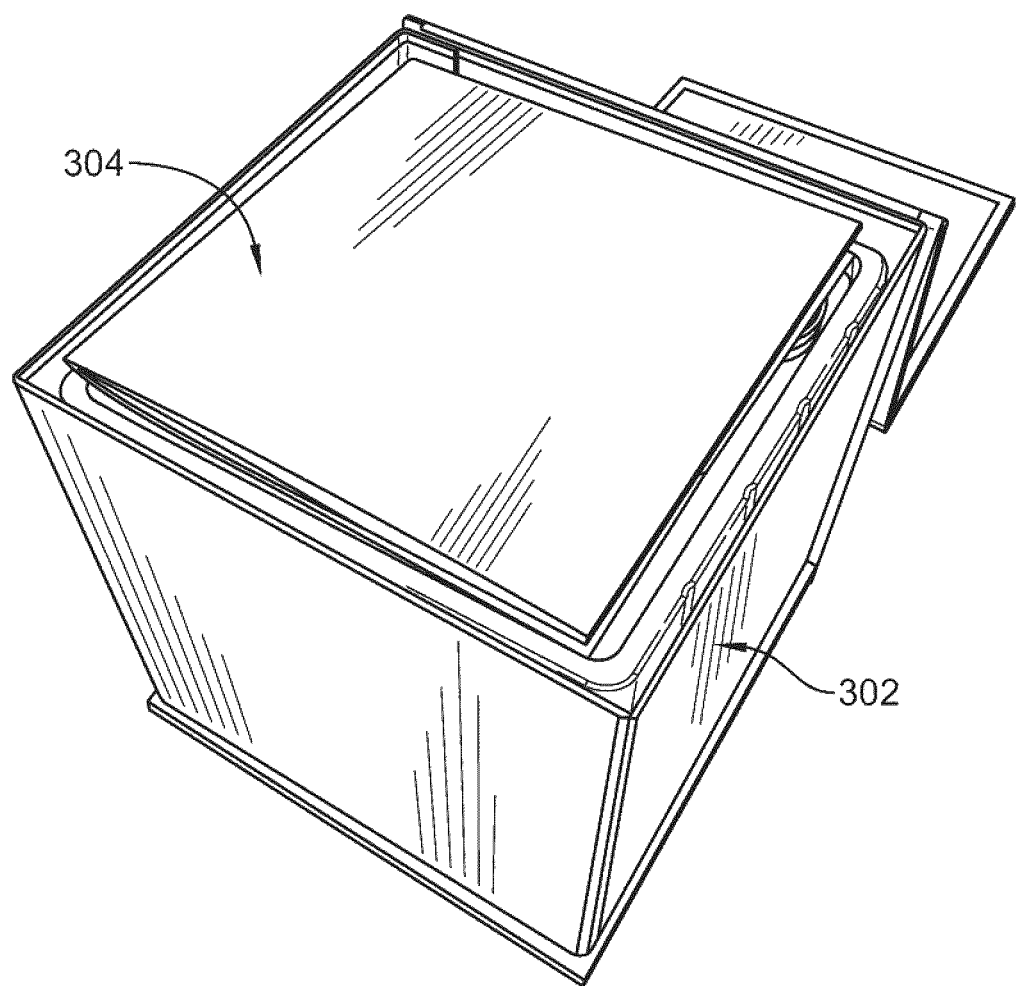
FIG. 12 is a perspective view of the container shown in FIG. 11 opened.
Figure 13:
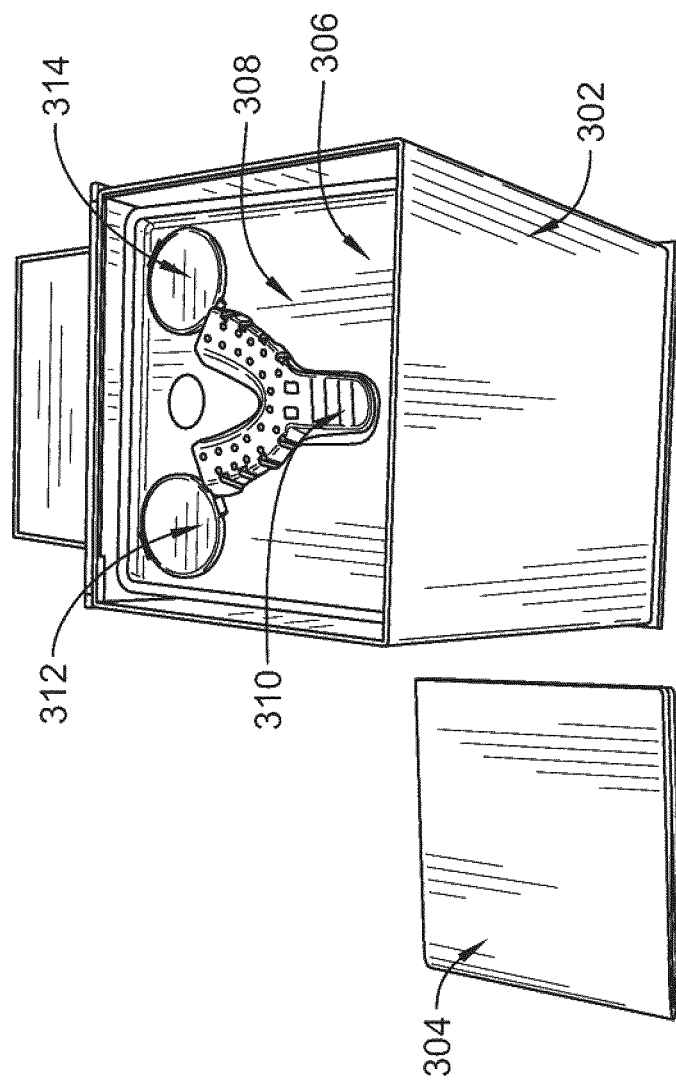
FIG. 13 is a perspective view of an initial dental assembly insert that is positioned within the container shown in FIG. 11.

Referring to FIG. 12, when the box 302 is opened, an instruction manual 304 is positioned at a top of the box contents. The instruction manual 304 provides step-by-step instructions for administering the contents of the dental impression kit 300. Referring to FIG. 13, when the instruction manual 304 is removed from the box 302, an insert 306 is exposed that includes the contents of an upper initial dental assembly 308. The initial upper dental assembly 308 includes an initial upper dental tray 310, a container of an initial upper base putty 312, and a container of an initial upper catalyst putty 314. The instruction manual 304 includes initial instructions for administering the initial upper dental assembly 308. Generally, in use, the initial upper base putty 312 is mixed with the initial upper catalyst putty 314 to form a putty mixture. The putty mixture is then positioned in the initial upper dental tray 310 to form a dental impression of the upper teeth.

Figure 14:
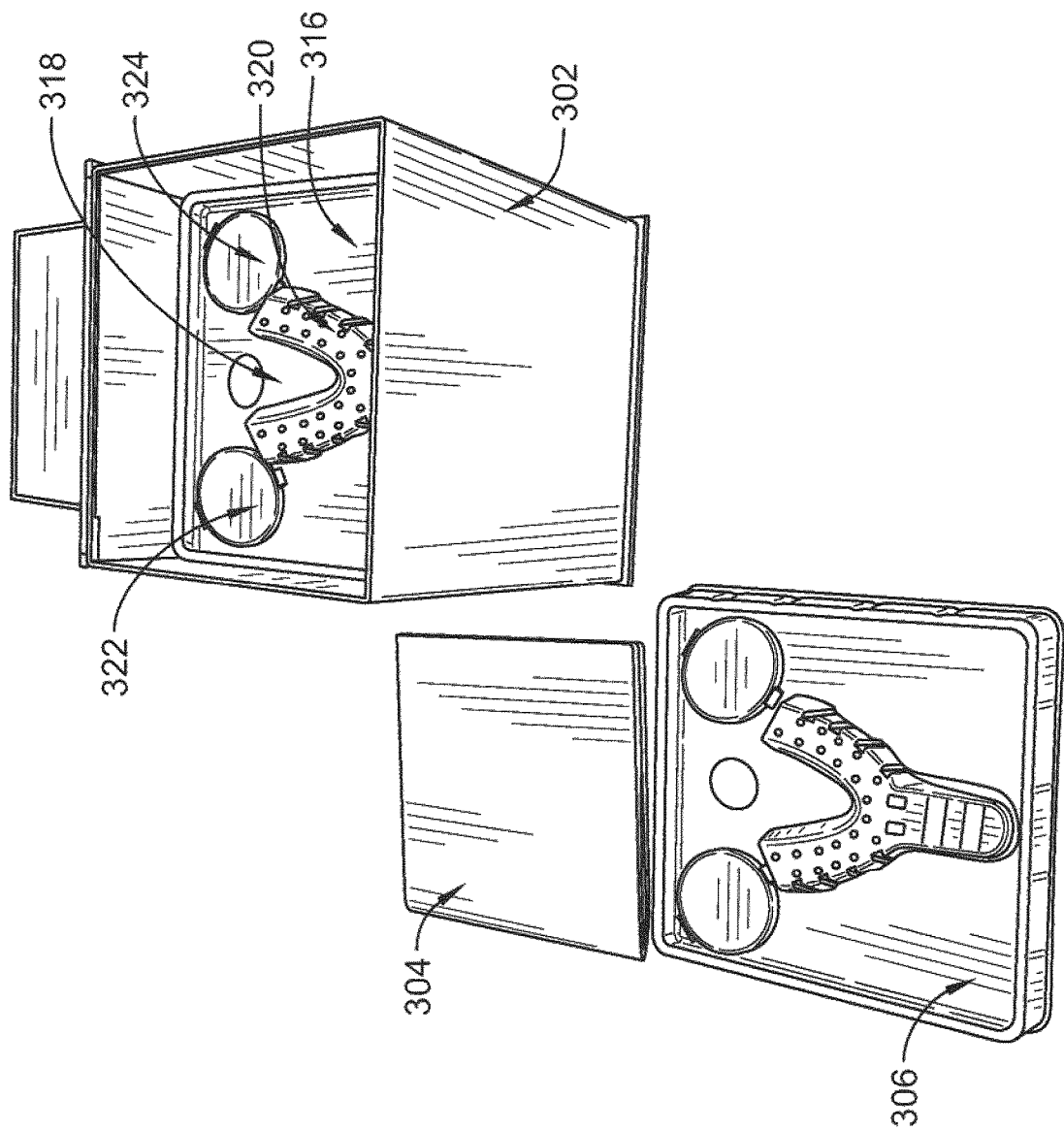
FIG. 14 is a perspective view of another initial dental assembly insert that is positioned within the container shown in FIG. 11.

Referring to FIG. 14, when the insert 306 is removed, another insert 316 is exposed that includes the contents of an initial lower dental assembly 318. The initial lower dental assembly 318 includes an initial lower dental tray 320, a container of an initial lower base putty 322, and a container of an initial lower catalyst putty 324. The instruction manual 304 includes initial instructions for administering the initial lower dental assembly 318. Generally, in use, the initial lower base putty 322 is mixed with the initial lower catalyst putty 324 to form a putty mixture. The putty mixture is then positioned in the initial lower dental tray 320 to form a dental impression of the lower teeth.

Figure 15:
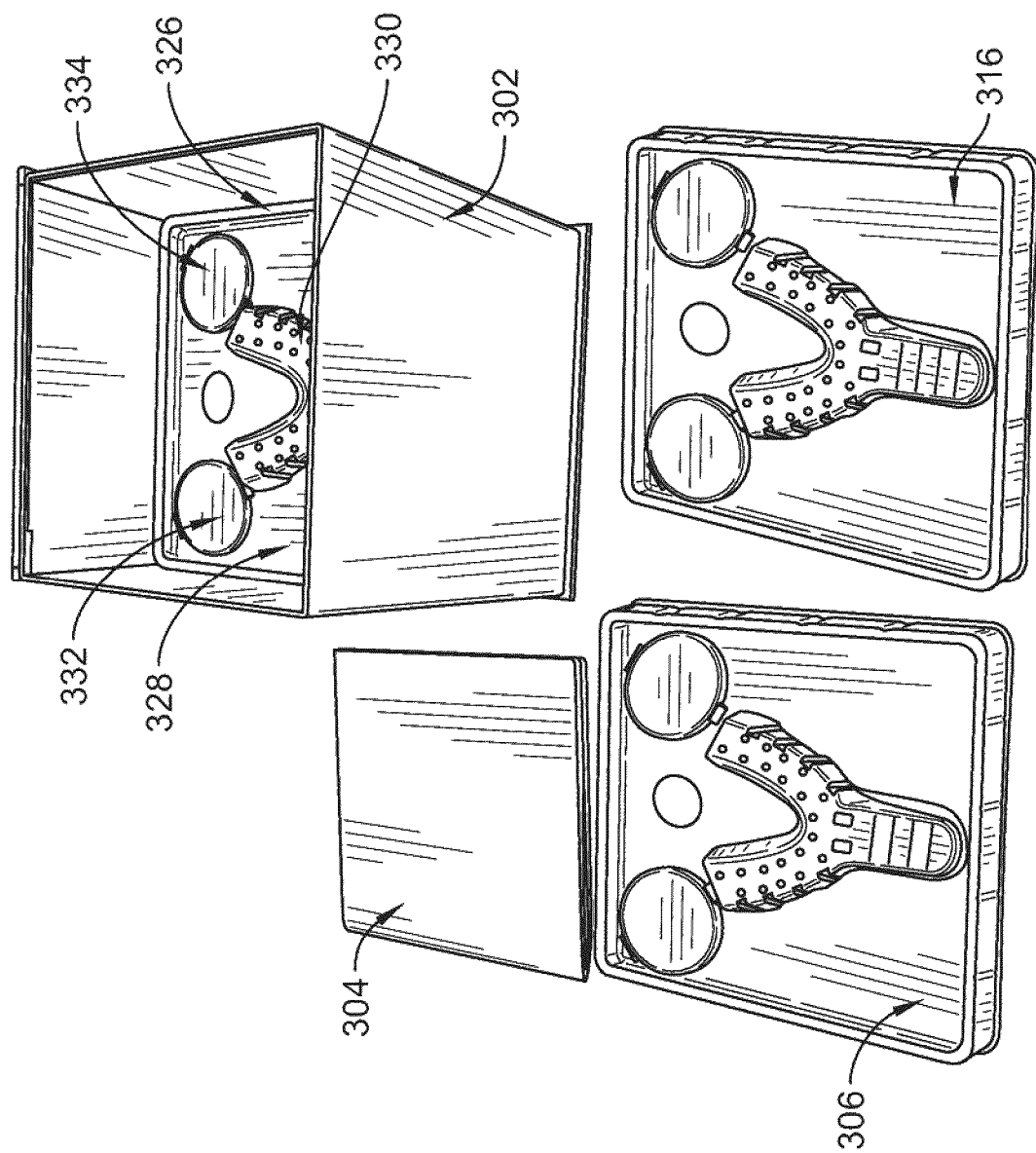
FIG. 15 is a perspective view of a redundant dental assembly insert that is positioned within the container shown in FIG. 11.

Referring to FIG. 15, when the insert 316 is removed from the box 302, an insert 326 is exposed that includes the contents of a redundant upper dental assembly 328. The redundant upper dental assembly 328 includes a redundant upper dental tray 330, a container of a redundant upper base putty 332, and a container of a redundant upper catalyst putty 334. The instruction manual 304 includes redundant instructions for administering the redundant upper dental assembly 328. Generally, in use, the redundant upper base putty 332 is mixed with the redundant upper catalyst putty 334 to form a putty mixture. The putty mixture is then positioned in the redundant upper dental tray 330 to form a dental impression of the upper teeth.

Figure 16:
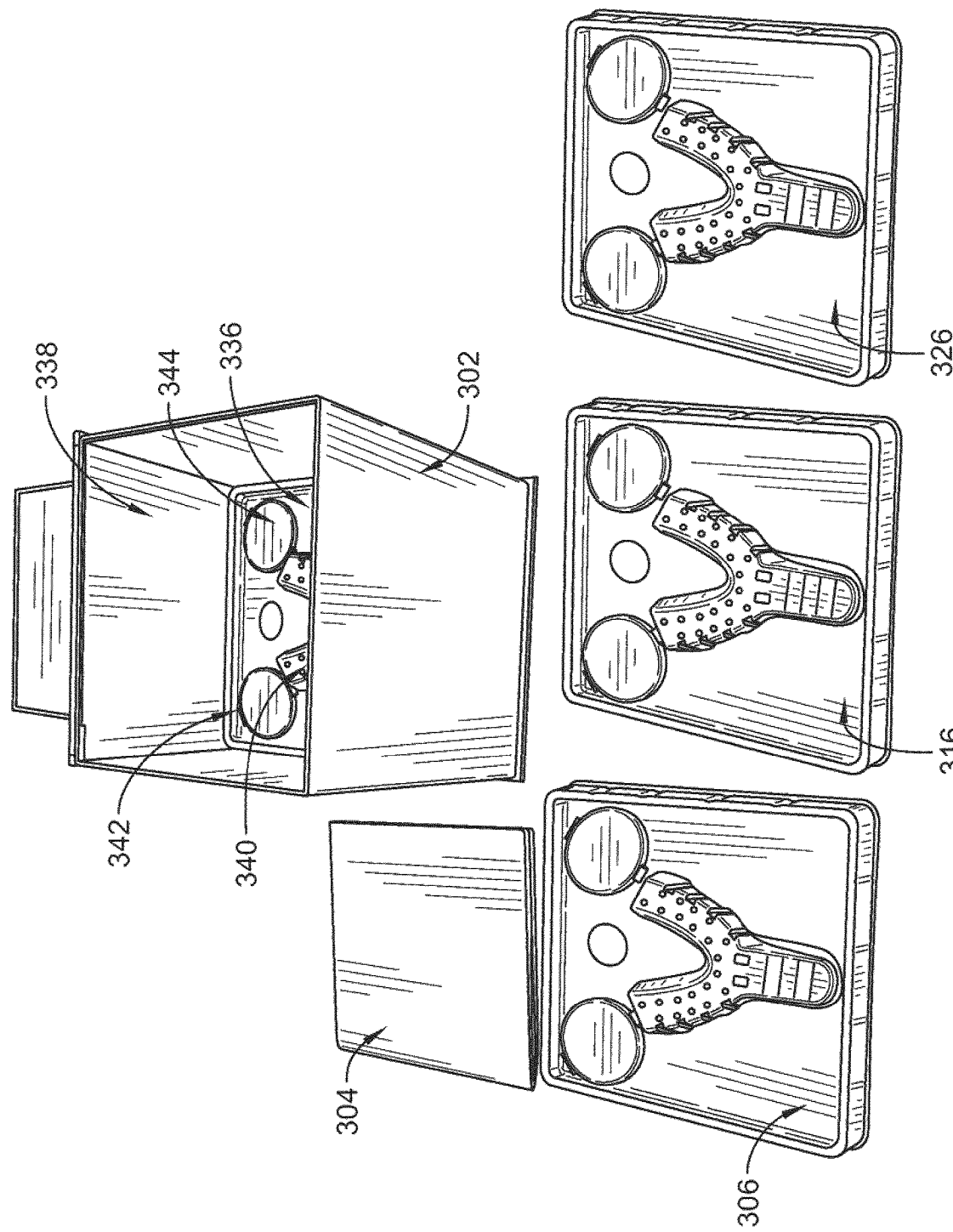
FIG. 16 is a perspective view of another redundant dental assembly insert that is positioned within the container shown in FIG. 11.

Referring to FIG. 16, when the insert 326 is removed, another insert 336 is exposed that includes the contents of a redundant lower dental assembly 338. The redundant lower dental assembly 338 includes a redundant lower dental tray 340, a container of a redundant lower base putty 342, and a container of a redundant lower catalyst putty 344. The instruction manual 304 includes redundant instructions for administering the redundant lower dental assembly 338. Generally, in use, the redundant lower base putty 342 is mixed with the redundant lower catalyst putty 344 to form a putty mixture. The putty mixture is then positioned in the redundant lower dental tray 340 to form a dental impression of the lower teeth.

Figure 17:
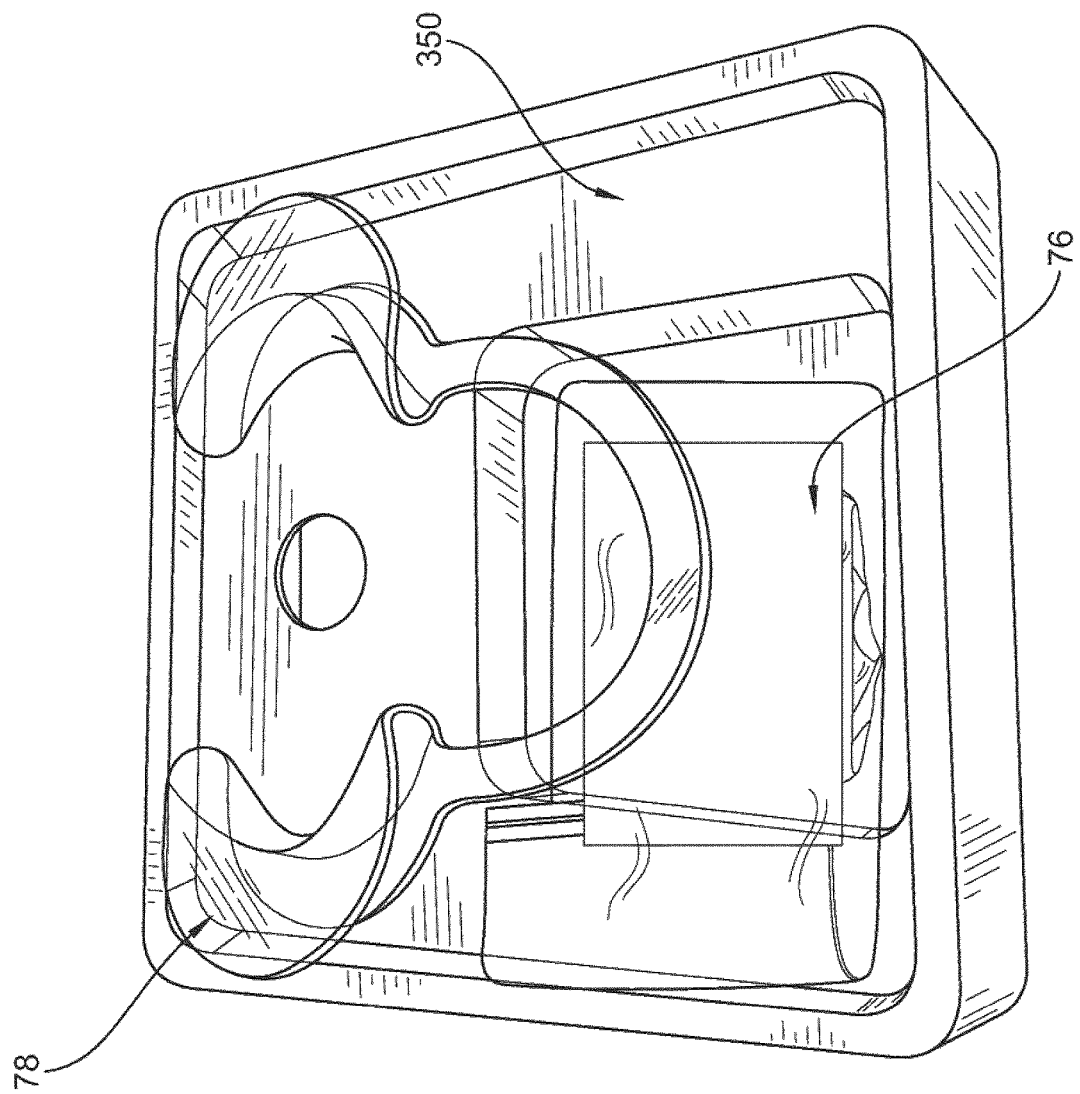
FIG. 17 is a perspective view of a dental appliance insert that is positioned within the container shown in FIG. 11.

Referring to FIG. 17, another insert 350 includes a pair of gloves 76 and a dental appliance 78. The insert 350 is positioned below the insert 336. When opening the dental impression kit 10, the user may first remove the instruction manual 54 and the inserts 306, 316, 326, and 336 to gain access to the pair of gloves 76 and the dental appliance 78.

The inserts 306, 316, 326, and 336 may then be positioned back into the box so that the user may appropriately follow the instructions in the instruction manual 54, as described in more detail below.

Figure 18:
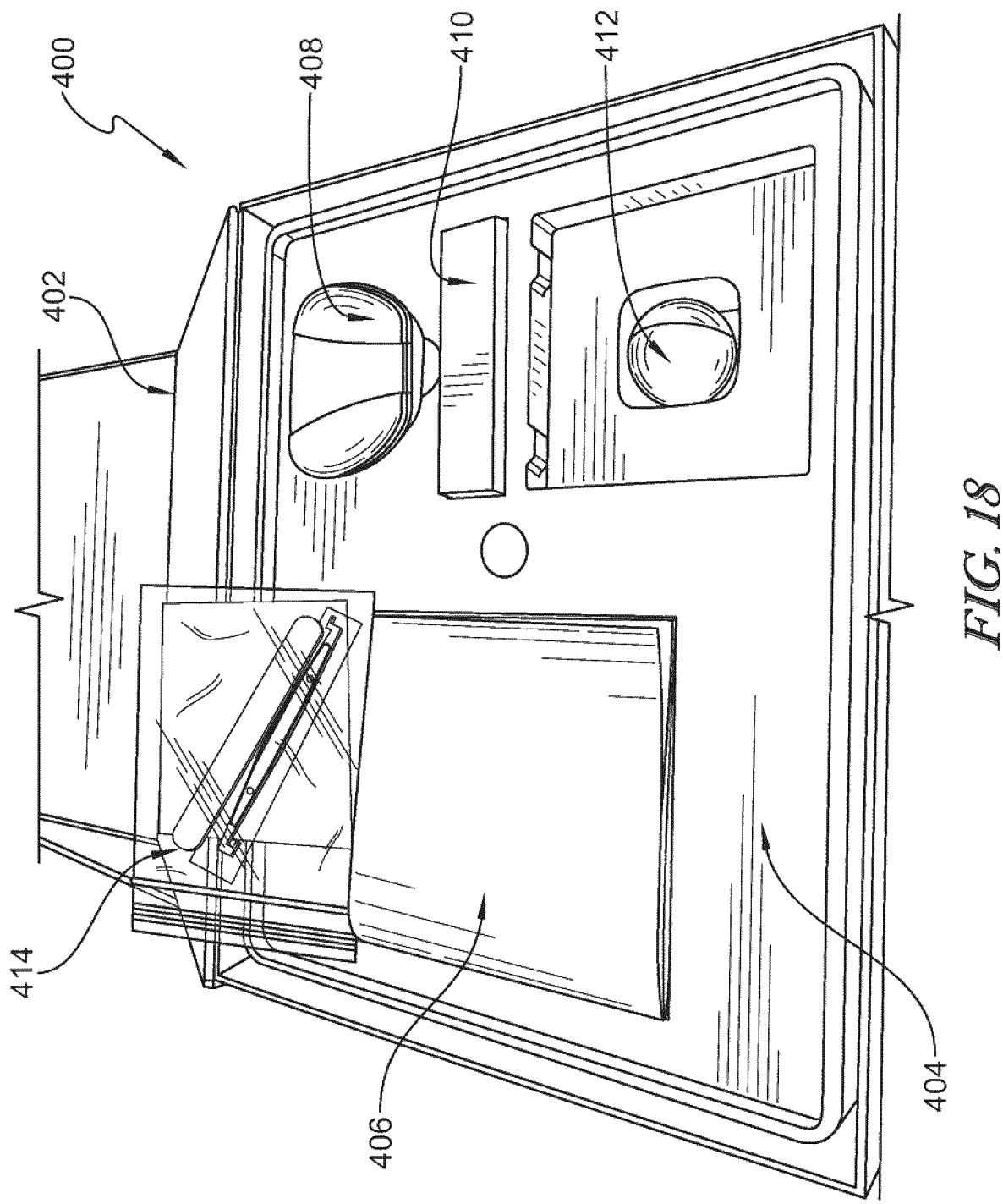
FIG. 18 is a perspective view of a dental aligner kit having a top insert.

Referring to FIG. 18, an alignment kit 400 is mailed to the user after the user specific aligners have been created by the vendor. The alignment kit 400 includes a container 402 having a top insert 404. The top insert 404 includes an instruction manual 406 that provides instructions for administering the alignment kit 400. The top insert 404 also includes a case 408 for retaining aligners (described below), a case of tooth whitening 410 to be used with the aligners, and lip balm 412. A tool kit 414 is also provided in the top insert 404.

Figure 19:
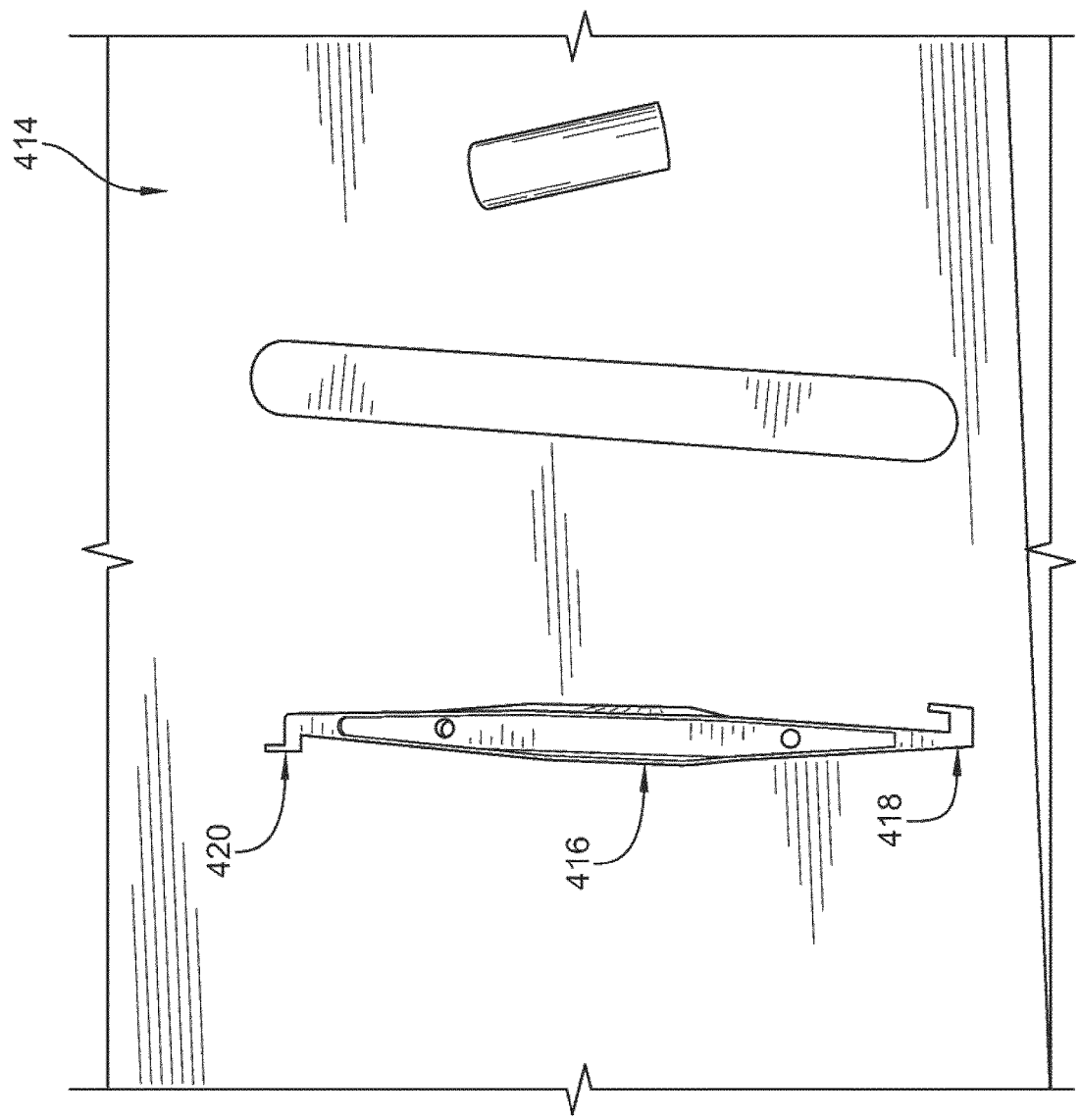
FIG. 19 is a plan view of a dental tool kit of the dental aligner kit shown in FIG. 18.

Referring to FIG. 19, the tool kit 414 includes an extractor 416 for removing aligners from the user's mouth. The extractor 416 includes a first hook 418 for pulling upper aligners off of the user's upper teeth. A second hook 420 pushes lower aligners off the user's lower teeth. The tool kit 414 also includes a file 422 for smoothing out edges of the aligners for the user's comfort. At least one rubber pellet 424 is also provided for aiding the insertion of the aligners. When the user positions the aligner's in his/her mouth, the user may chew on the rubber pellets 424 to push the aligners into position on the user's upper and lower teeth.

Figure 20:
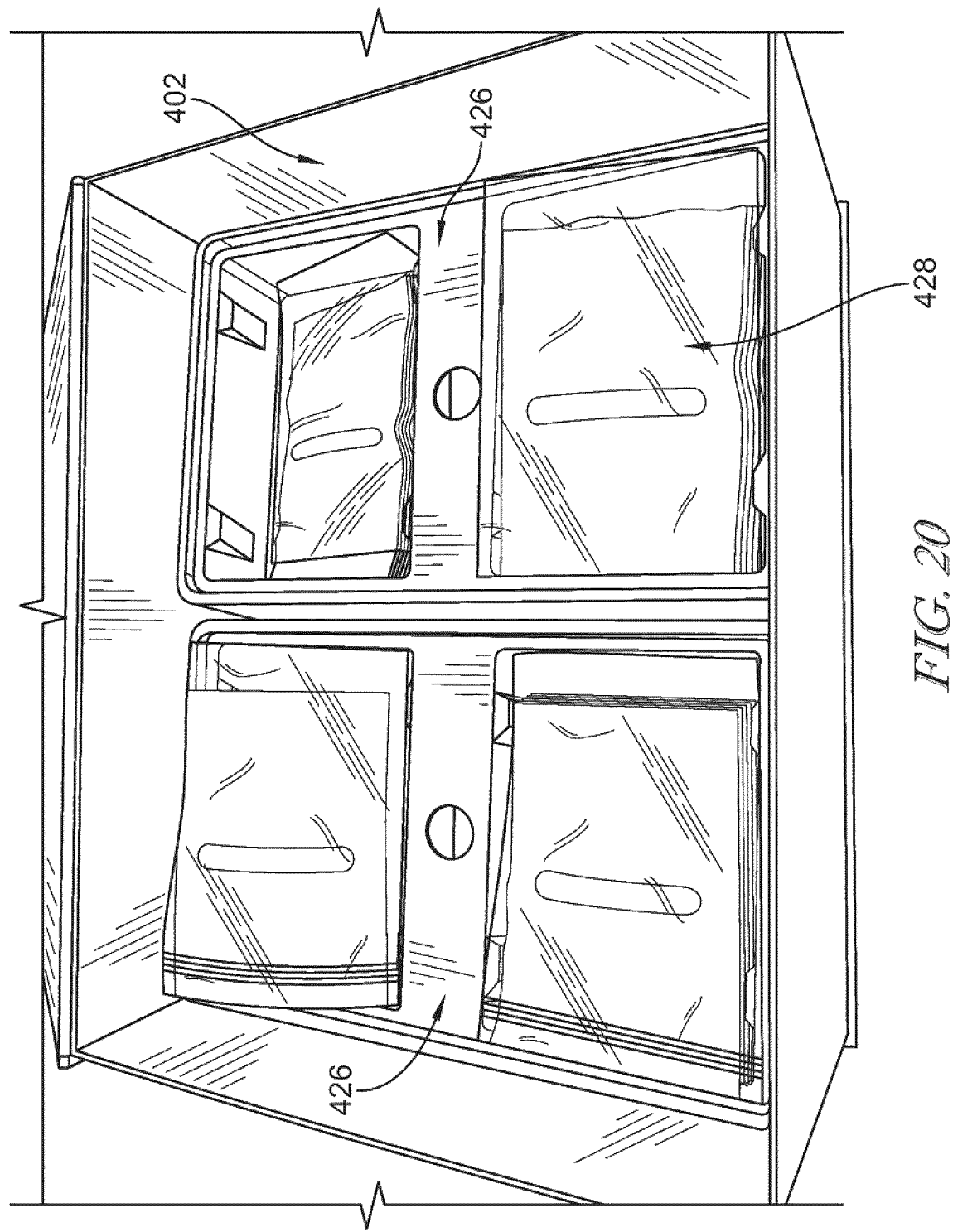
FIG. 20 is a perspective view of first lower inserts of the dental aligner kit shown in FIG. 18.
Figure 21:
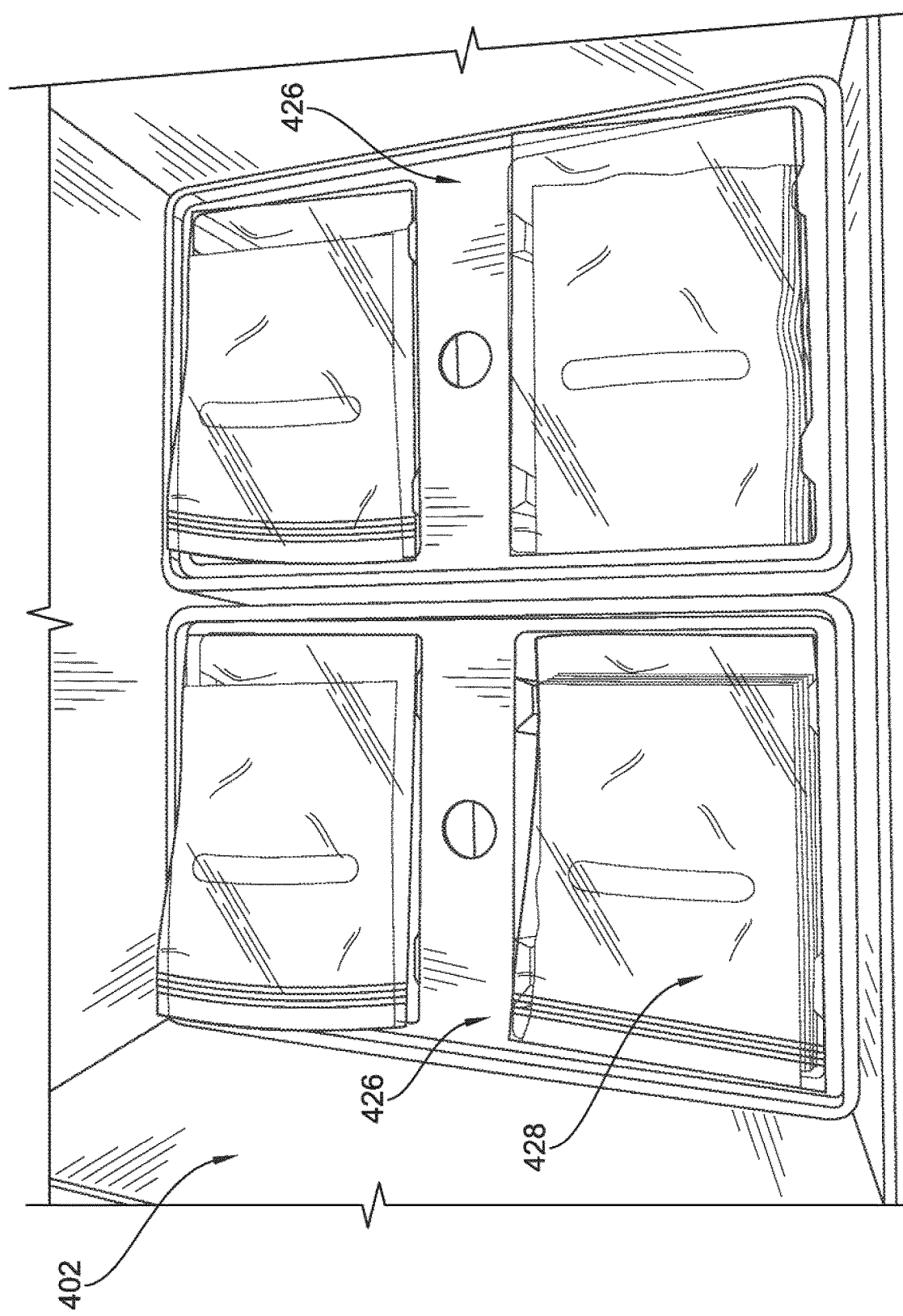
FIG. 21 is a perspective view of second lower inserts of the dental aligner kit shown in FIG. 18.

Referring to FIG. 20, when the top insert 404 is removed from the container 402, at least two lower inserts 426 are exposed. The lower inserts 426 include the aligners 428 that will be inserted in the user's mouth. Referring to FIG. 21, the additional lower inserts 426 may be positioned below the first layer of lower inserts 426.

Figure 22:
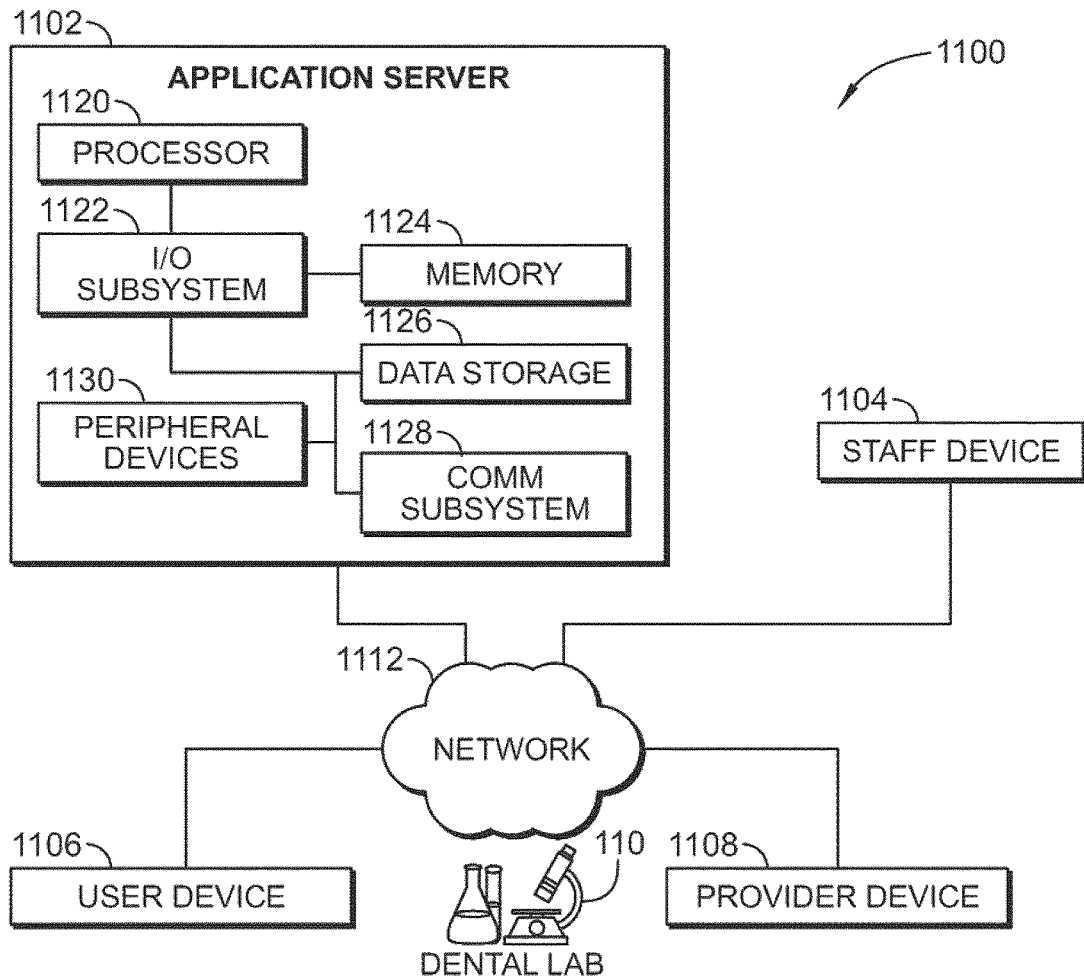
FIG. 22 is a simplified block diagram of at least one embodiment of a system for remote orthodontic treatment and assessment.

Referring now to FIG. 22, in an illustrative embodiment, a system 1100 for remote orthodontic assessment and treatment includes an application server 1102 in communication over a network 1112 with multiple other computing devices, such as one or more staff devices 1104, user devices 1106, provider devices 1108, and/or dental labs 1110. In use, as described further below, the application server 1102 allows a user (using a user device 1106) to order a dental impression kit 10, as described above, and then upload images of the user's mouth and teeth to the application server 1102. The application server 1102 allows a staff professional/hygienist to review and approve the images using the staff device 1104, and then allows a provider (e.g., an orthodontist) to perform a photo assessment using the provider device 1108. After the photo assessment is approved, the application server 1102 receives a 3D treatment plan from the dental lab 1110, and the application server 1102 allows the provider to approve the treatment plan using the provider device 1108. After approval, the application server 1102 allows the user to view the 3D treatment plan using the user device 1106. The application server 1102 optimizes the 3D treatment plan for viewing on the user device 1106. Thus, the system 1100 may allow for remote orthodontic treatment and assessment, without requiring the user to visit the provider's physical offices. Accordingly, the system 1100 may improve the cost and/or availability of orthodontic services. Additionally, by optimizing the 3D treatment plan, the system 1100 provides an improved user experience for viewing treatment plans without the aid of an orthodontist.

The application server 1102 may be embodied as any type of computation or computer device capable of performing the functions described herein, including, without limitation, a computer, a server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. As such, the application server 1102 may be embodied as a single server computing device or a collection of servers and associated devices. For example, in some embodiments, the application server 1102 may be embodied as a "virtual server" formed from multiple computing devices distributed across the network 1112 and operating in a public or private cloud. Accordingly, although the application server 1102 is illustrated in FIG. 1 and described below as embodied as a single server computing device, it should be appreciated that the application server 1102 may be embodied as multiple devices cooperating together to facilitate the functionality described below. As shown in FIG. 1, the application server 1102 illustratively include a processor 1120, an input/output subsystem 1122, a memory 1124, a data storage device 1126, and a communication subsystem 1128, and/or other components and devices commonly found in a server computer or similar computing device. Of course, the application server 1102 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 1124, or portions thereof, may be incorporated in the processor 1120 in some embodiments.

The processor 1120 may be embodied as any type of processor capable of performing the functions described herein. The processor 1120 may be embodied as a single or multi-core processor(s), digital signal processor, microcontroller, or other processor or processing/controlling circuit. Similarly, the memory 1124 may be embodied as any type of volatile or non-volatile memory or data storage capable of performing the functions described herein. In operation, the memory 1124 may store various data and software used during operation of the application server 1102, such as operating systems, applications, programs, libraries, and drivers. The memory 1124 is communicatively coupled to the processor 1120 via the I/O subsystem 1122, which may be embodied as circuitry and/or components to facilitate input/output operations with the processor 1120, the memory 1124, and other components of the application server 1102. For example, the I/O subsystem 1122 may be embodied as, or otherwise include, memory controller hubs, input/output control hubs, platform controller hubs, integrated control circuitry, firmware devices, communication links (i.e., point-to-point links, bus links, wires, cables, light guides, printed circuit board traces, etc.) and/or other components and subsystems to facilitate the input/output operations. In some embodiments, the I/O subsystem 1122 may form a portion of a system-on-a-chip (SoC) and be incorporated, along with the processor 1120, the memory 1124, and other components of the application server 1102, on a single integrated circuit chip.

The data storage device 1126 may be embodied as any type of device or devices configured for short-term or long-term storage of data such as, for example, memory devices and circuits, memory cards, hard disk drives, solid-state drives, or other data storage devices. The communication subsystem 1128 of the application server 1102 may be embodied as any communication circuit, device, or collection thereof, capable of enabling communications between the application server 1102 and other remote devices over a network. The communication subsystem 1128 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the application server 1102 may also include one or more peripheral devices 1130. The peripheral devices 1130 may include any number of additional input/output devices, interface devices, and/or other peripheral devices. For example, in some embodiments, the peripheral devices 1130 may include a display, touch screen, graphics circuitry, keyboard, mouse, speaker system, microphone, network interface, and/or other input/output devices, interface devices, and/or peripheral devices.

As described further below, the staff device 1104 is configured to upload, review, and otherwise manage data stored by the application server 1102. The staff device 1104 may be embodied as any type of device capable of performing the functions described herein, such as, without limitation, a smartphone, a cellular phone, a tablet computer, a notebook computer, a laptop computer, a desktop computer, a consumer electronic device, a wearable computing device, a smart appliance, and/or any other computing device capable of performing the functions described herein. Accordingly, the staff device 1104 may include a processor, an I/O subsystem, a memory, a data storage device, communication circuitry, and/or other components and devices commonly found in a notebook computer or similar computing device. The individual components of the staff device 1104 may be similar to the corresponding components of the application server 1102, the description of which is applicable to the corresponding components of the staff device 1104 and is not repeated herein so as not to obscure the present disclosure.

As described further below, the user device 1106 is configured to allow a user to send and receive images, questionnaire responses, and other data with the application server 1102. The user device 1106 may be embodied as any type of device capable of performing the functions described herein, such as, without limitation, a smartphone, a cellular phone, a tablet computer, a notebook computer, a laptop computer, a desktop computer, a consumer electronic device, a wearable computing device, a smart appliance, and/or any other computing device capable of performing the functions described herein. Accordingly, the user device 1106 may include a processor, an I/O subsystem, a memory, a data storage device, communication circuitry, and/or other components and devices commonly found in a smartphone or similar computing device. The individual components of the user device 1106 may be similar to the corresponding components of the application server 1102, the description of which is applicable to the corresponding components of the user device 1106 and is not repeated herein so as not to obscure the present disclosure.

As described further below, the provider device 1108 is configured to allow a provider to review image assessments and treatment plans and to otherwise access the application server 1102. The provider device 1108 may be embodied as any type of device capable of performing the functions described herein, such as, without limitation, a smartphone, a cellular phone, a tablet computer, a notebook computer, a laptop computer, a desktop computer, a consumer electronic device, a wearable computing device, a smart appliance, and/or any other computing device capable of performing the functions described herein. Accordingly, the provider device 1108 may include a processor, an I/O subsystem, a memory, a data storage device, communication circuitry, and/or other components and devices commonly found in a notebook computer or similar computing device. The individual components of the provider device 1108 may be similar to the corresponding components of the application server 1102, the description of which is applicable to the corresponding components of the provider device 1108 and is not repeated herein so as not to obscure the present disclosure.

The dental lab 1110 may be embodied as any dental analysis and/or manufacturing facility that is capable of generating orthodontic treatment plans or otherwise performing the functions described herein. In particular, the dental lab 1110 may include or otherwise have access to one or more computing devices capable of executing software to generate orthodontic treatment plans.

As discussed in more detail below, the application server 1102, the staff device 1104, the user device 1106, and the provider device 1108 may be configured to transmit and receive data with each other and/or other devices of the system 1100 over the network 1112. The network 1112 may be embodied as any number of various wired and/or wireless networks. For example, the network 1112 may be embodied as, or otherwise include, a wired or wireless local area network (LAN), and/or a wired or wireless wide area network (WAN). As such, the network 1112 may include any number of additional devices, such as additional computers, routers, and switches, to facilitate communications among the devices of the system 1100. In the illustrative embodiment, the network 1112 is embodied as a local Ethernet network.

Figure 23:
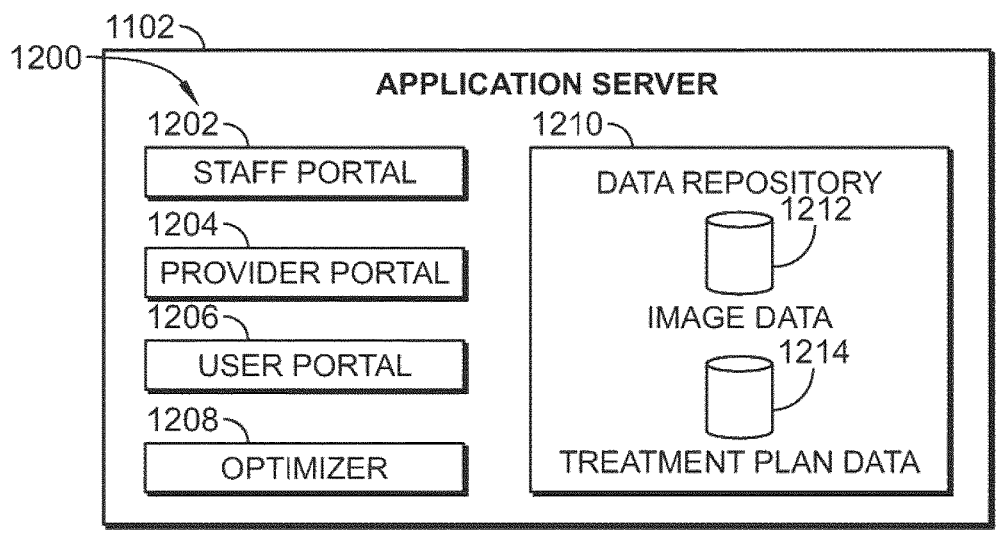
FIG. 23 is a simplified block diagram of at least one embodiment of an environment that may be established by an application server of FIG. 22.

Referring now to FIG. 23, in an illustrative embodiment, the application server 1102 establishes an environment 1200 during operation. The illustrative environment 1200 includes a staff portal 1202, a provider portal 1204, a user portal 1206, an optimizer 1208, and a data repository 1210. The various components of the environment 1200 may be embodied as hardware, firmware, software, or a combination thereof. As such, in some embodiments, one or more of the components of the environment 1200 may be embodied as circuitry or collection of electrical devices (e.g., staff portal circuitry 1202, provider portal circuitry 1204, user portal circuitry 1206, optimizer circuitry 1208, and/or data repository circuitry 1210). It should be appreciated that, in such embodiments, one or more of the staff portal circuitry 1202, the provider portal circuitry 1204, the user portal circuitry 1206, the optimizer circuitry 1208, and/or the data repository circuitry 1210 may form a portion of one or more of the processor 1120, the I/O subsystem 1122, and/or other components of the application server 1102. Additionally, in some embodiments, one or more of the illustrative components may form a portion of another component and/or one or more of the illustrative components may be independent of one another.

The data repository 1210 is configured to manage and store case data related to each user. The data repository 1210 may be configured to receive multiple images that represent the teeth of a user. The data repository 1210 may be further configured to receive a treatment plan for the user. The treatment plan may include a sequence of three-dimensional models indicative of the teeth of the user. Thus, the data repository 1210 may store, among other data, image data 1212 and/or treatment plan data 1214.

The staff portal 1202 is configured to manage data access and other communications with the staff devices 1104. In particular, the staff portal 1202 may be configured to provide the images that represent the teeth of the user to a staff device 1104. The staff portal 1202 is further configured to receive an approval from the staff device 1104 indicating that a person (e.g., a staff professional person and/or hygienist) has approved the images for assessment by a provider (e.g., an orthodontist).

The provider portal 1204 is configured to manage data access and other communications with the provider devices 1108. In particular, the provider portal 1204 may be configured to provide the images to a provider device 1108 in response receiving the approval from the staff device 1104. The provider portal 1204 may be further configured to receive an approval from the provider device 1108 indicating that the provider successfully performed an assessment of the fitness of the user for treatment. A treatment plan may be received in response to that approval, and the provider portal 1204 may be further configured to provide the treatment plan to the provider device 1108 and to receive an approval from the provider device 1108 indicating that the provider approved the treatment plan.

The user portal 1206 is configured to manage data access and other communications with the user devices 1106. In particular, the user portal 1206 may be configured to receive the images indicative of the teeth of the user from a user device 1106. In some embodiments, the images may include an upper, open view image, a lower, open view image, and a straight-on, closed view image. The user portal 1206 may be further configured to receive a dental history questionnaire response from the user device 1106. The dental history questionnaire response may be included with the images to the staff device 1104 and/or to the provider device 1108. The user portal 1206 is further configured to provide a visualization of the treatment plan to the user device 1106 in response to receiving approval of the treatment plan from the provider device 1108.

The optimizer 1208 is configured to optimize the sequence of three-dimensional models to generate an optimized sequence of three-dimensional models. The visualization of the treatment plan may use the optimized sequence of three-dimensional models.

Figure 24A:
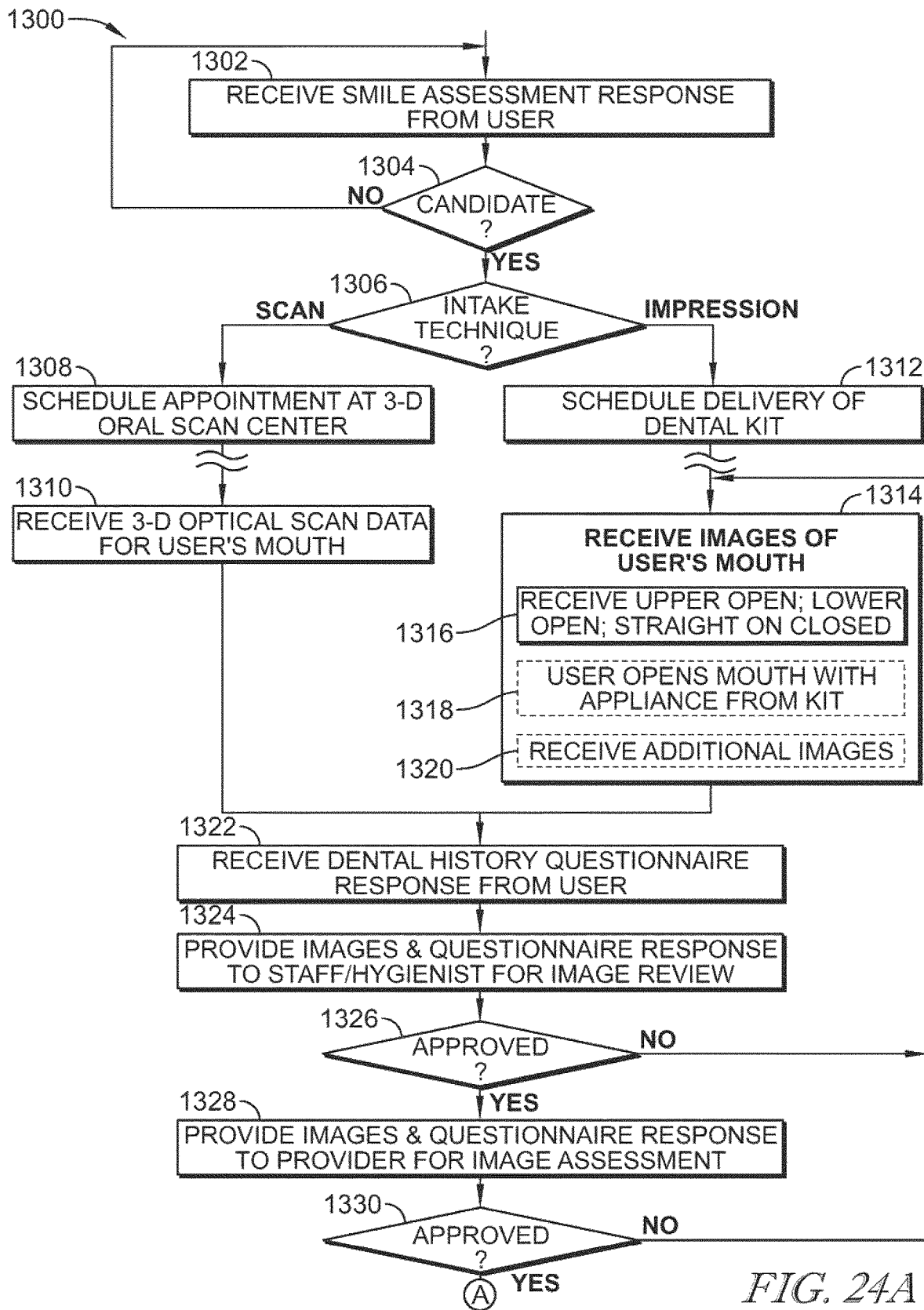
FIGS. 24A and 24B are a simplified flow diagram of at least one embodiment of a method for remote orthodontic treatment and assessment that may be executed by the application server of FIGS. 22-23.
Figure 24B:
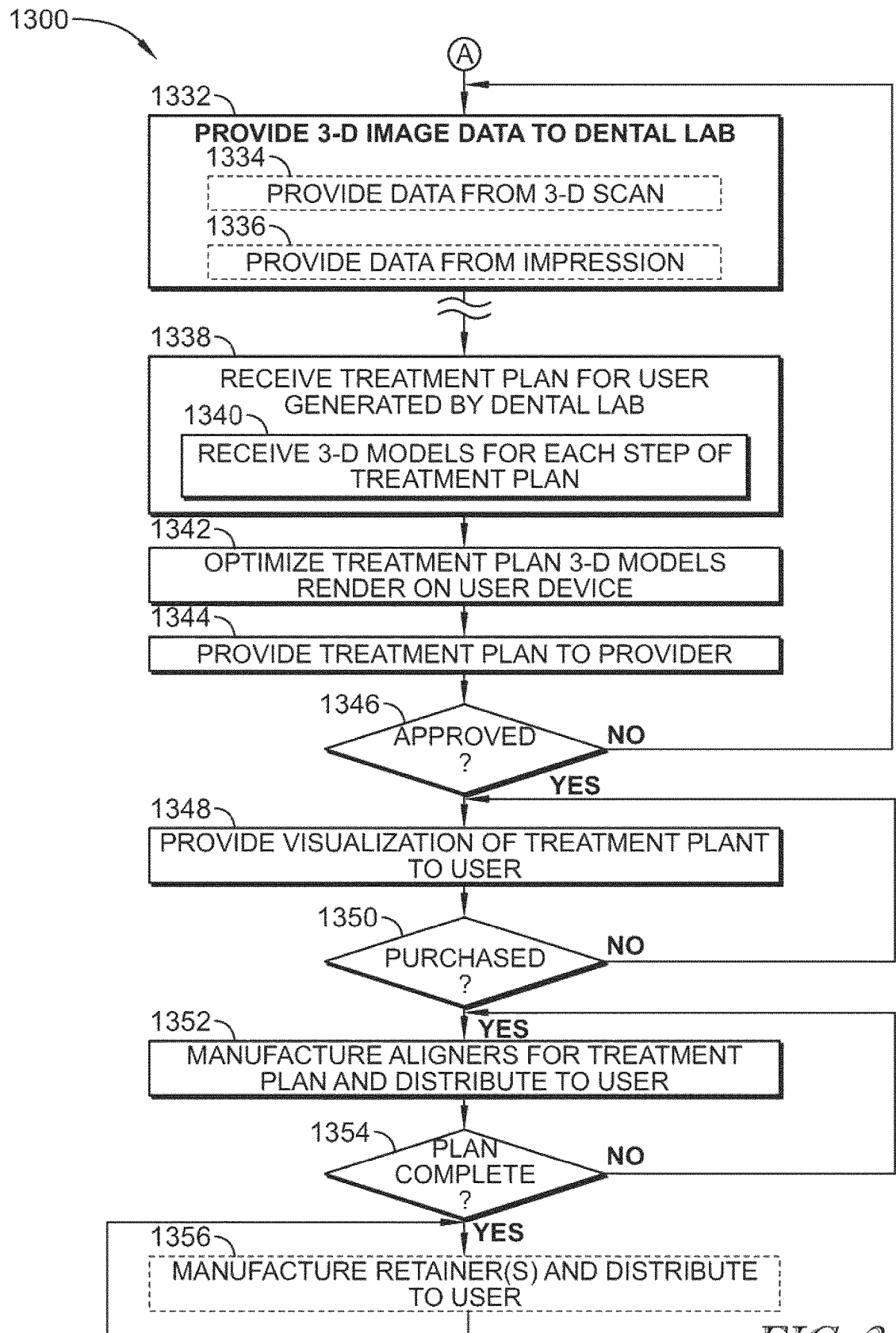

Referring now to FIGS. 24A and 24B, in use, the application server 1102 may execute a method 1300 for remote orthodontic treatment and assessment. It should be appreciated that, in some embodiments, the operations of the method 1300 may be performed by one or more components of the environment 1200 of the application server 1102 as shown in FIG. 23. The method 1300 begins in block 1302, in which the application server 1102 receives a smile assessment response from a user device 1106. The smile assessment response may be embodied as a web form, electronic message, or other data submitted by the user device 1106 that is indicative of whether the user is a potential candidate for orthodontic treatment. For example, the smile assessment response may include answers to questions indicating the current condition of the user's mouth and the user's chief complaint (i.e., the user's biggest concern with his or her smile). The smile assessment response may be submitted in response to a web form or other web page that includes appropriate questions and instructions. One potential embodiment of a smile assessment web page is described below in connection with FIG. 26. After receiving the smile assessment response, in block 1304 the application server 1102 determines whether the user is a potential candidate for orthodontic treatment based on the smile assessment response. If the application server 1102 determines that the user is not a good candidate, the method 1300 loops back to block 1302, in which the application server 1102 may receive additional smile assessment responses from the same user device 1106 and/or other user devices 1106. If the application server 1102 determines that the user is a good candidate, the method 1300 advances to block 1306.

In block 1306, the application server 1102 determines an appropriate intake technique for the user. In the illustrative embodiment, potential intake techniques include performing a three-dimensional (3D) scan of the user's teeth and mouth at an oral scan center, or delivering a dental impression kit 10, as described above. The application server 1102 may allow the user to select an intake technique using the user device 1106, for example by selecting an option from a web page. In some embodiments, the application server 1102 may determine whether the user is located near an oral scan center and, if near a scan center, present the user with the scan option. If the application server 1102 determines to use the dental impression kit 10, the method 1300 branches to block 1312, described below. If the application server 1102 determines to use the 3D scan, the method 1300 branches to block 1308.

In block 1308, the application server 1102 allows the user to schedule an appointment at a 3D oral scan center. The application server 1102 may use any technique to schedule the appointment. For example, the application server 1102 may provide a web application or other interface to the user device 1106 to allow the user to select a date and time for the appointment. The application server 1102 may store the appointment information and provide reminders to the user as appropriate. At the appointment, a professional uses a 3D camera to capture a 3D optical scan of the user's mouth. The professional may be a hygienist or other trained professional, but is typically not an orthodontist. After the 3D scan appointment, in block 1310 the application server 1102 receives 3D optical scan data for the user's mouth. The 3D optical scan data may be embodied as any data file or collection of data files that include images of the patient's mouth as well as corresponding depth or other spatial information. After receiving the 3D optical scan data, the method 1300 advances to block 1322, described below.

Referring back to block 1306, if the application server 1102 determines to use the dental impression kit 10, the method 1300 branches to block 1312, in which the application server 1102 schedules delivery of a dental impression kit 10 to the user. After the user has received the dental impression kit 10, in block 1314 the application server 1102 receives images of the user's mouth and teeth. The user device 1106 may upload the images to the application server 1102, for example, through a web interface. In some embodiments, the application server 1102 may establish an account for the user. The application server 1102 may present the user with an account status user interface that provides access to an interface for uploading images. Images may be updated at any time after the account is created, for example after purchasing the dental impression kit 10, during use of the dental impression kit 10, and/or after creating a scan appointment. One potential embodiment of an account status user interface is described below in connection with FIG. 27. As part of the image upload web interface, the application server 1102 may provide instructions to the user on which views to capture and upload, and in some embodiments may provide tips to improve image quality. For example, the instructions may recommend that the user has another person assist in taking the images and/or may recommend using a flash or a bright light source such as a bathroom light or a window on a sunny day. As described above, the dental impression kit 10 may also include an instruction manual 54 that includes similar instructions and/or tips. In block 1316, the application server 1102 receives images for three views of the user's mouth: a view of the upper teeth with the mouth open, a view of the lower teeth with the mouth open, and a view of the teeth from straight on with the mouth closed. One potential embodiment of a web interface to provide instructions to the user and to upload images is described further below in connection with FIGS. 27A-27C. In some embodiments, in block 1318 the user may use the dental appliance 78 to separate the user's lips and open the user's mouth while taking the images, as described above. In some embodiments, in block 1320 the application server 1102 may receive additional images of the user's mouth and teeth, such as an upper, closed view; a left side, closed view; a right side, closed view; and/or a straight-on, full-smile view. As described further below, the additional images may be requested by a staff professional, a hygienist, and/or a provider while performing an image assessment. For example, the additional images may be requested for complicated cases. After receiving the images, the method 1300 advances to block 1322.

In block 1322, the application server 1102 receives a dental history questionnaire response from the user device 1106. The dental history questionnaire response may be embodied as any web form, electronic message, or other data submitted by the user device 1106. The dental history questionnaire response may include information related to the user's dental history that may be used by a staff professional, hygienist, and/or provider to determine the user's fitness for treatment. One potential embodiment of a dental history questionnaire is described below in connection with FIGS. 28A-28E.

In block 1324, the application server 1102 provides images of the user's mouth and teeth as well as the dental history questionnaire response to a staff professional and/or hygienist for review and approval. For example, the application server 1102 may establish a staff portal web site that is accessible by the staff device 1104. Because the images of the user's mouth and teeth and the dental history questionnaire response may include personal health information, the application server 1102 may restrict access to the staff portal or other user interfaces to authorized users (e.g., authorized staff professionals and/or hygienists). The staff professional/hygienist may review the images and questionnaire data to determine whether the images are sufficient to allow the provider to determine the user's fitness for treatment. For example, the staff professional/hygienist may determine whether each of the images are of the correct view and/or are of sufficient quality. The staff professional/hygienist may indicate whether each image is approved and may also request that the user provide additional views or other images. One potential embodiment of a web interface provided by the application server 1102 to perform the image review is described below in connection with FIGS. 29A and 29B. In block 1326, the application server 1102 determines whether the staff professional/hygienist approved the images. If not, the method 1300 may loop back to block 1314, in which the application server 1102 receives additional images from the user device 1106. If the staff professional/hygienist approved the images, the method 1300 advances to block 1328.

In block 1328, the application server 1102 provides images of the user's mouth and teeth as well as the dental history questionnaire response to a provider for assessment and approval. For example, the application server 1102 may establish a provider portal web site that is accessible by the provider device 1108. Because the images of the user's mouth and teeth and the dental history questionnaire response may include personal health information, the application server 1102 may restrict access to the provider portal or other user interfaces to authorized users (e.g., authorized providers). The provider may review the images and questionnaire data to determine the user's fitness for treatment. For example, the provider may determine whether the user's mouth and/or desired treatment outcome are fit for treatment with invisible plastic aligners. Continuing that example, the user may not be fit for treatment, for example, if the user's mouth and/or desired treatment outcome requires pulling teeth, interproximal reduction, or performing other procedures that cannot be achieved with aligners. To perform the assessment, the provider may access a provider portal with a web interface similar to the web interface shown in FIGS. 29A and 29B. Features of the provider portal are also described below in connection with FIGS. 30A-30E. In block 1330, the application server 1102 determines whether the provider approved the images. If not, the method 1300 may loop back to block 1314, in which the application server 1102 receives additional images from the user device 1106. If the provider approved the images, the method 1300 advances to block 1332, shown in FIG. 24B.

Referring now to FIG. 24B, in block 1332 the application server 1102 provides 3D image data for the user's mouth to the dental lab 1110. The application server 1102 may use any technique to provide the data, for example by transferring data over the network 1112 to a server or other computing device of the dental lab 1110. The 3D image data may be generated using any appropriate technique. In some embodiments, in block 1334 the application server 1102 provides data generated during a 3D optical scan, which was received by the application server 1102 as described above in connection with block 1310. In some embodiments, in block 1336 the application server 1102 provides data generated based on impressions created using the dental impression kit 10, which was scheduled for delivery as described above in connection with block 1312. In some embodiments, the dental impressions themselves may be provided to the dental lab 1110, and the dental lab 1110 may generate the 3D image data based on the impressions (and/or on the images provided by the user). After receiving the 3D image data, the dental lab 1110 may use typical dental software to generate a treatment plan.

After the dental lab 1110 creates the treatment plan, in block 1338 the application server 1102 receives the treatment plan generated by the dental lab 1110. The treatment plan may be embodied as any data indicative of a series of steps used to correct or otherwise modify the positions of the user's teeth. In particular, the treatment plan may represent the user's teeth and how they move through the duration of the treatment plan. The treatment plan may be directed to the user's upper teeth, lower teeth, or both upper and lower teeth. In block 1340, the application server 1102 receives a 3D model of the user's mouth and teeth for each step of the treatment plan. Thus, the treatment plan may indicate the position of the user's teeth as they are modified over the course of treatment. The 3D models of the treatment plan may be embodied as STL files, OBJ files, or any other data file that is indicative of a three-dimensional object and/or scene.

In block 1342, the application server 1102 optimizes the treatment plan 3D models to render on the user device 1106. The application server 1102 may perform optimization to reduce the size of corresponding data files or to otherwise improve rendering performance on the user device 1106. One potential embodiment of a method for optimizing the treatment plan 3D models is described below in connection with FIG. 25.

After optimizing the treatment plan 3D models, in block 1344 the application server 1102 provides the treatment plan to the provider for approval. For example, the application server 1102 may establish a provider portal web site that is accessible by the provider device 1108. Because the treatment plan may include personal health information, the application server 1102 may restrict access to the provider portal or other user interfaces to authorized users (e.g., authorized providers). Using the provider portal, the provider may review 3D images of the steps of the treatment plan, and may approve the plan, reject the plan, request modifications to the plan, or otherwise review the treatment plan. One potential embodiment of a user interface for the provider portal is described below in connection with FIGS. 30A-30E. In block 1346, the application server 1102 determines whether the provider has approved the treatment plan. If not, the method 1300 loops back to block 1332, in which the dental lab 1110 may modify the treatment plan or otherwise generate a new treatment plan. If the treatment plan is approved, the method 1300 advances to block 1348.

In block 1348, the application server 1102 provides a visualization of the treatment plan to the user. For example, the application server 1102 may establish a user portal web site that is accessible by the user device 1106. Because the treatment plan may include personal health information, the application server 1102 may restrict access to the user portal or other user interfaces to the authorized user. The visualization may allow the user to view the 3D models of the user's mouth and teeth for each step of the treatment process from multiple angles. As described above in connection with block 1342, the 3D models of the treatment plan are optimized for rendering by the user device 1106, which provides the user with a responsive user interface. As described above, the application server 1102 may establish an account for the user, and an account status user interface may provide access to the treatment plan visualization user interface. One potential embodiment of an account status user interface is described below in connection with FIG. 32. One potential embodiment of a treatment plan visualization user interface is described below in connection with FIG. 33.

In block 1350, the application server 1102 determines whether the user has purchased the approved treatment plan. The user may purchase the treatment plan, for example, through an account user interface provided by the application server 1102 to the user device 1106. If the user has not purchased the approved treatment plan, the method 1300 loops back to block 1348, in which the application server 1102 may continue to provide the visualization of the treatment plan to the user. If the treatment plan is purchased, the method 1300 advances to block 1352.

In block 1352, one or more aligners are manufactured for the treatment plan and distributed to the user. Any appropriate technique may be used to manufacture and distribute the aligners. For example, the aligners may be manufactured by 3D printing physical models of the user's teeth and then molding plastic aligners using the physical models of the user's teeth. Multiple aligners may be distributed to the user each month. For example, the user may be sent three aligners each month, with the first aligner to be worn for one week, the second aligner to be worn for one week, and the third aligner to be worn for two weeks. During the manufacturing and distribution process, the application server 1102 may coordinate access to order information, the treatment, plan, and other data associated with the user. In block 1354, it is determined whether the treatment plan is complete. For example, a treatment plan may have a duration of five months. If the plan is not complete, the method 1300 loops back to block 1352 to continue manufacturing and distributing aligners. If the plan is complete, the method 1300 may advance to block 1356, in which one or more retainers may be manufactured and distributed to the user. In some embodiments, the application server 1102 may perform a check-in process after a predetermined amount of time has elapsed during treatment, for example a 90-day check in process. As part of the check-in process, the patient may answer a questionnaire and submit photos that are reviewed by a dental professional. Thus, the application server 1102 may monitor the progress of the patient during treatment. One potential embodiment of a user interface for the check-in progress is shown in FIGS. 37A-37D. The method 1300 may loop back to block 1356 to continue manufacturing and distributing retainers, or in some embodiments may be completed. It should be understood that the method 1300 illustrates techniques for remote orthodontic treatment and assessment for a single user; it should be understood that the application server 1102 may execute multiple instances of the method 1300 for multiple users.

Figure 25:
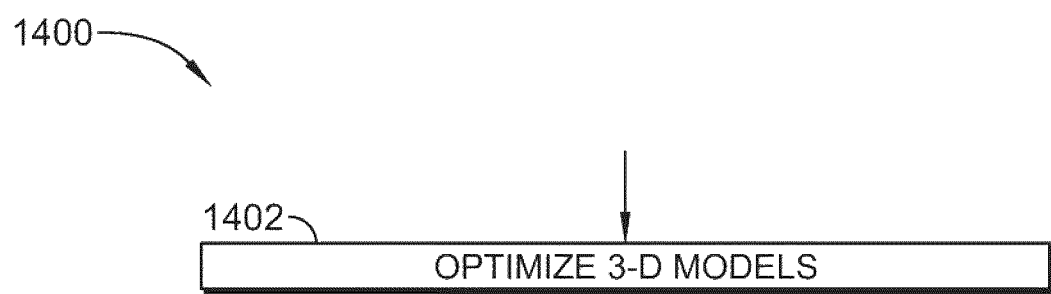
FIG. 25 is a simplified flow diagram of at least one embodiment of a method for 3D model optimization that may be executed by the application server of FIGS. 22-23.

Referring now to FIG. 25, in use, the application server 1102 may execute a method 1400 for 3D model optimization. The method 1400 may be executed, for example, in connection with block 1342 of the method 1300, described above in connection with FIG. 24B. It should be appreciated that, in some embodiments, the operations of the method 1400 may be performed by one or more components of the environment 1200 of the application server 1102 as shown in FIG. 23. The method 1400 begins in block 1402, in which the application server 1102 optimizes the 3-D models of a treatment plan.

Referring now to FIG. 26, a user interface 1500 for a smile assessment is shown. The user interface 1500 may be used to receive a smile assessment response as described above in connection with block 1302 of FIG. 24A. The illustrative user interface 1500 is a web page provided by the application server 1102 to the user device 1106; however, it should be understood that the user interface 1500 may be embodied as native application, managed application, or other interface of the user device 1106. As shown, the user interface 1500 includes multiple input elements 1502 that allow the user to provide information regarding current condition of the user's mouth and the user's chief complaint. The user interface 1500 includes a submit button 1504 that, when selected by the user, provides the smile assessment response to the application server 1102. In some embodiments, the user interface 1500 may include additional input elements 1506 (not shown) to collect additional information, such as user contact information, account information, or other information.

Referring now to FIG. 27, a user interface 1600 for account status is shown. The illustrative user interface 1600 is a web page provided by the application server 1102 to the user device 1106; however, it should be understood that the user interface 1600 may be embodied as native application, managed application, or other interface of the user device 1106. The user interface 1600 may be used to display the status of the user's account, including indicating additional information required from the user or otherwise indicating the next step to be performed by the user. For example, the illustrative user interface 1600 indicates that the user still needs to upload photos. The user interface 1600 includes a button 1602 that, when selected by the user, launches a user interface for uploading the photos. It should be understood that the user interface 1600 may include information and/or actions for other steps, such as scheduling a 3D scan appointment, reminding the user of a 3D scan appointment, indicating that images were received and are being reviewed, indicating that a treatment plan is being created, or other status information.

Figure 28A:
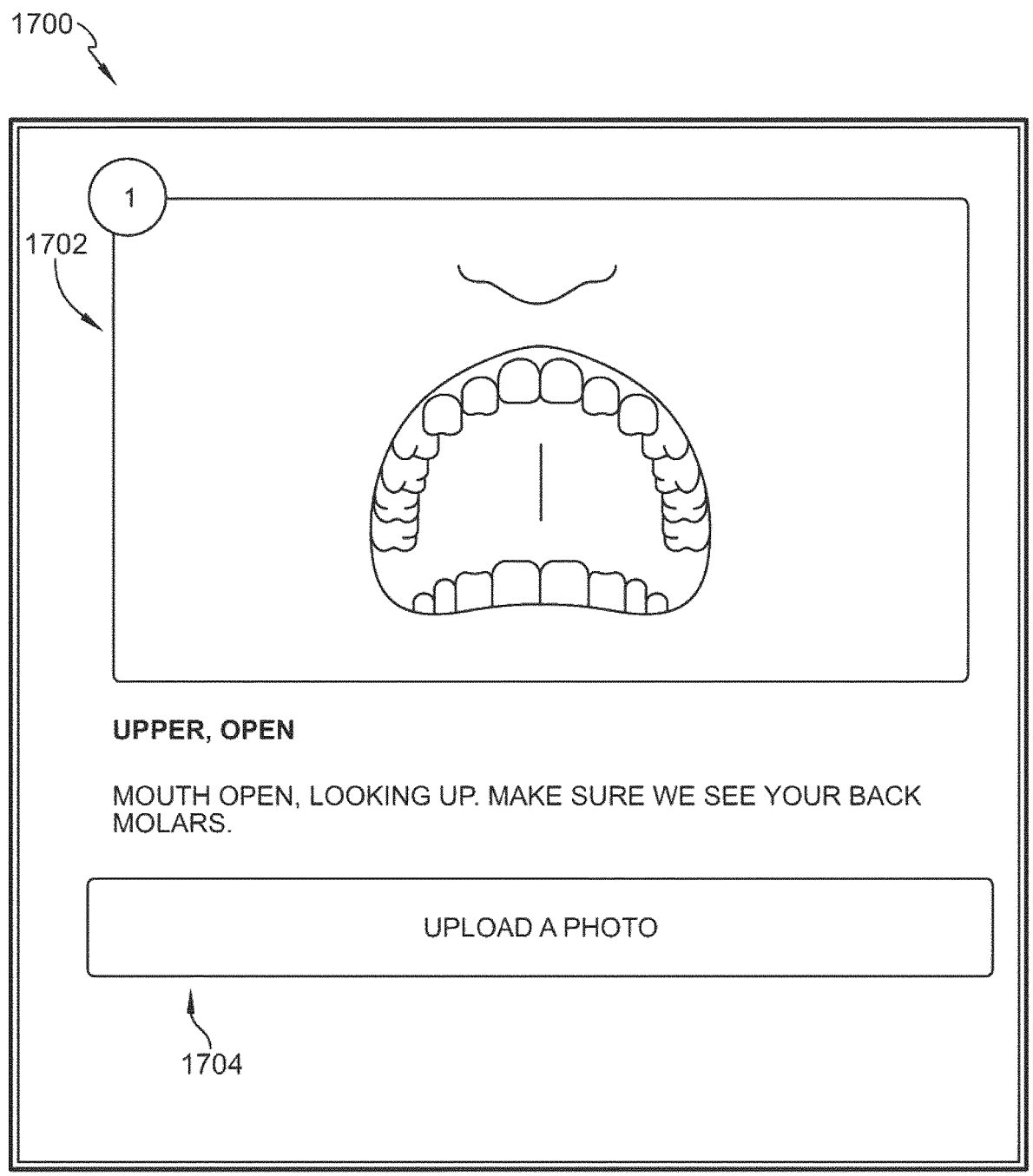
FIGS. 28A-28C are screen shots of an image upload user interface that may be generated by the application server of FIGS. 22-23.
Figure 28B:
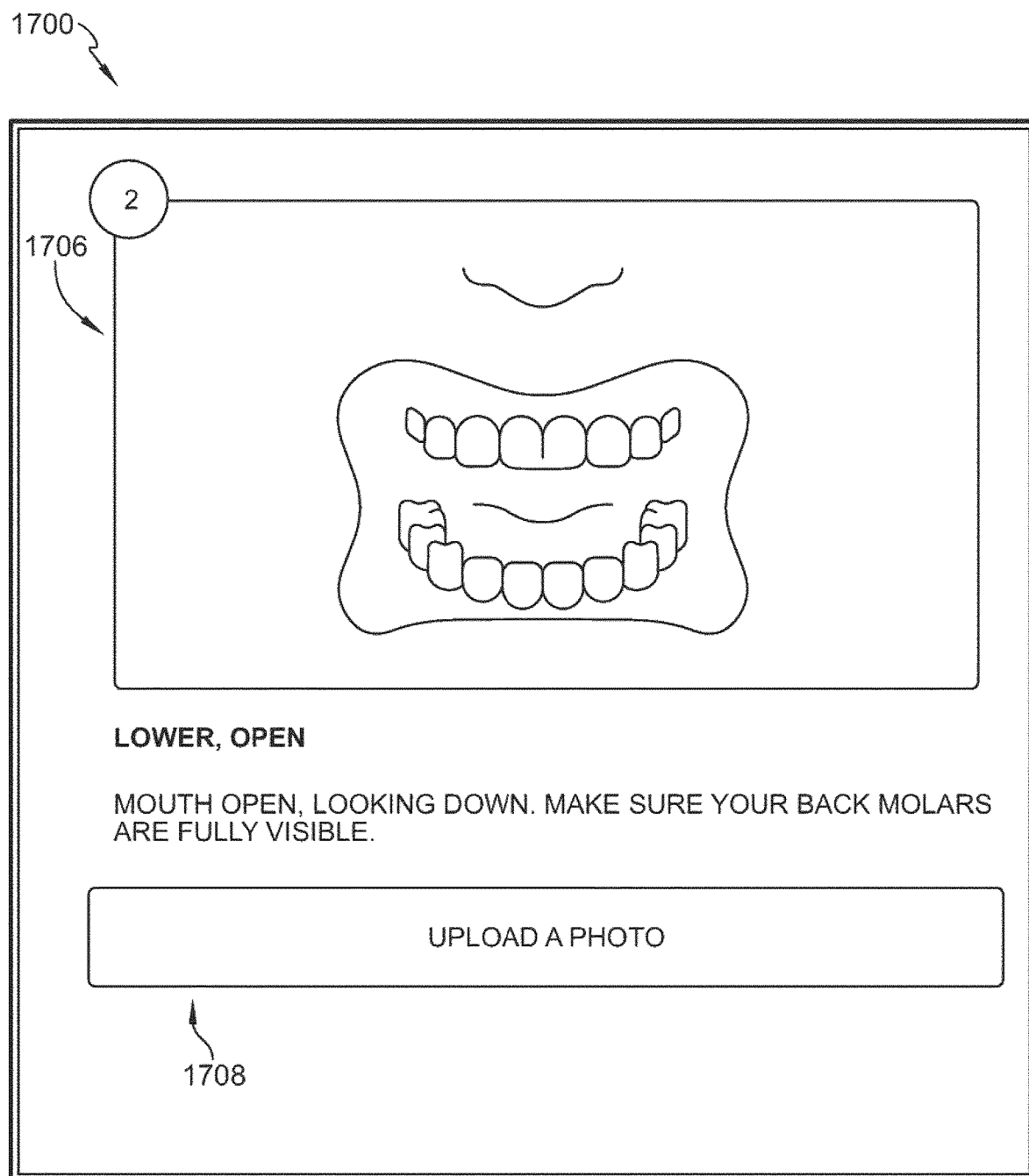
Figure 28C:
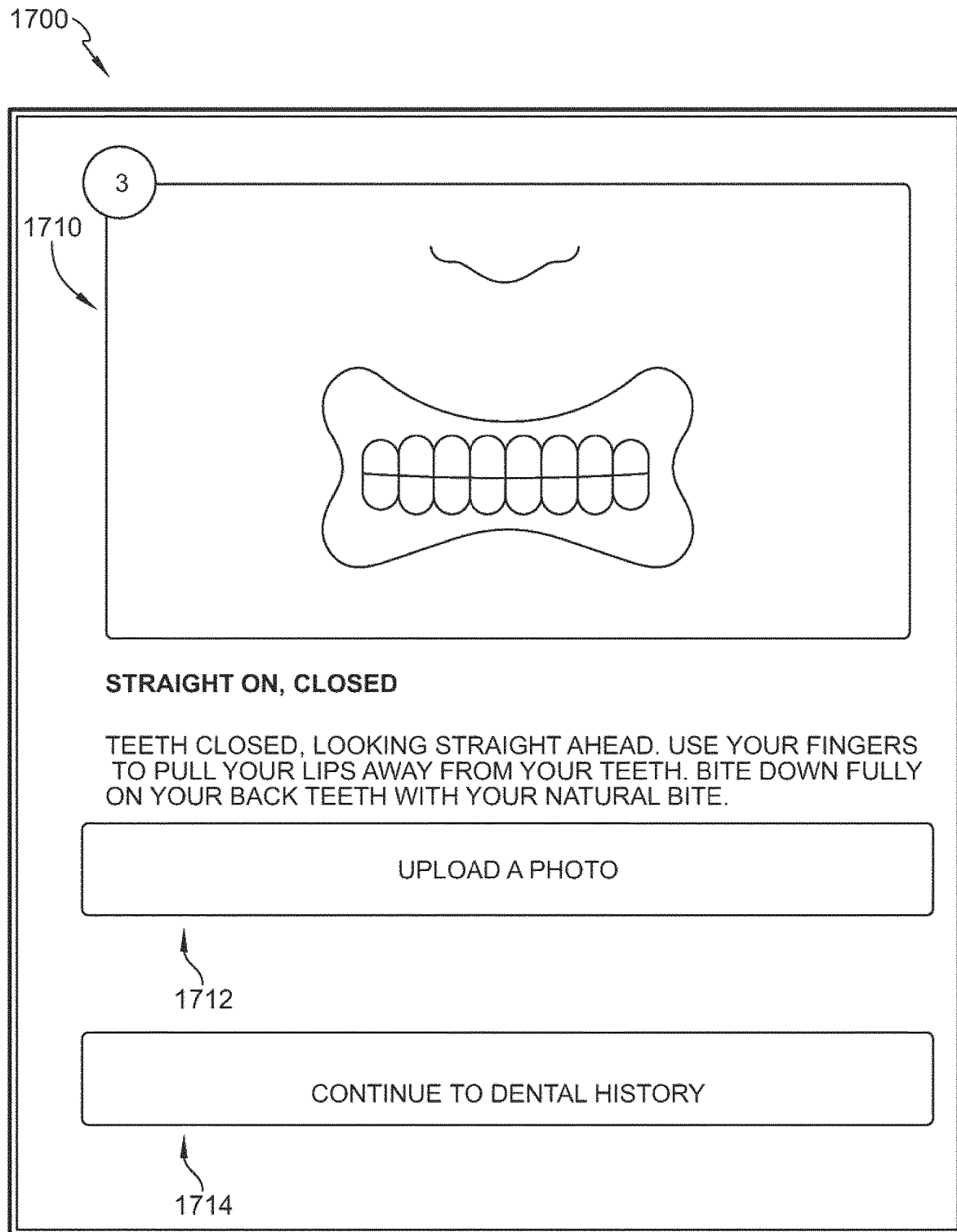

Referring now to FIGS. 28A-28C, a user interface 1700 for uploading images of the user's mouth and teeth is shown. The user interface 1700 may be used to receive images from the user device 1106 as described above in connection with block 1314 of FIG. 24A. The illustrative user interface 1700 is a web page provided by the application server 1102 to the user device 1106; however, it should be understood that the user interface 1700 may be embodied as native application, managed application, or other interface of the user device 1106. As shown, the user interface 1700 includes instructions 1702, 1706, 1710 and corresponding submit buttons 1704, 1708, 1712 for the three images that are used for photo assessment. In particular, the instructions 1702 and submit button 1704 shown in FIG. 28A are for an upper, open view; the instructions 1706 and submit button 1708 shown in FIG. 28B are for a lower, open view; and the instructions 1710 and submit button 1712 shown in FIG. 28C are for a straight-on, closed view. The user interface 1700 further includes a button 1714 to cause the user device 1106 to move on to the dental history questionnaire.

Figure 29A:

Referring now to FIGS. 29A-29C, a user interface 1800 for a dental history questionnaire is shown. The user interface 1800 may be used to receive a dental history questionnaire response as described above in connection with block 1322 of FIG. 24A. The illustrative user interface 1800 is a web page provided by the application server 1102 to the user device 1106; however, it should be understood that the user interface 1800 may be embodied as native application, managed application, or other interface of the user device 1106. As shown, the user interface 1800 includes multiple input elements 1802 that allow the user to provide information regarding the user's dental history. The user interface 1800 also includes a submit button 1804 that, when selected by the user, provides the dental history questionnaire response to the application server 1102. Referring now to FIGS. 29D-29E, another potential embodiment of a user interface 1800 for a dental history questionnaire is shown.

Figure 30A:
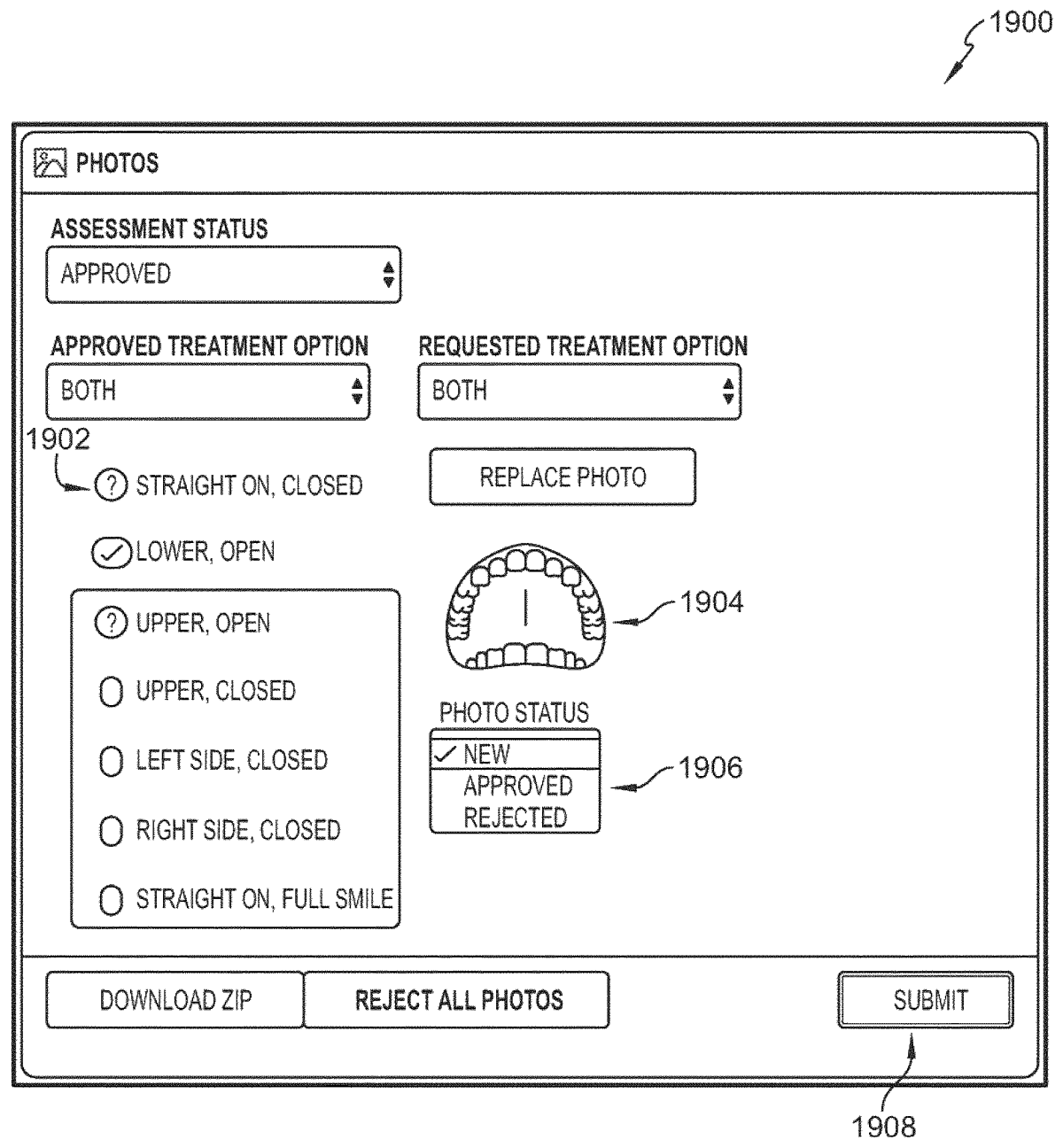

Referring now to FIGS. 30A and 30B, a user interface 1900 for photo assessment review is shown. The user interface 1900 may be used to provide data to the staff professional/hygienist and to receive approval as described above in connection with blocks 1322, 1324 of FIG. 24A. The illustrative user interface 1900 is a web page provided by the application server 1102 to the staff device 1104; however, it should be understood that the user interface 1900 may be embodied as native application, managed application, or other interface of the staff device 1104 and/or application server 1102. Additionally or alternatively, in some embodiments the user interface 1900 may be embodied as an embedded view within a staff portal user interface provided by the application server 1102.

As shown in FIG. 30A, the user interface 1900 includes multiple indicator elements 1902 for the different views. Each indicator element 1902 may indicate whether the image for the associated view has been approved, rejected, or is pending review. As shown, the user interface 1900 includes indicator elements 1902 for seven potential views, including the three views described above in connection with FIGS. 27A-27C, as well as four additional views that may be requested for complex cases. The user interface 1900 further includes an image thumbnail 1904 for the selected view (which is illustratively a line drawing but could include a photographic image) and a popup list 1906 used to approve or reject the selected image. The user interface 1900 includes a submit button 1908 that, when selected by the staff professional/hygienist, provides the approval to the application server 1102. The user interface 1900 also includes a view 1910, shown in FIG. 30B, that displays dental history questionnaire response for the user. The staff professional/hygienist may review data displayed in the view 1910 when performing the photo review.

Figure 31A:
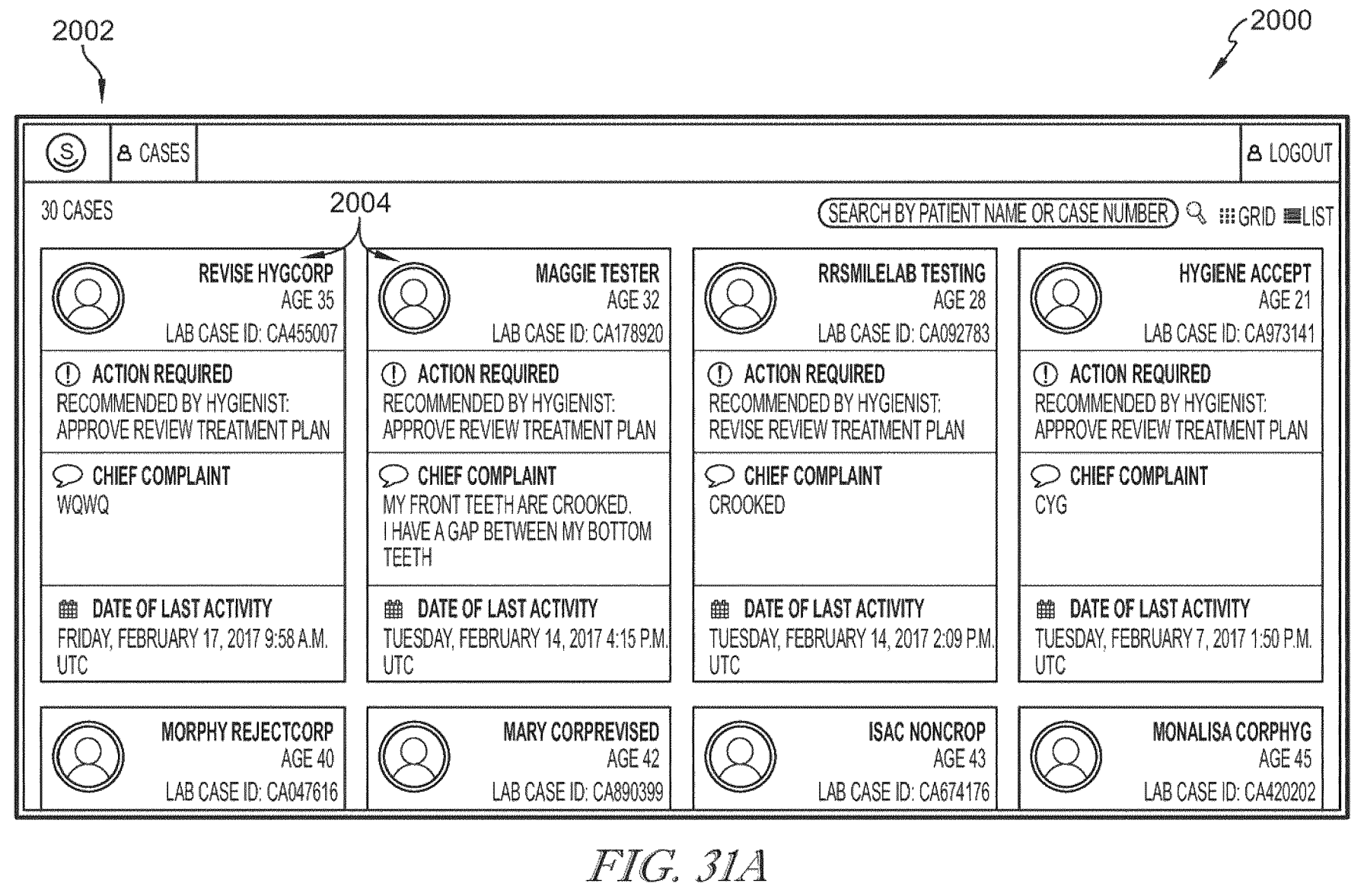

Referring now to FIGS. 31A-31E, a user interface 2000 for a provider portal is shown. The user interface 2000 may be used to allow a provider to perform a photo assessment, review a treatment plan, or otherwise interact with a user's case. The illustrative user interface 2000 is a web page provided by the application server 1102 to the provider device 1108; however, it should be understood that the user interface 2000 may be embodied as native application, managed application, or other interface of the provider device 1108. As shown in FIG. 31A, the user interface 2000 may include a case listing view 2002. The case listing view 2002 may include a case summary view 2004 for each user assigned to or otherwise associated with the provider. Selecting a case summary view 2004 may cause the provider device 1108 to display a corresponding case detail view 2006, shown in FIGS. 31B-31E.

Figure 31B:
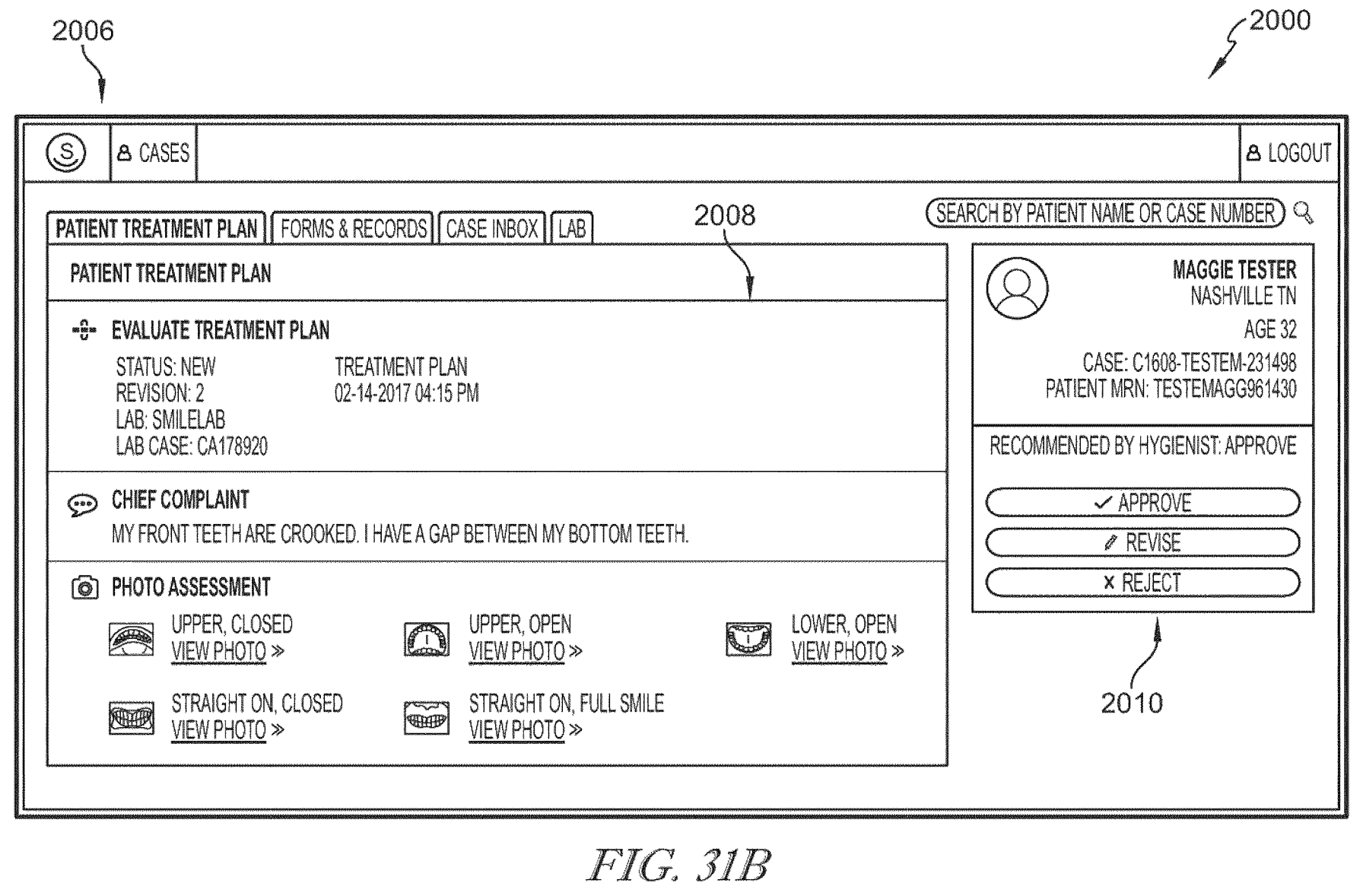
Figure 31C:
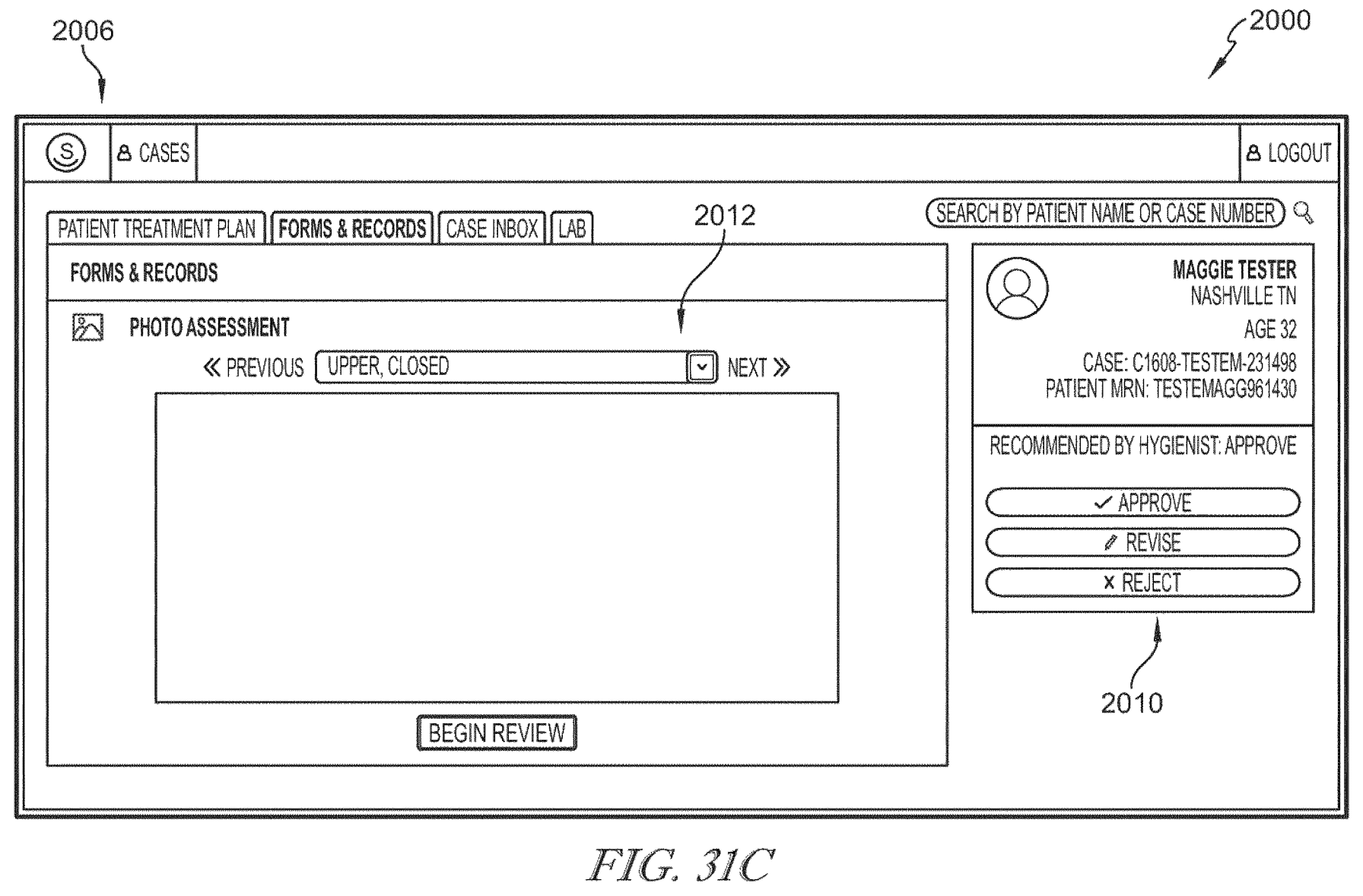
Figure 31D:
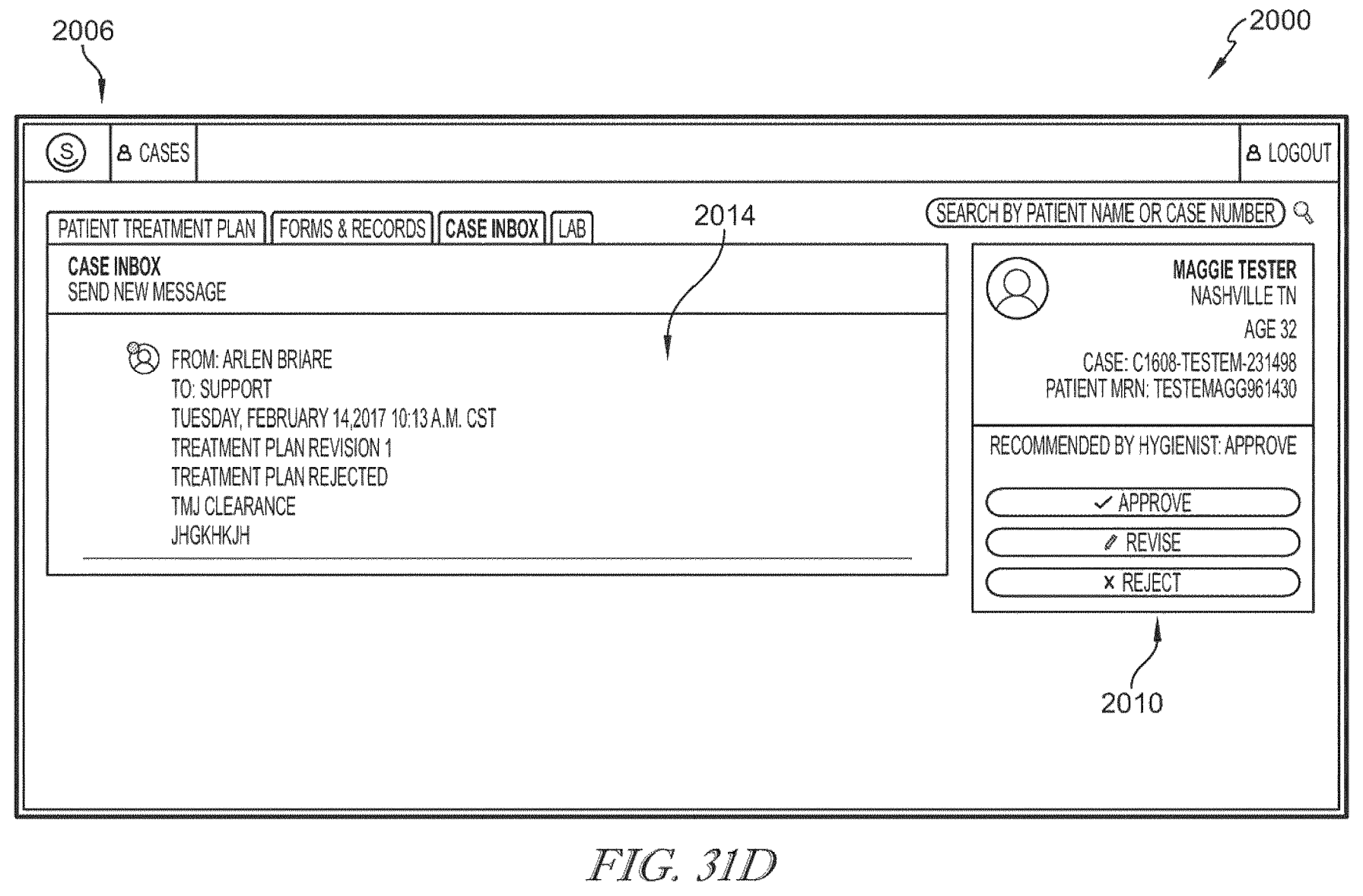
Figure 31E:
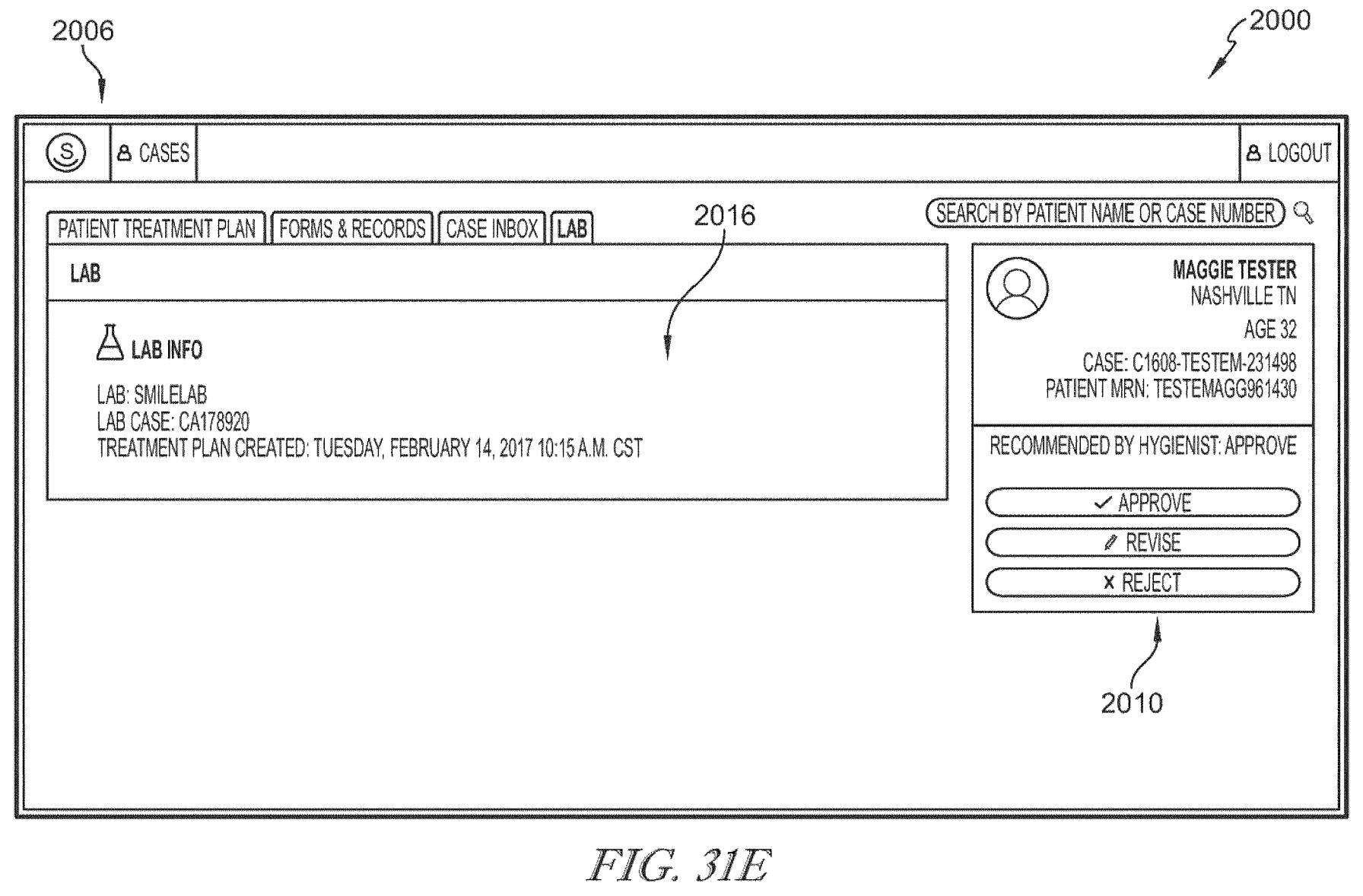

The case detail view 2006 may include a tabbed interface with multiple sub-views, including a patient treatment plan view 2008, shown in FIG. 31B. The patient treatment plan view 2008 may provide information on the treatment plan, the user's chief complaint, and the photo assessment, and may also allow the provider to initiate evaluation of the treatment plan and the photo assessment. The case detail view 2006 also includes an action box 2010, which includes buttons to allow the provider to approve or reject the treatment plan. As shown in FIG. 31C, the case detail view 2006 may include a form and record view 2012, which may display images (including treatment plan images and/or photo assessment images) and other documents for the provider to review. As shown in FIG. 31D, the case detail view 2006 may include a case inbox view 2014 that displays communications relevant to the user's case that are managed by the application server 1102. As shown in FIG. 31E, the case detail view 2006 may include a lab view 2016 that displays information for the dental lab 1110 assigned to the case.

Figure 32:
FIG. 32 is a screen shot of an account status user interface that may be generated by the application server of FIGS. 22-23.

Referring now to FIG. 32, a user interface 2100 for account status is shown. The illustrative user interface 2100 is a web page provided by the application server 1102 to the user device 1106; however, it should be understood that the user interface 2100 may be embodied as native application, managed application, or other interface of the user device 1106. The user interface 2100 may be used to display the status of the user's account, including indicating additional information required from the user or otherwise indicating the next step to be performed by the user. For example, the illustrative user interface 2100 indicates that the user's treatment plan is completed and ready for viewing. The user interface 2100 includes a button 2102 that, when selected by the user, launches a user interface for viewing the treatment plan. The user interface 2100 also includes a button 2104 that, when selected by the user, launches a user interface to purchase aligners for the treatment plan. The user interface for purchasing the aligners may collect account information, payment information, and perform other e-commerce functions as described above.

Figure 33:
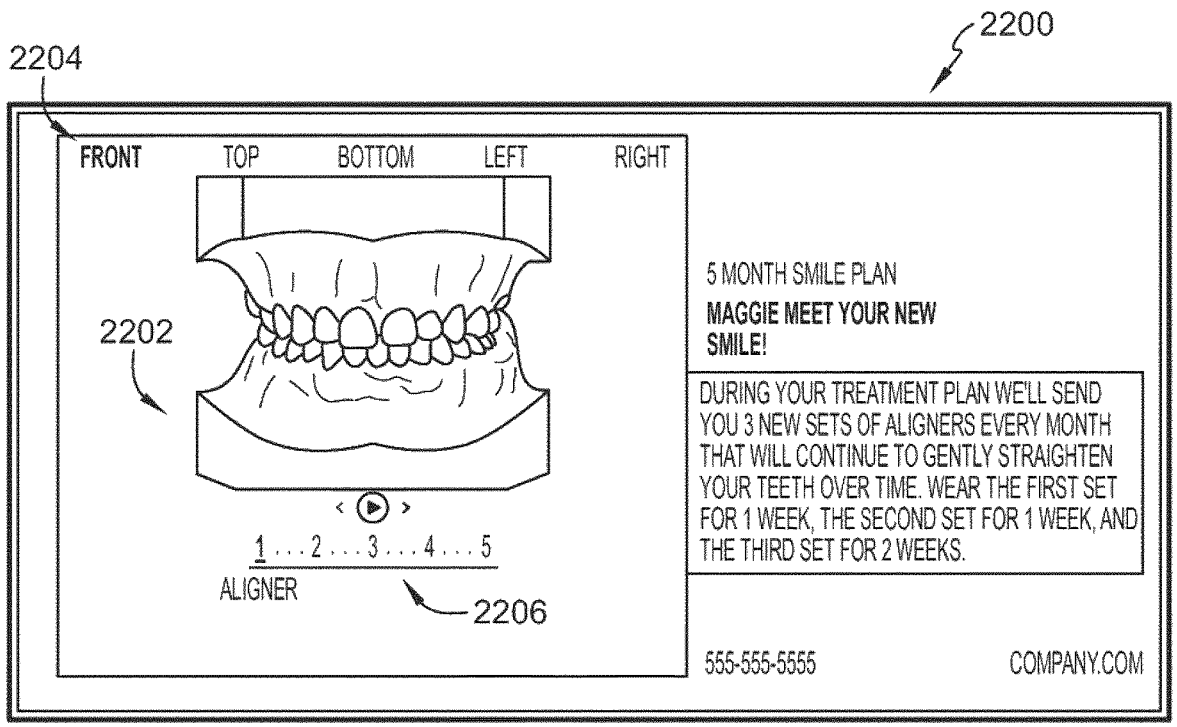
FIG. 33 is a screen shot of a 3D treatment plan viewer user interface that may be generated by the application server of FIGS. 22-23.

Referring now to FIG. 33, a user interface 2200 for viewing a 3D treatment plan is shown. The user interface 2200 may be used to view the treatment plan as described above in connection with block 1348 of FIG. 24B. The illustrative user interface 2200 is a web page provided by the application server 1102 to the user device 1106; however, it should be understood that the user interface 2200 may be embodied as native application, managed application, or other interface of the user device 1106. As shown, the user interface 2200 includes a 3D model view 2202 that displays the 3D model of the treatment plan. As described above in connection with block 1342 of FIG. 24B, the 3D model may be optimized for efficient viewing on the user device 1106. The user interface 2200 also includes a button bar 2204 that allows the user to switch between particular views of the 3D model and a slider 2206 that allows the user to switch between particular phases of the treatment plan. For example, the illustrative user interface 2200 displays a five-month treatment plan, and the slider 2206 allows the user to display a 3D model for each month of the treatment plan.

Figure 34A:
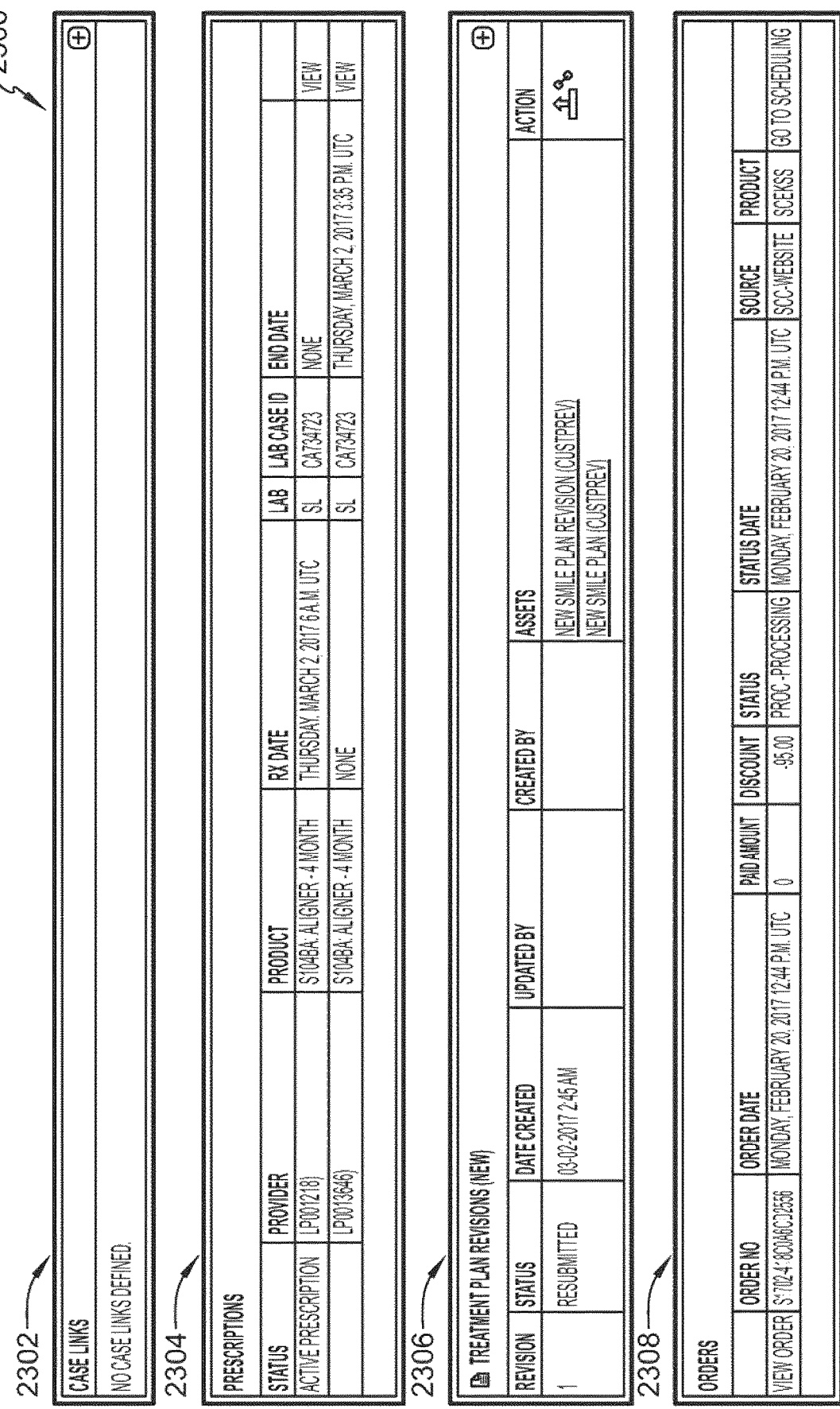
Figure 34B:
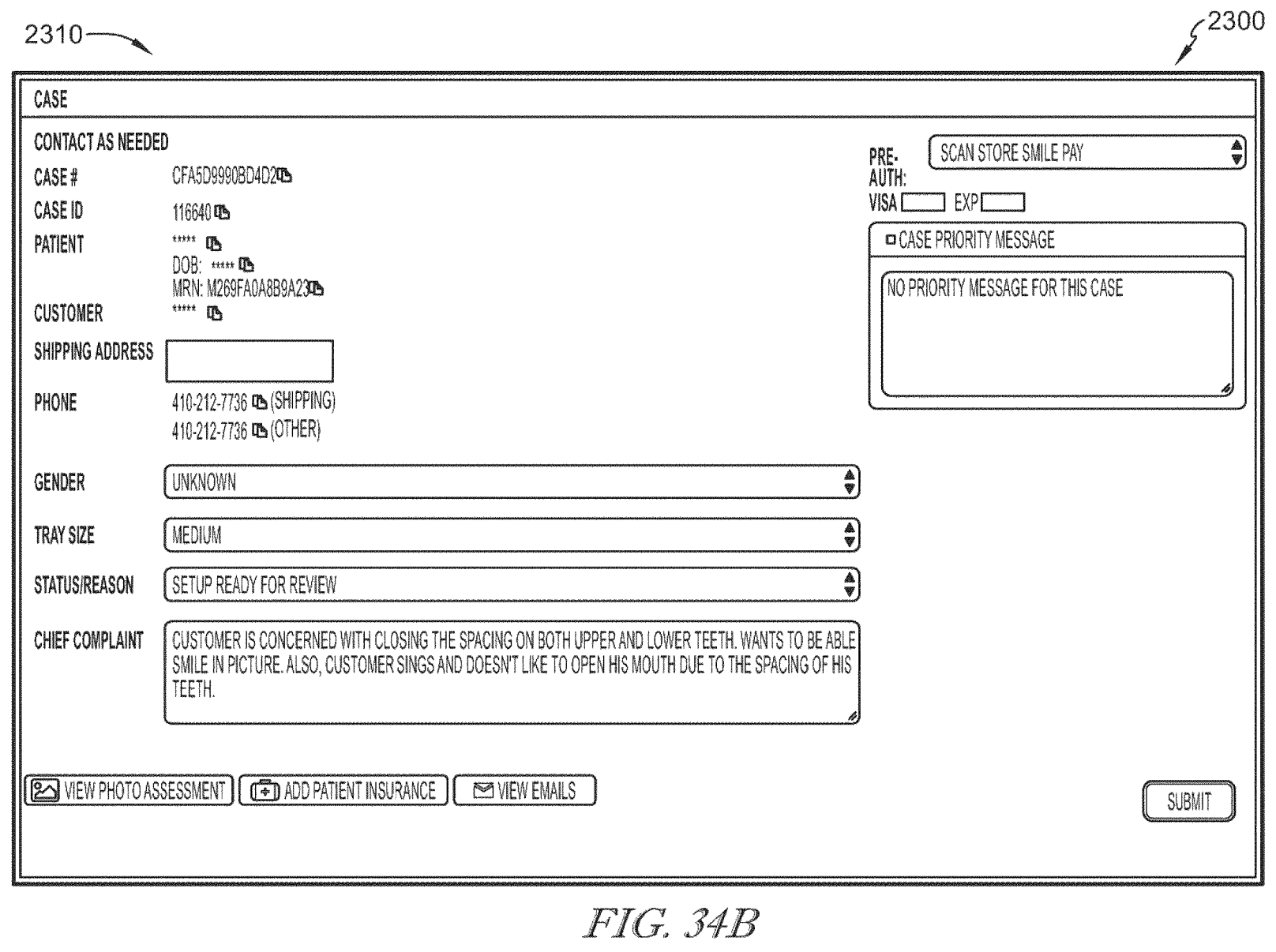
Figure 34D:
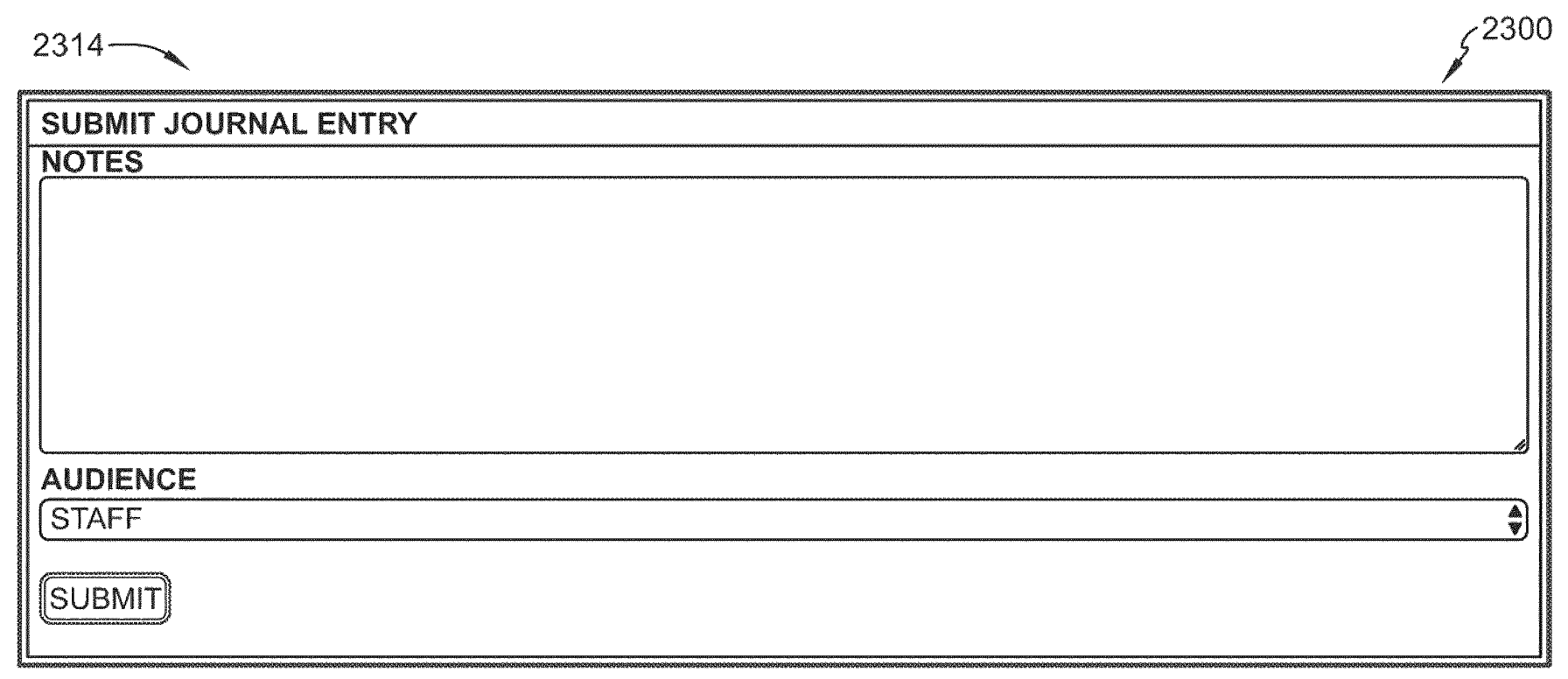
Figure 38A:
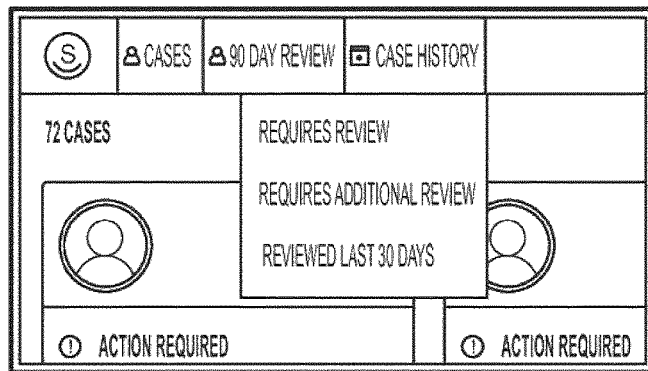
Figure 38B:
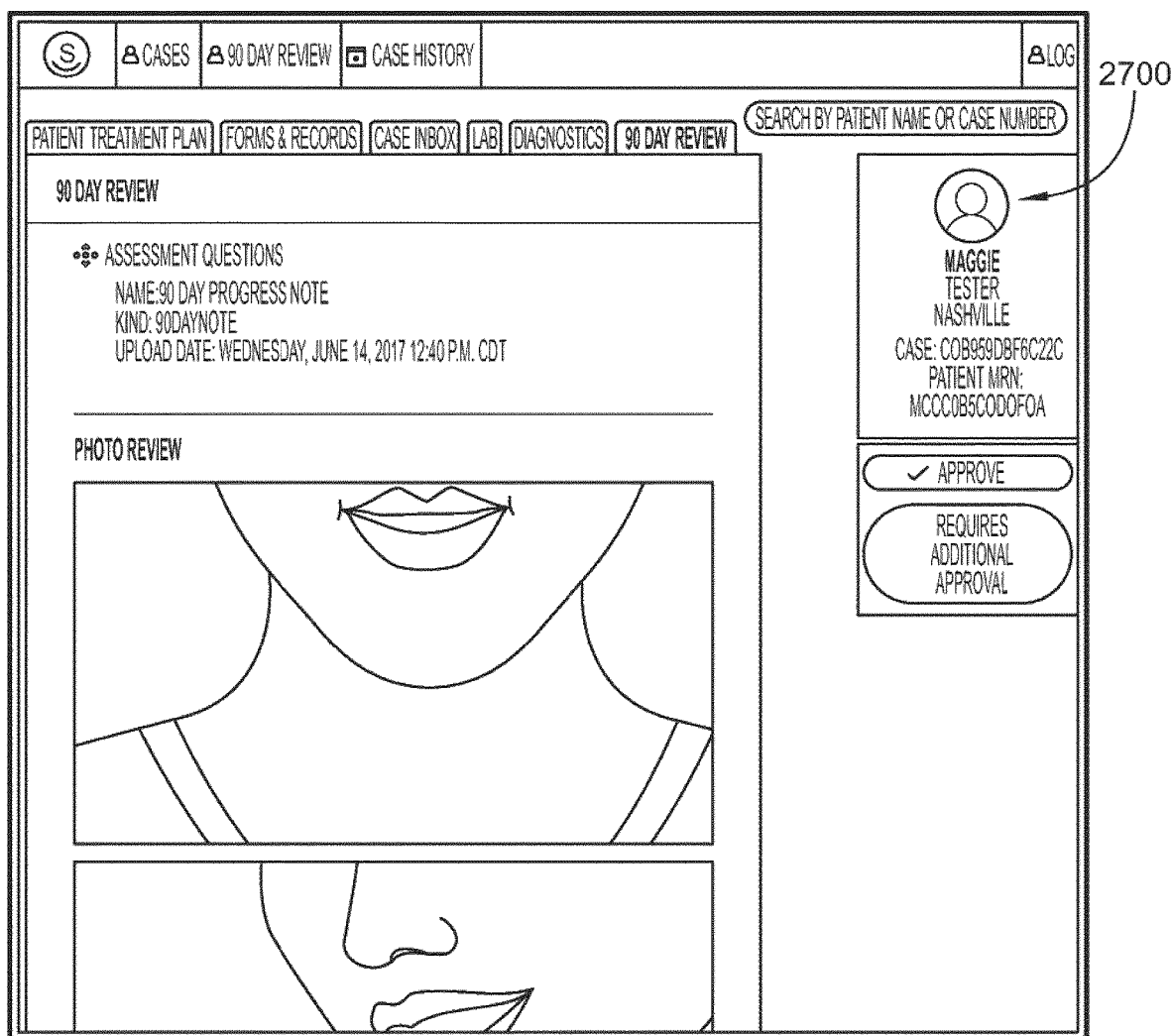
Figure 38C:
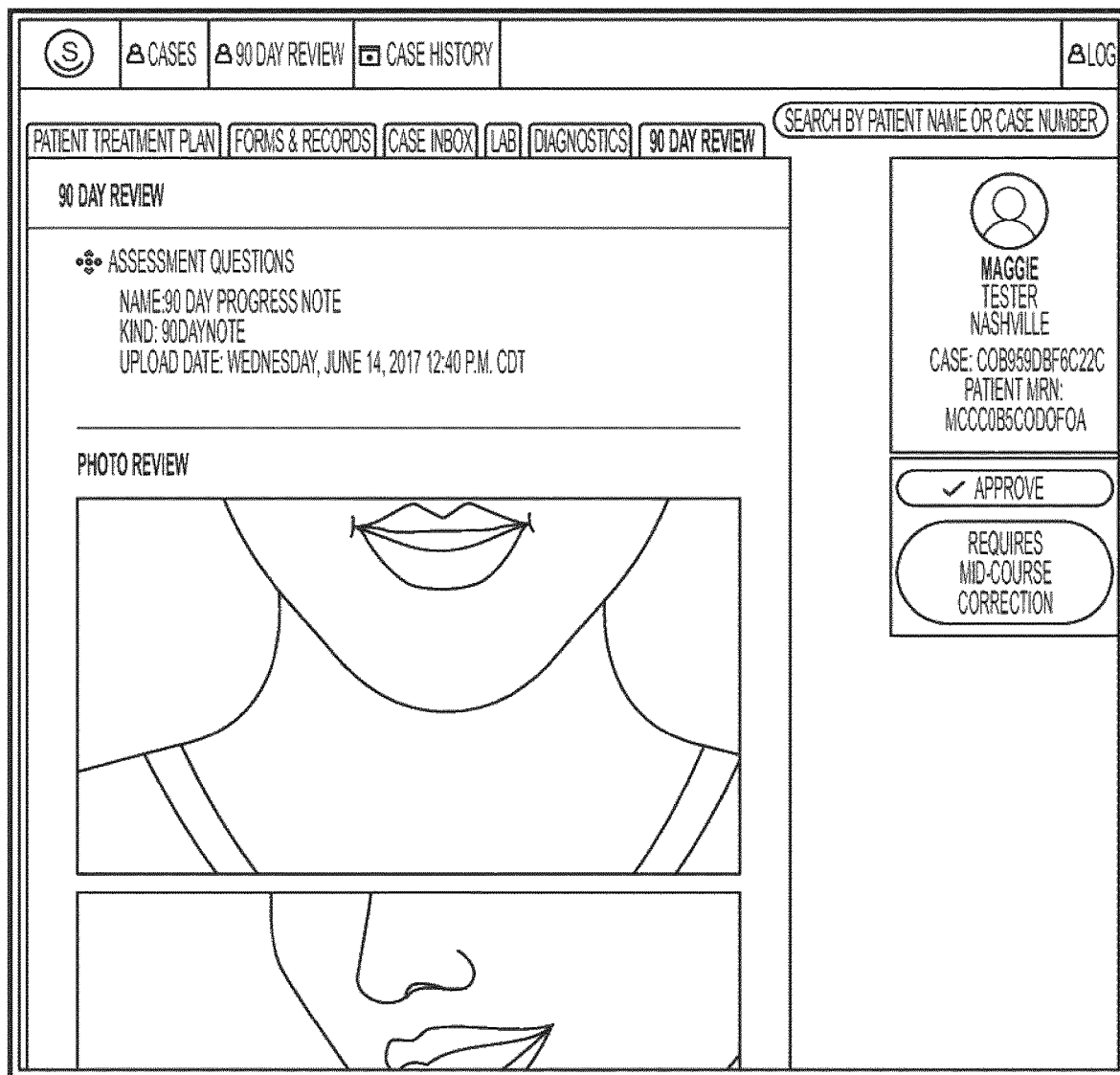

Referring now to FIGS. 34A-34F, a user interface 2300 for a staff portal is shown. The user interface 2300 may be used to store and manage all data relating to a particular user's case. Thus, the user interface 2300 may be used as an interface to a secure electronic medical records repository provided by the application server 1102. The illustrative user interface 2300 is a web page provided by the application server 1102 to the staff device 1104; however, it should be understood that the user interface 2300 may be embodied as native application, managed application, or other interface of the staff device 1104 and/or the application server 1102. The illustrative user interface 2300 shown in FIGS. 34A-34F illustrates one potential embodiment of the documents and other data that may be stored for each user by the application server 1102. As shown in FIGS. 34A-34F, the user interface 2300 includes multiple views, with each view allowing access to part of the data associated with a particular user's case. As shown in FIG. 34A, the user interface 2300 may include a case link view 2302, a prescription view 2304, a treatment plan revision view 2306, and an order view 2308. The treatment plan revision view 2306 may track changes made to the treatment plan during the provider's review process, as described above in connection with blocks 1332 to 1346 of FIG. 24B, and the prescription view 2304 may be populated after the provider has approved a treatment plan. As shown in FIG. 34B, the user interface 2300 may include a case detail view 2310, which includes details on the user's contact information, payment information, case status, and also includes links to the user's photo assessment and other information. As shown in FIG. 34C, the user interface 2300 may include a journal view 2312, which records events related to the user's case. As shown in FIG. 34D, the user interface 2300 may include a journal entry view 2314, which allows a staff professional or other person to enter events into the journal for the user's case. Each journal entry may be restricted by audience (e.g., staff, provider, user, or other audience). As shown in FIG. 34E, the user interface 2300 may include a case message view 2316, which records all messages sent via the application server 1102 concerning the user's case. The messages may be exchanged, for example, between the provider, staff, and/or the dental lab 1110 for a case. As shown in FIG. 34F, the user interface 2300 may include a case file view 2318 and a case document view 2320. The views 2318, 2320 may provide an interface to secure storage for all images, treatment plans, consent forms, and other documents related to a user's case.

Referring to FIGS. 35-37, another embodiment of a dental tray 200 includes a substantially arched mouth insert 202 that is sized and shaped to be inserted into the user's mouth. Particularly, the insert 202 is sized and shaped to be received into either an upper portion or a lower portion of the user's mouth. The insert 202 includes a cavity 204 defined by a bottom wall 206 and a pair of sidewalls 208 extending upward from the bottom wall 206. The cavity 204 is sized to receive the putty mixture. When the dental tray 200 is inserted into the user's mouth, the user bites down on the dental tray 200 so that the user's teeth are within the cavity 204 and bite into the putty mixture. A flange 210 extends from a front of the dental tray 200. The flange 210 is configured to be gripped by the user to insert and remove the dental tray 200 from the user's mouth.

Figure 39:
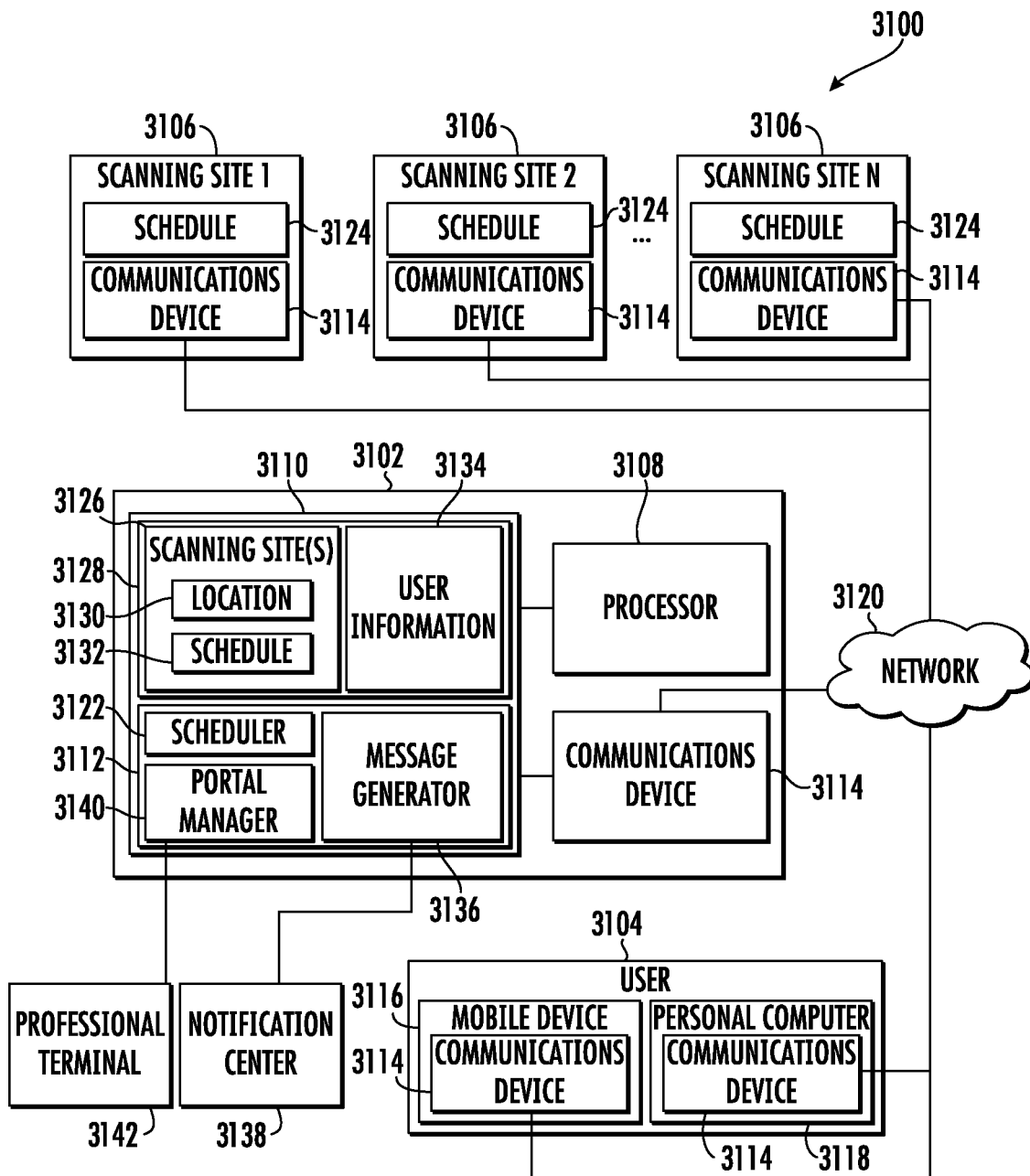
FIG. 39 shows an appointment management system according to an exemplary embodiment.

Referring to FIG. 39, an appointment management system 3100 is shown. The appointment management system 3100 includes a computing system 3102, a mobile device 3116 of a user 3104, a personal computer 3118 of the user 3104, and a plurality of intraoral scanning sites 3106.

The computing system 3102 includes a processor 3108 and memory 3110. Processor 3108 may be a general purpose or specific purpose processor, an application specific integrated circuit (ASIC), one or more field programmable gate arrays (FPGAs), a group of processing components, or other suitable processing components. Processor 3108 may be configured to execute computer code or instructions stored in memory 3110 or received from other computer readable media (e.g., CDROM, network storage, a remote server, etc.) to perform one or more of the processes described herein. Memory 3110 may include one or more data storage devices (e.g., memory units, memory devices, computer-readable storage media, etc.) configured to store data, computer code, executable instructions, or other forms of computer-readable information. Memory 3110 may include random access memory (RAM), read-only memory (ROM), hard drive storage, temporary storage, non-volatile memory, flash memory, optical memory, or any other suitable memory for storing software objects and/or computer instructions. Memory 3110 may include database components, object code components, script components, or any other type of information structure for supporting the various activities and information structures described in the present disclosure. Memory 3110 may be communicably connected to processor 3108 via processing circuit 3112 and may include computer code for executing (e.g., by processor 3108, etc.) one or more of the processes described herein.

The memory 3110 is described below as including various circuits 3112. While the exemplary embodiment shown in the figures shows each of the circuits 3112 as being separate from one another, it should be understood that, in various other embodiments, the memory 3110 may include more, less, or altogether different circuits 3112. For example, the structures and functions of one circuit 3112 may be performed by another circuit 3112, or the activities of two circuits 3112 may be combined such that they are performed by only a signal circuit 3112. Additionally, it should be understood that any of the functionalities described as being performed by a circuit 3112 that is a part of the memory 3110 may also be performed by a separate hardware component having its own processors, network interfaces, etc.

As shown in FIG. 39, the appointment management system 3100 includes one or more communications device(s) 114. The communications device(s) 114 can be or include components configured to transmit and/or receive data from one or more remote sources. For instance, each of the intraoral scanning site(s) 106 may include a respective communications device 3114, the user 3104 may have one or more communications device(s) 114 embodied on the user's 104 mobile device 3116, personal computer 3118, etc., and/or the computing system 3102 may include a communications device 3114. Each of the respective communications devices 3114 may permit or otherwise enable data to be exchanged between the user 3104, the intraoral scanning site(s) 106, and/or the computing system 3102. The communications device 3114 may communicate via a network 3120. The network 3120 may be a Local Area Network (LAN), a Wide Area Network (WAN), a Wireless Local Area Network (WLAN), an Internet Area Network (IAN) or cloud-based network, etc. In some implementations, the communications device(s) 114 may access the network 3120 to exchange data with various other communications device(s) 114 via cellular access, a modem, broadband, Wi-Fi, satellite access, etc.

In some implementations, the user 3104 may access a website (or other network-based portal) associated with the appointment management system 3100. The user 3104 may book an appointment at an intraoral scanning site 3106 on the website. The user 3104 may be directed to the website through, for instance, an advertisement on the user's 104 social media account. Additionally or alternatively, the user 3104 may search for (e.g., on the internet, etc.) the website associated with the appointment management system 3100.

Additionally or alternatively, the user 3104 may receive a message directing them to the website to book an appointment at an intraoral scanning site 3106. The processor 3108 may control the communications device 3114 to send the message to the user 3104 in response to various conditions. For instance, the processor 3108 may determine that the user 3104 previously signed up to receive an in-home dental impression kit and never returned the completed kit. The processor 3108 may identify a time between an order date (or shipment date) of the dental impression kit and the current date. The processor 3108 may compare the identified time to a threshold time indicative of the user 3104 likely not returning impressions from the dental impression kit. Where the identified time exceeds the threshold time, the processor 3108 may automatically generate and send the message to the user 3104. As another example, the processor 3108 may determine that the impressions received from the user 3104 were, for instance, incomplete. A technician may review the impressions (or a scan thereof) to determine their suitability for manufacturing dental aligners. When the impressions are determined to be incomplete, the technician may flag the impressions as incomplete. When the impressions are flagged, the processor 3108 may automatically generate and send the message to the user 3104 prompting the user to schedule an intraoral scan.

The website may include a home page, an instructional page detailing how the customer aligner process works, a results page, a locations page, and/or additional or alternative pages. Each of these pages may present different information to the user 3104. For instance, the home page may present information pertaining to an overall user experience. The instructional page may present a step-by-step overview starting from an appointment to receiving customized aligners. Additionally, the instructional page may present a video to the user 3104. The video may include graphics and/or text that show how the customized aligners reposition the user's 104 teeth, among other information. The video may also show the user 3104 what to expect upon arrival at their appointment location, should they choose to book an appointment. The results page may include before-and-after pictures (or a rolling video of before-and-after pictures) of previous users who have used aligners to reposition their teeth. The locations page includes locations associated with each of the respective intraoral scanning sites 3102.

Referring now to FIG. 39 and FIG. 40, the user 3104 may access the locations page of the website. Specifically shown in FIG. 40 is a reservation page 3200 which may be a portion of the locations page or a portion of the home page.

In some embodiments, the computing system 3102 may include a scheduler 3122. The scheduler can be or include instructions that, when executed by the processor 3108, cause the processor 3108 to generate and/or manipulate pages and displays for scheduling an appointment at an intraoral scanning site 3106. While shown as embodied on memory 3110 of the computing device 3102, in some implementations, the scheduler 3122 may be separate from the computing device 3102. For instance, the scheduler 3122 may be located remotely from the computing device 3102. In instances such as these, the scheduler 3122 may have a separate processor 3108 and memory 3110 (a dedicated processor and memory, for example). A user 3104 may schedule an intraoral scan at a particular intraoral scanning site 3106 via the website. The website may be controlled by the processor 3108 using instructions from the scheduler 3122. Following the intraoral scan, the user 3104 may, in some instances, order aligners that are customized for the user 3104. For instance, the user 3104 may be satisfied with the overall process at the intraoral scanning site 3106 and results of other users 3104. Therefore, the user 3104 may purchase aligners for aligning the user's 104 teeth. The aligners may be constructed of a polymer material, such as Polyethylenterephthalat-Glycol Copolyester (PET-G), which is thermoformed to positive molds (or models) of the user's 104 dentition at various intervals between a starting position and an ending position. The positive molds of the user's dentition 3104 may be generated based on the treatment plan. The aligners may be used by the user 3104 in stages to move the user's teeth towards the ending position. For example, the user 3104 may be directed to wear a first aligner during a first month, a second aligner during a second month, a third aligner during a third month, and so on for a treatment period. These aligners may be shipped to the user 3104 following production of the aligners (e.g., at a fabrication site which generates or otherwise produces the aligners). In some instances, the aligners may be shipped in stages, all at once in one box, etc. Each of the aligners may be administered by the user in a predetermined sequence and for a predetermined duration. For instance, a first aligner (which corresponds to a starting position of the user's teeth) may be administered by the user for a duration (e.g., a month, 90 days, etc.), a second (and additional intermediate) aligner(s) may be administered by the user for the same duration, and a final aligner may be administered for the same duration. Each of these aligners may move the user's teeth from the starting position to one or more intermediate positions, and from the one or more intermediate positions to the final positions based on the treatment plan.

As shown in FIG. 40, the reservation page 3200 includes locations 3202, dates 3204, and times 3206. Included in the locations 3202 is information corresponding to each of the intraoral scanning site(s) 106. While each of the intraoral scanning site(s) 106 are shown as included, in some embodiments, only a subset of intraoral scanning site(s) 106 may be shown. For instance, the intraoral scanning site(s) 106 which are located nearest to the user 3104 may be shown. As one example, the processor 3108 may receive data from a communications device 3114 associated with the user 3104 (e.g., the mobile device 3114, personal computer 3118, etc.). The data may include location-based data associated with the user 3104. The processor 3108 may use this data to select, from each of the intraoral scanning site(s) 106, a subset of intraoral scanning site(s) 106 to include in the locations 3202. As another example, the user 3104 may be prompted to provide a zip code. The processor 3108 may use the zip code provided by the user 3104 to determine intraoral scanning site(s) 106 that are located nearest to (or within) the zip code.

In some implementations, a user 3104 may search for specific locations 3202 (instead of selecting ones that are nearest to the user's 104 location). The user 3104, for instance, may be traveling to a different city than their city of residence and may want to schedule an appointment at an intraoral scanning site 3106 located in that different city. As a result, the user 3104 is not limited to scheduling appointments at intraoral scanning sites 3106 in their own city, but may schedule appointments at any of the intraoral scanning sites 3106. In implementations such as these, the user 3104 may provide a zip code that is different from their current zip code (e.g., the zip code associated with the city to which they are traveling).

In still other implementations, one or more of the intraoral scanning sites 3106 may be a mobile intraoral scanning site 3106. For instance, the mobile intraoral scanning site 3106 may be implemented in a vehicle (e.g., an automobile, a truck, a van, a bus, etc.), as part of a kiosk (e.g., located within another store or within a shopping mall), or comprise a pop-up location in operation for only a limited time period (e.g., one day, one week, one month). The mobile intraoral scanning site 3106 may be included in the locations 3202 on the reservations page 3200. As will be described in further detail below, a user 3104 may be able to arrange for the mobile intraoral scanning site 3106 to travel to a set location (e.g., a location set by the user, such as their home or place of business), and the user 3104 may receive an intraoral scan at the set location.

Upon selecting a location 3202 of an intraoral scanning site 3106 from the list of locations 3202 of intraoral scanning sites 3106, the user 3104 may select an available date from the list of dates 3204. Each intraoral scanning site 3106 may maintain a schedule 3124. The schedule 3124 may be maintained locally (e.g., at each respective intraoral scanning site 3106, etc.) and communicated to the computing system 3102. The scheduler 3122 can include instructions to access the schedule 3124 of the intraoral scanning site 3106 selected by the user 3104 and determine available days/times for an appointment for the user 3104 based on the schedule 3124 for the intraoral scanning site. The scheduler 3122 can include instructions to display available times and dates for the intraoral scanning site 3106 based on the schedule 3124 associated with the intraoral scanning site 3106. Additionally or alternatively, the schedule 3124 may be a cloud-based schedule that is remotely accessible by the processor 3108 and by the respective intraoral scanning site 3106. In implementations such as these, the memory 3110 may store intraoral scanning site data 3126 corresponding to each respective intraoral scanning site 3106. The intraoral scanning site data 3126 may be stored in a database 3128 within memory 3110. The intraoral scanning site data 3126 may include a location 3130 associated with the intraoral scanning site 3106 (or other information usable to identify a particular intraoral scanning site 3106) and a corresponding schedule 3132 for the intraoral scanning site 3106. The scheduler 3122 can include instructions to determine the schedule for the selected location 3202 of the intraoral scanning site 3106 by cross-referencing data for the selected location 3202 with location 3130 within the intraoral scanning site data 3126. Following cross-referencing the data for the selected location 3202, the scheduler 3122 can include instructions to identify the schedule for the corresponding selected location 3202.

In each of these arrangements, the scheduler 3122 can include instructions to identify available appointment times for the intraoral scanning site 3106. These available appointment times may be presented to the user 3104 for selection and booking an appointment.

As shown in FIG. 40, the intraoral scanning site(s) 106 may have extended hours (e.g., open nights, weekends, etc.). In implementations such as these, the user 3104 may be more likely to schedule an appointment when the hours are extended due to a lessened likelihood of a scheduling conflict between the user 3104 and a given intraoral scanning site 3106.

The processor 3108 may access the schedule 3124, 3132 for the selected location 3202 to determine available dates via the instructions from the scheduler 3122. The processor 3108 may display the available dates in the list of dates 3204. Following a selection of an available date from the list of dates 3204, the times available for the selected date may be displayed to the user 3104. The processor 3108 may determine the available times in the same manner in which the available dates are determined. The user may select an available time to book their scan from the list of available times 3206.

While described herein as the user first selecting a location, in some embodiments, the user may first select a preferred date and/or time and available locations (and/or dates and locations) may then be displayed based on the selected preferred date and/or time (and/or dates and locations). In each of these implementations, the user 3104 may reserve a time at a particular intraoral scanning site 3106, and at the reserved time, the user 3104 may arrive at the particular intraoral scanning site 3106 and receive their intraoral scan, as will be discussed in further detail below.

In some implementations, the user 3104 may select the mobile intraoral scanning site 3106. In implementations such as these, the processor 3108 may identify a schedule 3124, 3132 associated with the mobile intraoral scanning site 3106 using instructions from the scheduler 3122. The user 3104 may request a date 3204 and time 3206 that is available for the mobile intraoral scanning site 3106. The user 3104 may then provide a location to arrange the appointment with the mobile intraoral scanning site 3106. The mobile intraoral scanning site 3106 may have a predetermined radius (e.g., 10 miles, 20 miles, 25 miles, 50 miles, etc.) within which the mobile intraoral scanning site 3106 operates. The user 3104 may provide a location within the predetermined radius. At the reserved time, the mobile intraoral scanning site 3106 may be driven to the location provided by the user 3104. The user 3104 may similarly arrive at the provided location at the reserved time and receive an intraoral scan, as will be discussed in further detail below.

Referring now to FIG. 41, following the user 3104 selecting an available time 3206 (e.g., as shown in FIG. 40), the scheduler 3122 can include instructions to direct the user 3104 to a booking screen 3300. At the booking screen 3300, the user 3104 may be prompted to provide various personal information 3302 (e.g., first and last name, a phone number, an e-mail address, etc.). Additionally, the user 3104 may be prompted to opt into (or not opt into) a messaging service by selecting box 3304. The messaging service may provide one or more messages to the user 3104 concerning the user's 104 booked appointment, as will be discussed in further detail below. The personal information 3302 and data corresponding to whether the user 3104 opted into the messaging service may be stored in database 3128 in a user file 3134. The user file 3134 may be a file associated with the user 3104 and may include various types of data associated with the user 3104. The user file 3134 nay be subsequently used for generating messages to the user 3104 before and/or after the user's 104 appointment. The user file 3134 may also include the intraoral scan, the treatment plan, progress information, photographs, etc.

As shown in FIG. 41, the appointment may be free to the user 3104. In some implementations, the appointment may have a flat fee (e.g., $25, $95, etc.). In still other implementations, the appointment may have a booking hold which is not charged to the user 3104. Following the user 3104 providing their personal information, the user 3104 may be prompted to book their scan by selecting button 3306.

Figure 42:
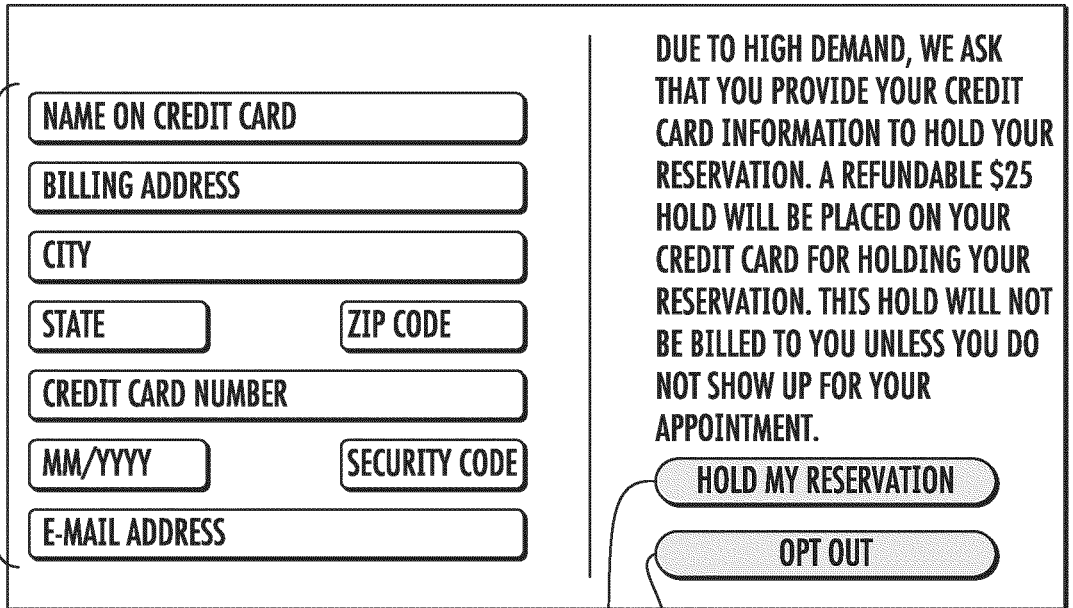
FIG. 42 shows a reservation hold screen associated with the appointment management system of FIG. 39 according to an exemplary embodiment.
Figure 43A:
FIG. 43A and FIG. 43B show example confirmation windows associated with the appointment management system of FIG. 39 according to an exemplary embodiment.
Figure 43B:

Referring now to FIG. 42, when the user 3104 books their scan by selecting button 3306 (of FIG. 41), the scheduler 3122 can include instruction to direct the user 3104 to a holding page 3400. At the holding page 3400, the user 3104 may be prompted to provide credit card information 3402. The credit card information 3402 may be requested to hold the available time selected by the user 3104 (e.g., as selected on reservations page 3200). The credit card information 3402 may be used to place a hold (for instance, $25) on the user's 104 credit card. In some implementations, the hold may be a refundable hold (e.g., the credit card for the user 3104 is not billed or is refunded unless the user 3104 does not show up for their appointment at the selected time).

In some implementations, the hold may be optional. For instance, the user 3104 may be able to hold the reservation (through selection of button 3404) or opt out of holding the reservation (through selection of button 3406). The user 3104 may provide their credit card information 3402 and select button 3404. In selecting prompt 3404, confirmation window 3500 may be displayed to the user 3104 (e.g., indicating that the user's 104 reservation has been confirmed). Additionally, the user 3104 may not provide their credit card information 3402, and instead, opt out by selecting button 3406. In some implementations, selecting button 3406 may direct the user 3104 back to the reservations page 3200. In other implementations, selecting button 3406 may cause confirmation window 3502 to be displayed to the user 3104 (e.g., indicating that the user's 104 reservation is still confirmed despite the user 3104 not providing credit card information 3402). By providing credit card information 3402, the user 3104 may be more likely to show up for their appointment, despite their credit card never being charged.

In one or more embodiments, following the user 3104 reserving (and optionally holding) their appointment, the user 3104 may want to reschedule their appointment. To do so, the user 3104 may call the intraoral scanning site 3106 to reschedule their appointment. Additionally, the user 3104 may go onto the website associated with the appointment management system 3100, provide log-in information or other identifying information to look-up their appointment and access, for instance, a user portal (as will be discussed in greater detail below). The user portal may include various appointment-related information including the time, date, and location for their appointment. Following the user's appointment, the user portal may include various treatment plan information (such as a virtual representation of the user's 104 treatment plan at different stages or a simulated representation of the user's 104 teeth through progression of the treatment plan), progress information provided by the user 3104, etc., as will be discussed in greater detail below. The user 3104 may select their appointment and reschedule their appointment in substantially the same manner by which the user 3104 booked their appointment (e.g., by following the progression from FIG. 40 through FIG. 42).

Referring back to FIG. 39, when the user 3104 opts into the messaging service (through selection of box 3304 of FIG. 41), one or more messages may be automatically generated and communicated to the user 3104 (e.g., via respective communications device(s) 114). For instance, the computing system 3102 may include a message generator 3136. The message generator 3136 can be or include instructions that, when executed by processor 3108, cause the processor 3108 to generate a message to communicate to the user 3104. The message generator 3136 can include instructions to transmit the generated message to the user 3104 via, for instance, the communications device 3114 of the computing system 3102 to the communications device 3114 of the user's 104 mobile device 3116 and/or personal computer 3118. The message generator 3136 can include instructions to identify a communications device 3114 associated with the user 3104 (e.g., by identifying the user file 3134 associated with the user 3104). The message generator 3136 can include instructions to communicate the generated message to the user 3104 upon one or more conditions, as will be discussed in further detail below. Accordingly, the various messages described herein may be communicated to the user's 104 mobile device 3116 and/or the user's 104 personal computer 3118. Various examples of messages will be discussed in turn below.

In some implementations, one or more messages that are generated via the message generator 3136 may be communicated to a notification center 3138. The notification center 3138 may be, for instance, a call center. The messages that are communicated to the notification center 3138 may be instructions to call a particular user 3104 at a particular time to deliver a verbal message, as will be discussed in further detail below.

In some embodiments, the message generator 3136 can include instructions for generating an appointment confirmation message. The message generator 3136 can include instructions to determine when a user 3104 has successfully reserved an appointment. The message generator 3136 can include instructions to automatically communicate (e.g., via respective communications devices 3114) the appointment confirmation message in response to the user 3104 successfully reserving the appointment. The appointment confirmation message may be or include a message that indicates that the user's 104 appointment has successfully been reserved. In some implementations, the appointment confirmation message may include a link, which the user 3104 may select, that causes the appointment to be automatically added to a calendar associated with the user 3104. For instance, the appointment confirmation message may include a plurality of links associated with different types of calendar software. The user 3104 may select the link corresponding to whichever type of calendar that is used by the user 3104. Upon selecting the appropriate link, the appointment may automatically be added to the user's 104 calendar. The appointment added to the user's 104 calendar may include contact information associated with the corresponding intraoral scanning site 3106, a location associated with the intraoral scanning site 3106, time, and an expected duration of the appointment (e.g., 30 minutes).

In some embodiments, the message generator 3136 can include instructions for generating one or more appointment reminder messages. The message generator 3136 can include instructions to determine a current time and an appointment time (e.g., the time of the user's 104 appointment at the intraoral scanning site 3106). The message generator 3136 can include instructions to compare a time difference between the current time and appointment time to a threshold time. If the difference in time is less than (or equal to) the threshold time, the message generator can include instructions to automatically generate the appointment reminder message.

Figure 45:
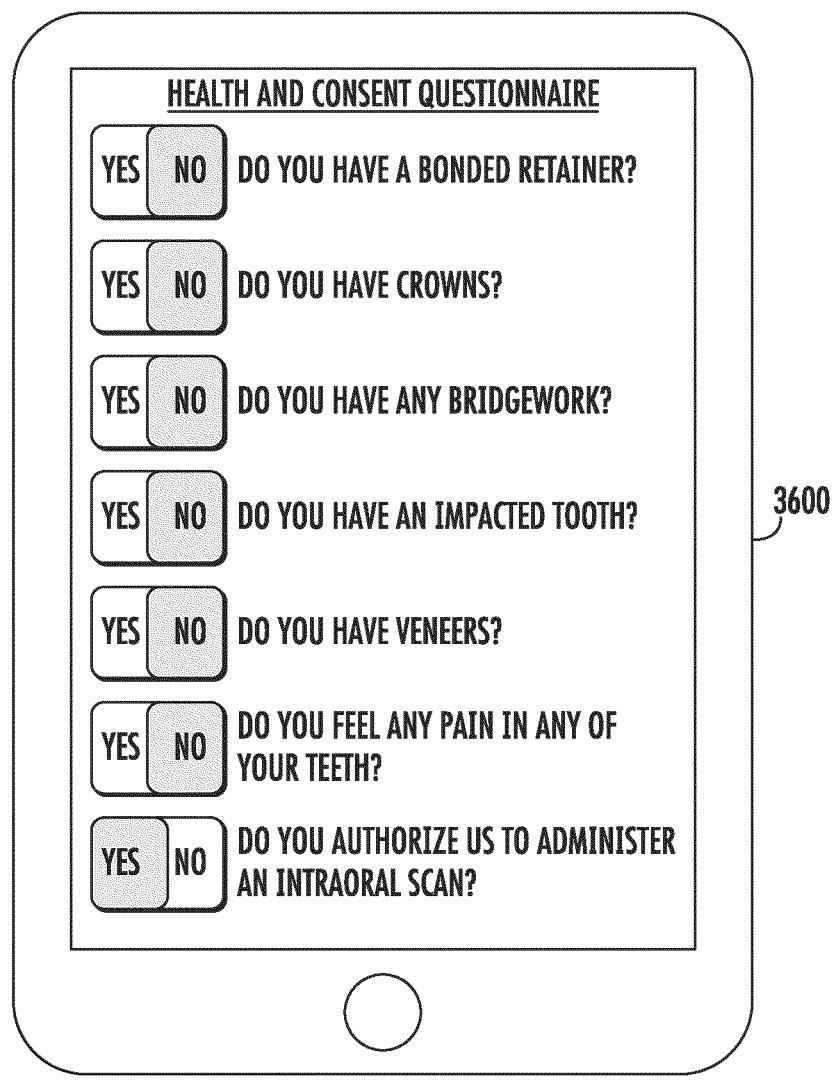
FIG. 45 shows a health and consent information screen displayed on a user device for enabling the user to provide health and consent information according to an exemplary embodiment.

In some implementations, the threshold time may be set based on a number of days (e.g., two days, three days, a week, etc.) until the user's 104 appointment. In implementations such as these, the appointment reminder message may be a message reminding the user 3104 that they have an upcoming appointment. The appointment reminder message may be generated when the user 3104 books an appointment well in advanced. Accordingly, where the user 3104 books an appointment for a number of days in advanced that is less than a threshold number of days (e.g., two days, three days, a week, etc.), the appointment reminder message may not be generated. As one non-limiting example, the user 3104 may book an appointment on a Monday. Where the user 3104 books the appointment for the next Friday, the user 3104 may be reminded of their appointment through generation of an appointment reminder message on the upcoming Wednesday. However, where the user 3104 books the appointment for the next day (e.g., Tuesday), the user 3104 may not receive an appointment reminder message. The appointment reminder message that is communicated to the user 3104 may include various information including, for instance, directions to the intraoral scanning site 3106, a phone number for the intraoral scanning site 3106, etc. Additionally, the appointment reminder message may include various information pertaining to the user's 104 appointment. For example, the appointment reminder message may include a health and consent questionnaire for the user 3104 to fill out. In some implementations, the health and consent questionnaire may have a plurality of Yes/No questions corresponding to various health-related conditions. The responses to the questions may be defaulted to "No", whereby the user 3104 may only need to change those answers to the questions that do apply to the user 3104. Referring briefly to FIG. 45, the user 3104 may be shown several questions which are defaulted to "No". The user 3104, however, may have an impacted tooth and an indicator on the health and consent questionnaire for an impacted tooth is defaulted to "No". Accordingly, the user 3104 may maintain all defaulted answers except for the question relating to impacted teeth, which the user 3104 may switch to answer "Yes." Such arrangements may expedite the overall process for the user's 104 experience at the intraoral scanning site 3106. As another example, the appointment reminder may include before-and-after pictures for previous customers (e.g., similar to those described above with reference to the results page). Such arrangements may increase excitement and anticipation of the appointment for the user 3104.

In some implementations, the threshold time may be set based on a location of the user 3104 (e.g., as determined based on data provided by the user's 104 mobile device 3116 and/or personal computer 3118) with respect to the location of the intraoral scanning site 3106. In implementations such as these, the appointment reminder message may be a message reminding the user 3104 to leave for their appointment. The threshold may be determined based on factors in addition to the location of the user 3104 including, for instance, a distance between the respective locations, traffic between the respective locations, weather, time of day, day of the week, etc. The appointment reminder message that is communicated to the user 3104 may include various information including, for instance, directions to the intraoral scanning site 3106, a phone number for the intraoral scanning site 3106, etc.

In some implementations, the message generator 3136 may include instructions to generate multiple appointment reminder messages. For instance, the message generator 3136 may generate a first appointment reminder message to remind the user 3104 that they have an upcoming appointment and a second appointment reminder message to indicate to the user 3104 that they should leave for their appointment (e.g., now, in 15 minutes, in one hour, etc.).

In some embodiments, the message generator 3136 can include instructions to identify specific users 3104 for voice messages. For instance, where the user 3104 does not provide credit card information 3402 (thus opting out of reserving the appointment), such information may be stored in the user file 3134. Where the user 3104 does not provide credit card information 3402, the message generator 3136 can include instructions to generate a prompt for a voice message to communicate to the notification center 3138. The prompt may instruct a person at the notification center to initiate a telephone call with the user 3104, in which the user 3104 will be informed about the overall process and experience at the intraoral scanning site 3106, and the user 3104 may provide one or more concerns regarding their smile. The call may be initiated by the person at the notification center a certain number of days prior to the user's 104 appointment (e.g., three days, five days, etc.). The person may annotate (or record) the conversation, and portions thereof may be saved to the user file 3134. In embodiments such as these, the voice message may increase user 3104 excitement for the appointment and increase the likelihood that the user 3104 shows up for their scheduled appointment.

Figure 44:
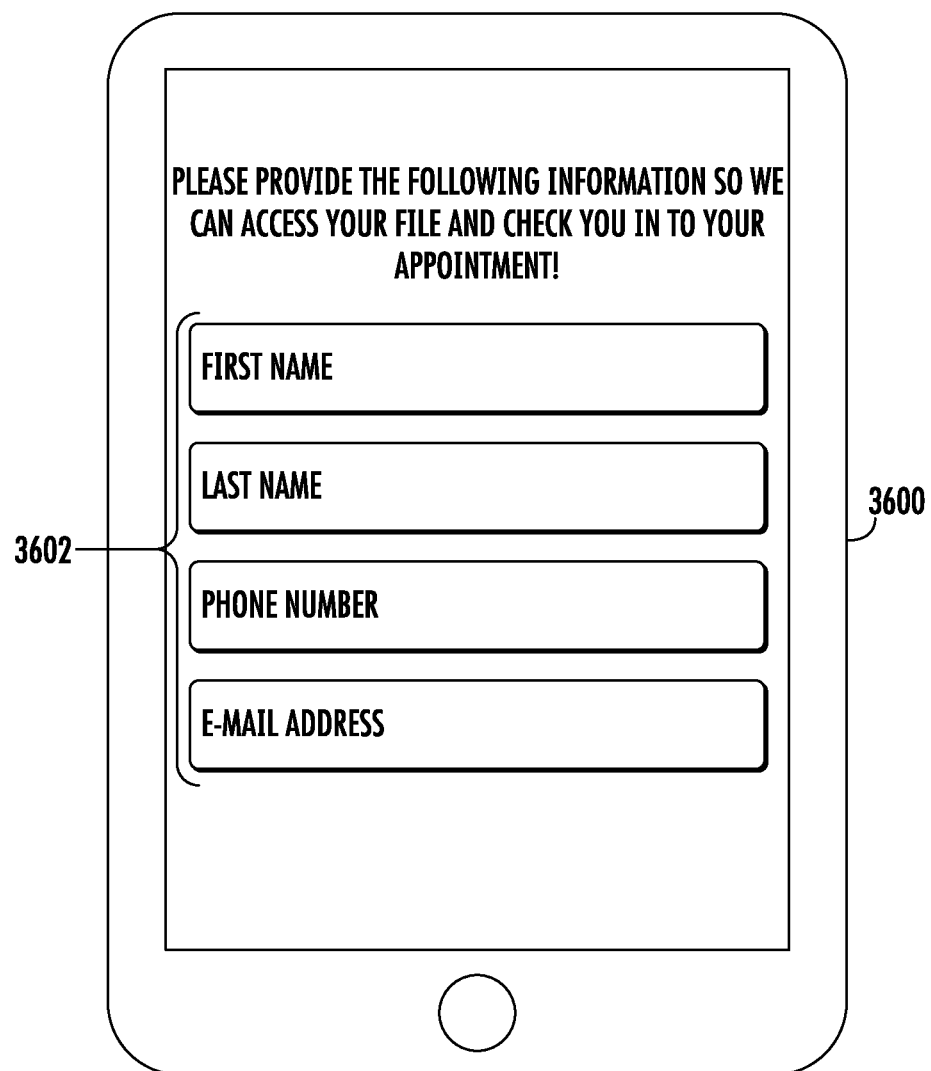
FIG. 44 shows a check-in screen displayed on a user device for enabling a user to check into an appointment according to an exemplary embodiment.

Referring now to FIG. 39 and FIG. 44, upon arrival at the intraoral scanning site 3106, the user 3104 may be presented with a user device 3600. The user device 3600 may be a tablet, for instance. The user 3104 may be requested to provide personal information 3602 (e.g., similar to the personal information 3302) for accessing the user file 3134. The processor 3108 may retrieve the user file 3134 associated with the user 3104 and check the user 3104 into their appointment. Where the user 3104 does not show up within a predetermined timeframe (e.g., at the start time of their appointment, within five minutes after the start time, 10 minutes after their start time, etc.) the processor 3108 may automatically indicate the user 3104 did not show up for their scheduled appointment. The processor 3108 may compare a time difference between the current time and the appointment start time to a predetermined timeframe. If the time difference exceeds the predetermined timeframe, the processor 3108 may automatically indicate the user 3104 did not show up for their scheduled appointment in the user file 3134. Additionally or alternatively, a receptionist may indicate that the user 3104 did not show up for their appointment in the user file 3134. In some embodiments, the message generator 3136 can include instructions for automatically generating a message to send to the user when the user is late for their appointment beyond a predetermined time frame (for instance, five minutes late). The message may ask the user to respond with whether they still plan on having an intraoral scan conducted, indicate that they do not need an appointment to receive their scan, prompt them to reschedule, etc.

In some instances, the intraoral scanning site 3106 may include a screen (e.g., of a television or other display system) that displays before-and-after pictures of customers who previously used aligners. The before-and-after pictures may be similar to those described above with reference to the results page. The before-and-after pictures may be displayed on a rolling basis. In instances such as these, consumer confidence may be increased by observing historical results.

Referring now to FIG. 39 and FIG. 45, the user file 3134 may include the health and consent questionnaire. Where the health and consent questionnaire was previously filled out by the user 3104 (e.g., as it was received in an appointment reminder message), the health and consent questionnaire may be saved to the user file 3134. However, where the health and consent questionnaire was not previously filled out by the user 3104 (e.g., the user 3104 never filled the questionnaire out or the questionnaire was never provided to the user 3104), the user 3104 may fill out the health and consent questionnaire via the user device 3600. In some embodiments, where the user 3104 switches an answer, a comment box is automatically generated and displayed to the user 3104 prompting the user 3104 to provide further details. For instance, where the user indicates that they are experiencing pain in their teeth, a comment box is automatically generated and displayed on the display of the user device 3600. The user may provide an input, via the comment box, to elaborate on the pain in their teeth. While two examples of when the health and consent questionnaire are provided (e.g., following a reservation and following an appointment check-in but prior to the intraoral scan), the health and consent questionnaire may be provided to the user 3104 to complete at any time throughout the scanning process after they arrive at the scanning location, such as during a break in procedures, following completion of the intraoral scan, etc. Accordingly, the present disclosure is not limited to any particular arrangement regarding when the health and consent questionnaire is completed by the user 3104.

As shown in FIG. 45, the user device 3600 may present the health and consent questionnaire to the user 3104. As discussed above, the health and consent questionnaire may have a plurality of Yes/No questions corresponding to various health-related conditions. In some implementations, at least some of the questions for the health and consent questionnaire may be defaulted to a set response. For instance, the health-related questions for the questionnaire may be defaulted to "NO", whereas the consent-related questions for the questionnaire may be defaulted to "YES". In other instances, all of the questions may be defaulted to "NO". The user 3104 can modify the responses to all the questions as needed. For instance, the user 3104 may have bridgework and a question inquiring about whether the user 3104 has bridgework is defaulted to "No". Accordingly, the user 3104 may maintain the default answers to all the questions except for the question pertaining to bridgework. The user 3104 may manually switch this answer to "Yes." In each of these implementations, the user's 104 experience at the intraoral scanning site 3106 may be improved by expediting the health and consent questionnaire.

Following check-in and providing the responses to the health and consent questionnaire, the user 3104 may be directed to a room where the user 3104 will receive their intraoral scan. A technician at the scan shop 3106 may administer the intraoral scan. The technician may administer the intraoral scan using, for instance, an iTero® scanner. As the technician administers the intraoral scan, the intraoral scanner may produce data which is visually represented on a display. The data may correspond to a three-dimensional scan of the user's 104 mouth. In some embodiments, the technician may administer the intraoral scan in a predetermined position. For instance, the technician may be instructed to administer the intraoral scan from over the user's 104 shoulder with the display in the field of view of the user 3104. Accordingly, as the intraoral scanner generates data that is visually represented on the display, both the user 3104 and technician may be able to observe the display. Such arrangements and instructions may enhance the user's 104 experience by engaging the user 3104 in the scanning process.

In some embodiments, the administration of the intraoral scan may be recorded for quality assurance purposes. For instance, the room in which the user 3104 has the intraoral scan administered may have a camera. The user 3104 may approve or deny the recording. In some instances, the user 3104 may be incentivized to approve the recording by, for instance, one free set of aligners or one free set of retainers.

In some embodiments, the user 3104 may be shown a simulated movement of the user's teeth from the starting position (e.g., as represented by the three-dimensional scan) to a simulated final position. Such capabilities presently exist through use of the iTero® scanner.

Following administration of the intraoral scan, in some embodiments, a quality control technician may review and approve the intraoral scan. The quality control technician may be located at the intraoral scanning site 3106. Additionally or alternatively, the quality control technician may be located remotely. The quality control technician may be a manager or other guide who has the authority to approve (or not approve) the intraoral scan. Where the quality control technician does not approve of the intraoral scan, the quality control technician may highlight particular areas on the intraoral scan that need to be re-scanned. The quality control technician may also approve some or all of the information provided by the user 3104 (e.g., the personal information 3302, the health and consent information provided in the health and consent questionnaire, various other information such as shipping information, etc.). In implementations such as these, the quality control technician may ensure that subsequent visits to the intraoral scanning site 3106 or unnecessary calls to the user 3104 are avoided by collecting all necessary information during a single appointment of the user 3104.

In some embodiments, following administration of the intraoral scan, the technician may take one or more photographs of the user's 104 mouth. The technician may take the photographs of the user's 104 upper and lower jaw (in some instances with a smile spreader). The technician may take a head-on photograph of the user's 104 smile. The technician may take the one or more photographs using a digital camera. Additionally or alternatively, the technician may take the one or more photographs using a camera of the user device 3600. In each of these implementations, the photographs may be an initial set of photos that is used for compliance checks. The photographs may be saved to the user file 3134.

Once the quality control technician approves of the intraoral scan (and photographing), the user 3104 may leave the room where the user 3104 received their intraoral scan. The user may go to, for instance, a waiting area or front desk area. At the front desk area, the user 3104 may be shown or given various products. For instance, the user 3104 may be shown what the aligners generally look like (e.g., substantially transparent, translucent, etc.). The user 3104 may also be shown the packaging in which the aligners are delivered and the corresponding instruction manual. The user 3104 may be provided with various dental-related items. For instance, the user 3104 may be provided with lip balm, teeth whitening kits, a tote bag, etc. Each of these examples may further increase the likelihood of the user 3104 purchasing aligners that are custom to the user's 104 teeth. In some embodiments, instead of receiving products at a front desk area, the user 3104 may be shown or given various products in the room where they received the intraoral scan. In some embodiments, the user 3104 may be shown the aligners/packaging prior to receiving the intraoral scan (e.g., at check-in), during a break, etc.

In some embodiments, the user 3104 may be presented with a fast track option for generating a set of aligners from the intraoral scan. The fast track option may be a form that is filled out by the user 3104, may be an oral agreement from the user, etc. The fast track option may authorize a provider of the aligners to automatically generate the aligners once the treatment plan (or the final teeth position) for the user 3104 is approved by a doctor (e.g., a dentist, an orthodontist, etc.).

The user 3104 may be prompted to pay at the time of the intraoral scan (or set up a payment plan at the time of the intraoral scan). Once the user 3104 pays (or sets up the payment plan), the user 3104 may authorize fast tracking the generation of the aligners. In implementations such as these, the user 3104 may not be required to authorize the treatment plan. Rather, the treatment plan may be shown in the user portal, as will be discussed in greater detail below. Additionally, once the treatment plan is approved by the doctor, the treatment plan may be automatically used for generating the aligners and automatically uploaded to the user portal.

In some embodiments, the doctor (e.g., the dentist, orthodontist, etc.) may approve of the treatment plan following the doctor seeing the user via a video conference or a video of the user. For instance, the doctor may "see" the user remotely prior to approving the treatment plan. In still other embodiments, the doctor may approve of the treatment plan without the video conference or the video of the user. In each of these embodiments, the doctor may approve of the treatment plan for the user without having to physically see the user in person. Accordingly, the user may not be inconvenienced with a trip to a doctor's office, which may also save time for the user.

Where the user 3104 does not authorize fast tracking the generation of the aligners, the user 3104 may authorize the treatment plan once the treatment plan is sent to the user 3104 via the user portal. Following authorization of the treatment plan, the aligners may be generated and sent to the user 3104. Additionally, following authorization of the treatment plan, the user 3104 may then be prompted to pay for the aligners (or sign up for a payment plan).

In some embodiments, the treatment plan may be generated by a dental professional using a computing system at a treatment plan site. The treatment plan site may be separate from the intraoral scan sites, the fabrication site, etc. In other embodiments, the treatment plan site may be the same as the intraoral scan site and/or the fabrication site. Accordingly, two or more of these sites may be consolidated into one site.

The treatment plan may be generated by manipulating individual teeth in the three-dimensional representation of the user's mouth. For instance, the dental professional may manipulate one or more teeth of the user's mouth (as represented in the three-dimensional data) from a starting position (at the time of the intraoral scan) to an ending position (following treatment). Following the teeth being moved to the ending position, the treatment plan may automatically be generated (e.g., by a computer or computing system) in accordance with a set of rules. The set of rules may include rules which constrict an amount of movement of a single tooth between two sequential aligners (for instance, 3.00 mm). Following the treatment plan being generated, various models (e.g., positive molds of the user's dentition) may be generated which correspond to the position of the teeth at various intervals between the starting and ending position. The aligners may then be generated by thermoforming a polymer material to each of the various models (with a first aligner corresponding to the starting position of the user's teeth in the user's dentition, the second [and subsequent] aligner corresponding to an intermediate position[s], and the final aligner corresponding to the final position of the user's teeth in the user's dentition).

Following generation of the aligners, all aligners associated with the treatment plan may be sent to the user 3104. In some implementations, the aligners may be generated and sent to the user 3104 in packaging similar to the packaging described in U.S. Patent Application Ser. No. 62/522,847, filed on Jun. 21, 2017, titled "DENTAL IMPRESSION KITS AND METHODS THEREFOR," U.S. patent application Ser. No. 15/725,430, filed on Oct. 5, 2017 and having the same title, and U.S. Patent Application Ser. No. 62/648,229, filed on Mar. 26, 2018 and having the same title, each of which are incorporated by reference in their entirety as noted herein.

Following the user 3104 having their intraoral scan administered at the scan shop 3106, the user 3104 may receive one or more messages generated via the message generator 3136. Accordingly, in some embodiments, the message generator 3136 can include instructions for generating and communicating one or more messages to the user 3104 following the user's 104 appointment.

In some implementations, the message generator 3136 can include instructions to generate a message including various surveys and/or questionnaires. These surveys may be used for evaluating the user's 104 experience at the intraoral scanning site 3106. In some implementations, the surveys may solicit the user 3104 for a review on a customer review website such as Yelp®, Google®, etc. Additionally, where the user 3104 receives a whitening kit at their appointment, the message generated via the message generator 3136 may include whitening tips for the user 3104. In each of these implementations, the messages generated via the message generator 3136 may be used as feedback for subsequent user's appointments, and to enhance the experience for the user 3104.

In some implementations, the message generator 3136 can include instructions for generating various messages specifically when a user 3104 does not attend their appointment. For instance, when the user file 3134 indicates the user 3104 did not show up for their appointment, the message generator 3136 can include instructions for automatically generating a message including a survey for evaluating reasons why the user 3104 did not showed up for their appointment. The survey generated in these implementations may solicit the user 3104 to provide suggestions of what the intraoral scanning site 3106 (or website) could do differently. The survey generated in these implementations may also solicit the user 3104 to provide information as to how the user 3104 would like to be contacted in the future (e.g., via phone call, text message, email, etc.). In some instances, the message generated via the message generator 3136 may include an indication to the user 3104 that the user 3104 does not require an appointment for an intraoral scan and that the user can show up at an intraoral scanning site 3106 any time during business hours (e.g., that walk-ins are welcome). In each of these implementations, the messages are provided to the user 3104 when the messages may increase the likelihood of the user 3104 scheduling or otherwise visiting the intraoral scanning site 3106, and may assist in improvements to the overall experience for other users.

Additionally, where the user 3104 misses their appointment, in some instances, the user 3104 may be provided a free at-home impression kit (similar to those described in U.S. Patent Application Ser. No. 62/522,847 and U.S. patent application Ser. No. 15/725,430). The at-home impression kit may be sent to the user 3104 via first class mail. For instance, when the user file 3134 indicates the user 3104 did not show up for the appointment, the message generator 3136 can include instructions to automatically generate a message to the user 3104 that indicates that an at-home impression kit will be sent at no charge to the user 3104. Additionally, the message generator 3136 can include instructions to generate a prompt that is transmitted to, for instance, a processing or shipping warehouse. The prompt may include an address or shipping label and instructions to send an at-home impression kit to the user 3104 at the address.

Figure 46:
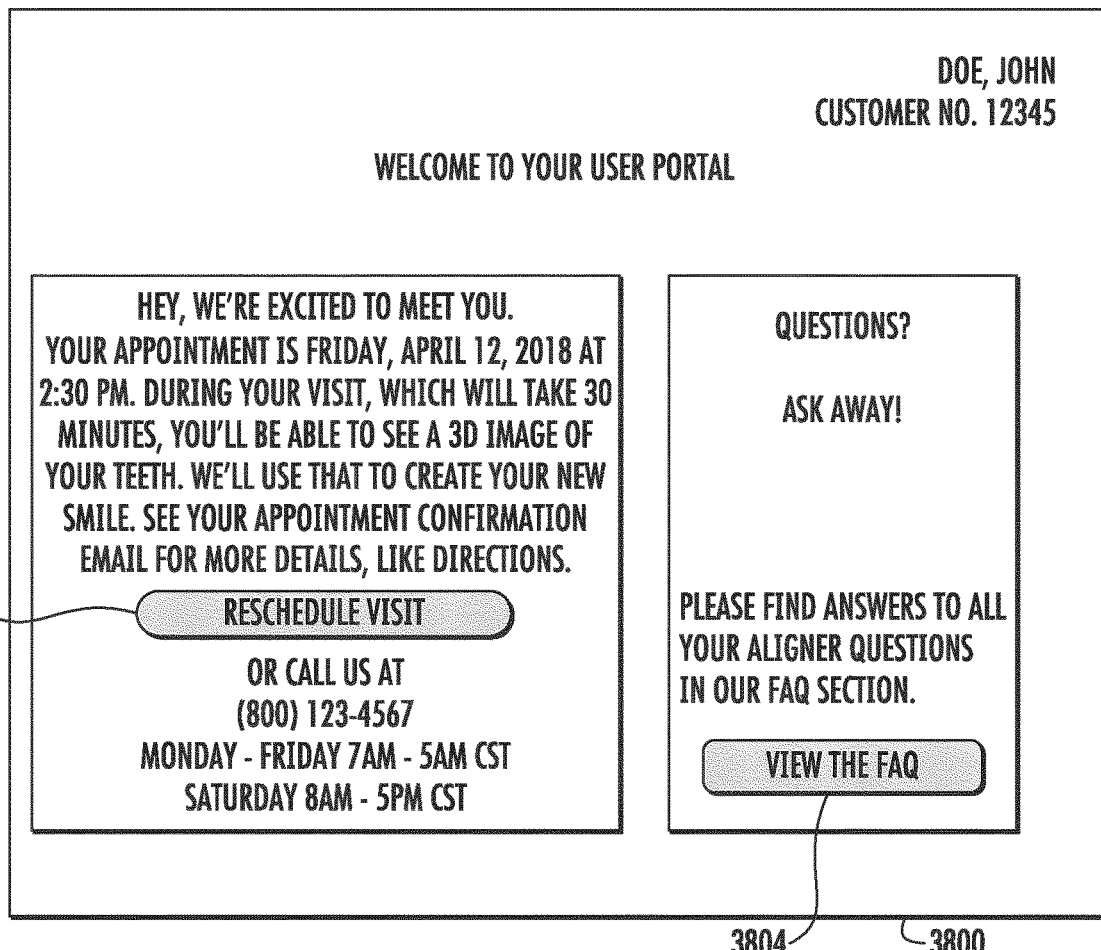
FIG. 46 is a user portal screen displayed to the user prior to the user's appointment according to an exemplary embodiment.

Referring now to FIG. 39 and FIG. 46, a user portal is generated for the user 3104. Specifically shown in FIG. 46 is an example user portal 3800 associated with the user 3104. The example user portal 3800 shown in FIG. 46 is generated prior to the user's 104 appointment. The appointment management system 3100 may include a portal manager 3140. The portal manager 3140 may be or include instructions, that when executed by the processor 3108, cause the processor 3108 to generate/modify/change/manage one or more aspects of the user portal 3800. As shown, the user portal 3800 may include a brief overview of what to expect at the user's 104 appointment. The user portal 3800 may include a button 3802 to reschedule the user's 104 appointment. The button 3802 may direct the user 3104 to a page similar to reservation page 3200. Additionally, the user portal 3800 may include a button 3804 to view a Frequently Asked Questions (FAQ) page providing answers to questions that the user 3104 may have.

Figure 47:
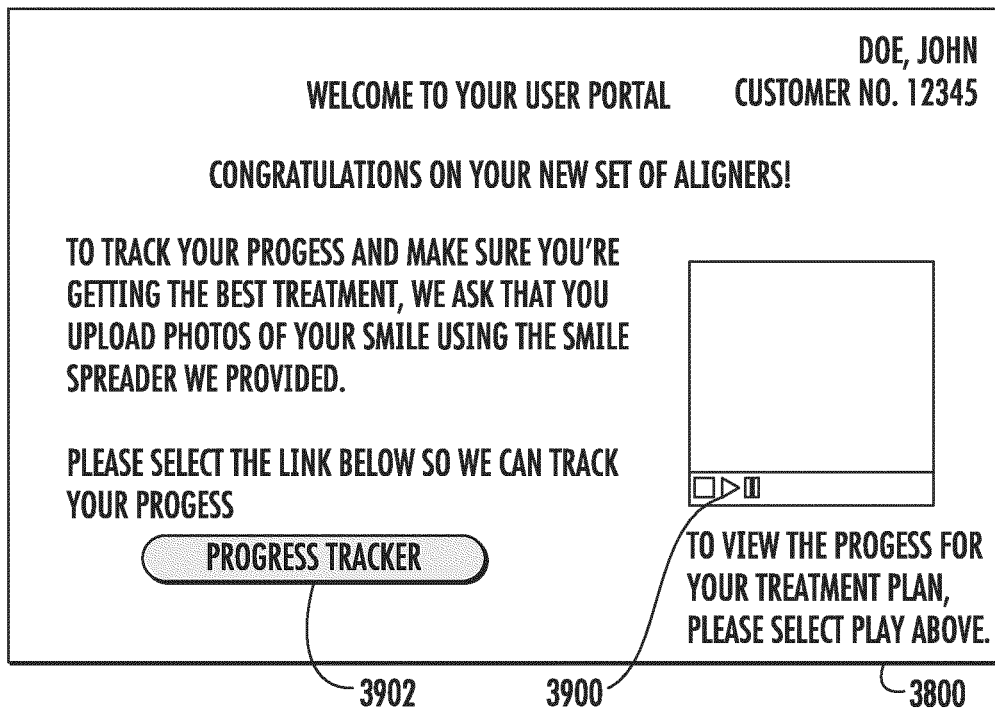
FIG. 47 is an example of a user portal screen displayed to the user following the user's appointment according to an exemplary embodiment.

Referring now to FIG. 39 and FIG. 47, the portal manager 3140 may include instructions to modify the user portal 3800 following the user's 104 appointment. For instance, as shown in FIG. 47, the user portal 3800 is generated following the user's 104 appointment. The user portal 3800 shown in FIG. 47 may include a visual representation (shown as a video) of the user's 104 treatment plan. The visual representation may show changes in the user's 104 smile as the user 3104 progresses through various stages of the treatment plan. The visual representation may be a series of photos, a video, etc. The user 3104 may be able to view the visual representation through selection of a button 3900 (e.g., play button).

Additionally, the user 3104 may be required (or requested) to provide progress information. As will be discussed in greater detail below, the progress information provided by the user 3104 may be used for evaluating compliance and issuing a mid-course correction.

The user 3104 may select a button 3902 for providing progress information. The user 3104 may be required to provide progress information at various stages along the treatment plan. For instance, the user 3104 may be required to provide progress information at the outset of the treatment plan, as each aligner is used, following 90 days from the outset of the treatment plan, and/or other stages in the treatment plan. In some implementations, the appointment management system 3100 may issue reminders to the user 3104 for providing the progress information. For instance, the message generator 3136 and/or portal manager 3140 can include instructions to automatically generate one or more messages to communicate to the user 3104 at various points throughout the treatment plan. As one example, when the aligners are received by the user 3104 (e.g., as detected by a delivery notification), the delivery notification may be indicated in the user file 3134. When the user file 3134 indicates the delivery notification, the message generator 3136 and/or portal manager 3140 can include instructions to automatically generate one or more messages for the user 3104 instructing the user 3104 to provide initial progress data. When uploaded, the portal manager 3140 can include instructions to store the initial progress data in the user file 3134 as a baseline. The message generator 3136 and/or portal manager 3140 may include instructions to generate subsequent messages reminding the user 3104 to upload progress data at various stages of the treatment plan, as described above. The message generator 3136 and/or portal manager 3140 can include instructions to identify a send date upon which the message corresponding to the initial progress data was communicated to the user 3104. Additionally, the message generator 3136 and/or portal manager 3140 can include instructions to identify a current date. Based on a difference between the send date and the current date, the processor 3108 may generate subsequent messages based on the instructions from the message generator 3136 (and/or portal manager 3140). Similarly, the message generator 3136 and/or portal manager 3140 can include instructions to generate messages directing the user 3104 to change which aligners they are using (e.g., directing the user 3104 to stop using a first set of aligns and to instead use a second set of aligners, directing the user 3104 to stop using a third set of aligners and instead use the second set of aligners, to stop using the aligners altogether and to wait for new aligners to be sent to the user 3104, etc.). Such messages may be generated similar to the messages for providing progress data.

Figure 48:
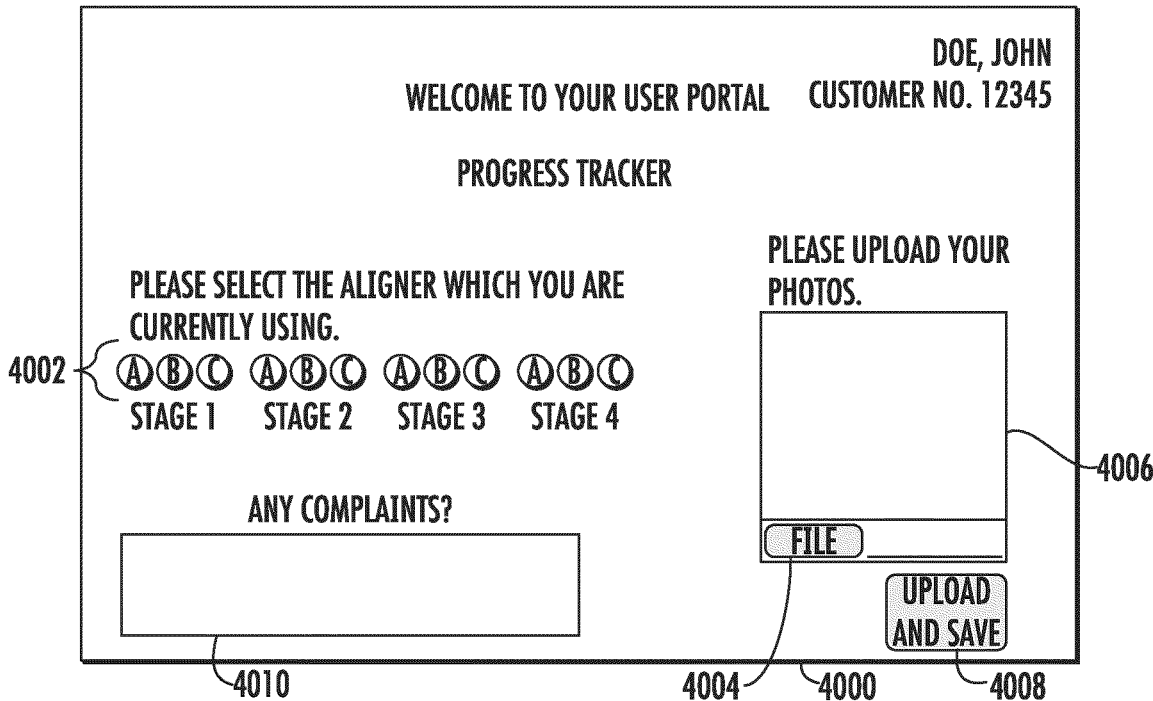
FIG. 48 is an example of a user portal screen displaying a progress tracker according to an exemplary embodiment.

Referring now to FIG. 39 and FIG. 48, upon selection of button 3902, the portal manager 3140 can include instructions to direct the user 3104 to a progress tracker page 4000 within the user portal 3800. Within the progress tracker page 4000, the user 3104 is prompted to indicate which aligner the user 3104 is currently using (e.g., through selection of a corresponding button 4002). Additionally, the user 3104 is prompted to upload photos of the user's 104 smile. The user 3104 may be instructed (e.g., either on the user portal 3800, the progress tracker 4000, or separate instruction manual) on how to capture photos. For instance, the user 3104 may be instructed to capture photos while using a smile spreader (e.g., a device positioned in the user's 104 mouth intended to push back the user's 104 lips and expose a greater area of the user's 104 teeth). The user 3104 may be instructed to position the smile spreader in the user's 104 mouth and capture images at various angles. The user 3104 may be instructed to capture an image of the user's 104 teeth head-on while biting down. The user 3104 may be instructed to capture an image of the user's 104 lower jaw while opening the user's 104 mouth. The user 3104 may be instructed to capture an image of the user's 104 upper jaw while opening the user's 104 mouth. The user 3104 may be instructed to capture additional/alternative images of the user's 104 teeth. Each of these images may be uploaded by the user 3104 using button 4004. Upon selection of button 4004, the user 3104 may be prompted to search for and locate the image to upload. The image may be previewed (e.g., in display box 4006) once the user 3104 locates the file. The user 3104 may then select an upload button 4008 to upload the images to the user portal 3800. When the images are uploaded, the portal manager 3140 can include instructions to automatically add these images to the user file 3134.

The user 3104 may provide comments regarding the progress or fit of the aligners in comments box 4010. For instance, the user 3104 may indicate that the user 3104 is not satisfied with the progress of realigning the user's 104 teeth or how the user's 104 smile looks. As another example, the user 3104 may indicate that the aligners do not fit or are uncomfortable. Each of these indications may indicate that the user 3104 may require a mid-course correction. As used herein, a mid-course correction is defined as a new treatment plan developed for the user 3104 following an indication that the current treatment plan is no longer desirable for the user 3104. Accordingly, the user 3104 receives a new intraoral scan, a new set of aligners, etc. In this regard, no cross-reference is made between the first treatment plan and the second treatment plan. However, in some implementations, the mid-course correction comprises receipt of at least one new set of aligners, which may be created for the user 3104 following new intraoral scan or new impressions to be made of the user's 104 teeth. In some implementations, the mid-course correction may be free to the user 3104. For instance, as discussed below, the mid-course correction may be free following a compliance check indicating that the user 3104 is correctly following the treatment plan.

The compliance check may be a review of the progress data provided by the user (e.g., via progress tracker 4000). In some implementations, following the user 3104 uploading any comments via comments box 4010, the portal manager 3140 may include instructions to automatically flag the user file 3134 and communicate the file to a professional terminal 3142. The professional terminal 3142 may be a computer associated with one or more professionals (e.g., doctors, dentists, orthodontists, etc.). The professional terminal 3142 may display the user file 3134 including the images uploaded by the user 3104 and the current aligner which is being used by the user 3104. The user file 3134 may be evaluated by the professionals to determine whether the user 3104 is progressing according to the treatment plan, whether the user 3104 is following the treatment plan as instructed, etc. Where the user 3104 is not following the treatment plan as instructed, the user file 3134 may be flagged as not being in compliance. Where the user 3104 is following the treatment plan but is not progressing according to the treatment plan, portal manager 3140 may flag the user file 3134 for a mid-course correction. Where the user file 3134 is flagged as not being in compliance, the user 3104 may be required to pay for the mid-course correction. However, where the user 3104 is following the treatment plan, the mid-course correction may be offered to the user 3104 for free.

In some implementations, when the user 3104 is following the treatment plan as instructed and progresses through the treatment plan, the message generator 3136 and/or portal manager 3140 may include instructions to automatically generate a message (and corresponding flag in the user file 3134) indicating that the user 3104 is eligible for a free dental check-up and cleaning at a dental clinic or associated dental office.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, orientations, etc.). By way of example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on memory or other machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products or memory comprising machine-readable media for carrying or having machine-executable instructions or data structures stored thereon. Such machine-readable media may be any available media that may be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, by way of example, instructions and data which cause a general purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision step.

What is claimed is:

1. A method of fabricating aligners for repositioning one or more teeth of a user, the method comprising:

providing, by a management system, a user interface for selecting a patient-intake option from a first patient-intake option and a second patient-intake option, the first patient-intake option comprising scheduling an intraoral scan, the second patient-intake option comprising receiving a dental impression kit for creating dental impressions;

receiving, by the management system, a request to ship the dental impression kit, the dental impression kit including a container containing a dental assembly and a dental appliance, the dental assembly including one or more dental trays and putty, the putty provided in an amount to be positioned in the one or more dental trays for creating the dental impressions, the dental appliance configured to hold open the user's upper and lower lips simultaneously to permit visualization of the user's teeth and further configured to continue holding open the user's upper and lower lips in a hands-free manner after being positioned at least partially within the user's mouth;

scheduling, by the management system, the shipment of the dental impression kit based on the request;

generating and causing transmission of, by the management system, a message to a device of the user, the message including a confirmation confirming the shipment of the dental impression kit;

conducting, using a scanner, a scan of the dental impressions created by the user to generate three-dimensional data of the mouth of the user;

fabricating, using fabrication equipment, a plurality of aligners based on a treatment plan, the treatment plan generated for the user based on the three-dimensional data, the plurality of aligners specific to the user and being configured to reposition one or more teeth of the user in accordance with the treatment plan; and causing all of the plurality of aligners to be sent to the user at once, wherein the treatment plan is approved by an approving dentist or orthodontist without the approving dentist or orthodontist having physically seen the user, wherein the user receives orthodontic treatment without ever having physically seen the approving dentist or orthodontist.

2. The method of claim 1, wherein generating and causing transmission of the message comprises generating and causing transmission of a plurality of messages to the device of the user including the confirmation confirming the shipment of the dental impression kit.

3. The method of claim 2, wherein the message is a first message, and wherein the plurality of messages include a second message that is caused to be transmitted following the shipment, wherein the second message is a delivery notification of the dental impression kit.

4. The method of claim 1, wherein the treatment plan is generated at a treatment plan site, wherein the plurality of aligners are fabricated at a fabrication site, and wherein an intraoral scanning site, the treatment plan site, and the fabrication site are separate from one another.

5. The method of claim 1, further comprising:
receiving, by a fabrication computing system, data corresponding to the treatment plan generated based on the three-dimensional data of the mouth of the user;
generating, by a three-dimensional printer, a plurality of positive molds of a dentition of the user based on the treatment plan, wherein each positive mold of the plurality of positive molds correspond with a specific step of the treatment plan; and
thermoforming, using thermoforming equipment, polymer material to each of the plurality of positive molds to fabricate the plurality of aligners.

6. The method of claim 1, wherein the message is caused to be transmitted to at least one of a mobile application, an electronic web-based account, or a phone number of the user.

7. The method of claim 1, further comprising:
causing transmission of the three-dimensional data to a treatment plan computing system; and
receiving, from the treatment plan computing system, the treatment plan for the user generated based on the three-dimensional data, the treatment plan defining movement of the one or more teeth of the user from a starting position at the time of the intraoral scan to an ending position following treatment using the plurality of aligners.

8. The method of claim 1, wherein all of the plurality of aligners are sent directly to the user at once.

9. A system for fabricating aligners for repositioning one or more teeth of a user, the system comprising:
a management system configured to:
provide a user interface for selecting a patient-intake option from a first patient-intake option and a second patient-intake option, the first patient-intake option comprising scheduling an intraoral scan, the second patient-intake option comprising receiving a dental impression kit for creating dental impressions;
receive a request to schedule shipment of a dental impression kit to a user, the dental impression kit including a container containing a dental assembly and a dental appliance, the dental assembly including one or more dental trays and putty, the putty provided in an amount to be positioned in the one or more dental trays for creating the dental impressions, the dental appliance configured to hold open the user's upper and lower lips simultaneously to permit visualization of the user's teeth and further configured to continue holding open the user's upper and lower lips in a hands-free manner after being positioned at least partially within the user's mouth;
schedule the shipment of the dental impression kit to the user based on the request;
generate and cause transmission of a message to a device of the user, the message including a confirmation confirming the shipment of the dental impression kit; and
fabrication equipment configured to fabricate a plurality of aligners based on a treatment plan generated using three-dimensional data captured by a scanner configured to scan the dental impressions created by the user using the dental impression kit, the plurality of aligners specific to the user and being configured to reposition one or more teeth of the user in accordance with the treatment plan;
wherein all of the plurality of aligners are sent to the user at once, wherein the treatment plan is approved by an approving dentist or orthodontist without the approving dentist or orthodontist having physically seen the user, wherein the user receives orthodontic treatment without ever having physically seen the approving dentist or orthodontist.

10. The system of claim 9, wherein the management system is configured to generate and cause transmission of a plurality of messages to the device of the user, and wherein one of the plurality of messages is the confirmation confirming the shipment of the dental impression kit.

11. The system of claim 9, wherein the treatment plan is generated at a treatment plan site, wherein the plurality of aligners are fabricated at a fabrication site, and wherein the treatment plan site and the fabrication site are separate from one another.

12. The system of claim 9, wherein the management system is configured to generate and cause transmission of a plurality of messages to the device of the user, and wherein the plurality of messages include a first message caused to be transmitted upon shipment of the dental impression kit, and a second message caused to be transmitted subsequent to receipt of the dental impressions from the user, the second message including a representation based on the treatment plan generated for the user.

13. The system of claim 9, wherein the management system is configured to generate and cause transmission of a plurality of messages to the device of the user, and wherein the plurality of messages include a first message caused to be transmitted upon shipment of the dental impression kit, and a second message caused to be transmitted subsequent to receipt of the dental impressions from the user, the second message including an indication that the treatment plan has been generated, that the treatment plan has been approved by the approving dentist or orthodontist, and that the plurality of aligners will be sent to the user, wherein the user pre-approved the treatment plan.

14. A method of fabricating aligners for repositioning one or more teeth of a user, the method comprising:
   providing, by a management system, a user interface for selecting a patient-intake option from a first patient-intake option and a second patient-intake option, the first patient-intake option comprising scheduling an intraoral scan, the second patient-intake option comprising receiving a dental impression kit for creating dental impressions;
   receiving, by the management system, a request to schedule delivery of a dental impression kit to a user, the dental impression kit including a container containing a dental assembly and a dental appliance, the dental assembly including one or more dental trays and putty, the putty provided in an amount to be positioned in the one or more dental trays for creating the dental impressions, the dental appliance configured to hold open the user's upper and lower lips simultaneously to permit visualization of the user's teeth and further configured to continue holding open the user's upper and lower lips in a hands-free manner after being positioned at least partially within the user's mouth;
   scheduling, by the management system, the shipment of the dental impression kit to the user based on the request;
   generating and causing transmission of, by the management system, a message to a device of the user, the message including a confirmation confirming the shipment of the dental impression kit to the user;
   fabricating, using fabrication equipment, a plurality of aligners based on a treatment plan generated for the user based on three-dimensional data obtained by a scanner from the dental impressions created by the user using the dental impression kit, the plurality of aligners specific to the user and being configured to reposition one or more teeth of the user in accordance with the treatment plan; and
   causing all of the plurality of aligners to be sent to the user at once, wherein the treatment plan is approved by an approving dentist or orthodontist without the approving dentist or orthodontist having physically seen the user, wherein the user receives orthodontic treatment without ever having physically seen the approving dentist or orthodontist.

15. The method of claim 14, wherein all of the plurality of aligners are sent directly to the user at once.

16. The method of claim 14, wherein the treatment plan is generated at a treatment plan site, wherein the plurality of aligners are fabricated at a fabrication site, and wherein the treatment plan site and the fabrication site are separate from one another.

17. The method of claim 14, wherein the message is a first message, the method further comprising:
   generating and causing transmission of, by the management system, a second message to the device of the user following receiving the dental impressions from the user, the second message including information relating to the treatment plan generated for the user.

18. The method of claim 17, wherein the information included in the second message includes a representation based on the treatment plan generated for the user and to be approved by the user.

19. The method of claim 17, wherein the information included in the second message includes an indication that the treatment plan has been generated, that the treatment plan has been approved by the approving dentist or orthodontist, and that the plurality of aligners will be sent to the user, wherein the user pre-approved the treatment plan.

20. A method of fabricating aligners for repositioning one or more teeth of a user, the method comprising:
   providing, by a management system, a user interface for selecting a patient-intake option from a first patient-intake option and a second patient-intake option, the first patient-intake option comprising scheduling an intraoral scan, the second patient-intake option comprising receiving a dental impression kit for creating dental impressions;
   conducting, using a scanner, a scan of a dental impression created by a user using a dental impression kit delivered to the user to obtain three-dimensional data of a mouth of the user, the dental impression kit including a container containing a dental assembly and a dental appliance, the dental assembly including one or more dental trays and putty, the putty provided in an amount to be positioned in the one or more dental trays for creating the dental impression, the dental appliance configured to hold open the user's upper and lower lips simultaneously to permit visualization of the user's teeth and further configured to continue holding open the user's upper and lower lips in a hands-free manner after being positioned at least partially within the user's mouth;
   causing generation of, by a treatment plan computing system located at a treatment plan site separate from a scanning site that includes the scanner without the user being present at the treatment plan site, a treatment plan for the user based on the three-dimensional data;
   receiving an indication of an approval of the treatment plan by an approving dentist or orthodontist, wherein the approval is received without the approving dentist or orthodontist having physically seen the user;
   receiving, by a fabrication computing system located at a fabrication site separate from the scanning site and the treatment plan site without the user or the approving dentist or orthodontist being present at the fabrication site, the treatment plan from the treatment plan computing system;
   fabricating, at the fabrication site, a plurality of aligners based on the treatment plan, the plurality of aligners specific to the user and being configured to reposition one or more teeth of the user in accordance with the treatment plan; and
   sending all of the plurality of aligners from the fabrication site at once to the user, wherein the user receives orthodontic treatment without ever having physically seen the approving dentist or orthodontist.

21. The method of claim 20, wherein the approval of the treatment plan is received from the approving dentist or orthodontist after the approving dentist or orthodontist sees the user via a video of the user or via a videoconference with the user.

22. The method of claim 20, wherein causing generation of the treatment plan comprises:
- transmitting, to the treatment plan computing system, the three-dimensional data; and
- receiving, from the treatment plan computing system, the treatment plan for the user generated based on the three-dimensional data, the treatment plan defining movement of the one or more teeth of the user from a starting position at the time the dental impression was formed to an ending position following treatment using the plurality of aligners.

23. The method of claim 20, wherein the approval by the approving dentist or orthodontist is a first approval, the method further comprising:
- responsive to receiving the first approval, providing data indicative of the treatment plan to a device of the user; and
- receiving a second approval of the treatment plan, wherein the second approval of the treatment plan is received from the device of the user following the first approval being received from the approving dentist or orthodontist;
- wherein fabricating the plurality of aligners is performed responsive to receiving the first approval and the second approval of the treatment plan.

24. The method of claim 23, wherein the second approval of the treatment plan is received from the device of the user without the user ever having physically seen the approving dentist or orthodontist.

25. The method of claim 20, wherein the treatment plan is generated by manipulating, by the treatment plan computing system, one or more teeth in the three-dimensional data from a starting position at the time the dental impression was formed to an ending position.

26. The method of claim 20, wherein fabricating the plurality of aligners comprises:
- generating, by a three-dimensional printer, a plurality of positive molds of a dentition of the user based on the treatment plan, wherein each positive mold of the plurality of positive molds correspond with a specific step of the treatment plan; and
- thermoforming, using thermoforming equipment, polymer material to each of the plurality of positive molds to fabricate the plurality of aligners.

27. The method of claim 20, further comprising:
- generating and causing transmission of a first message to a device of the user confirming shipment of the dental impression kit to the user; and
- generating and causing transmission of a second message to the device of the user confirming delivery of the dental impression kit to the user.

28. The method of claim 20, wherein sending all of the plurality of aligners comprises sending all of the plurality of aligners from the fabrication site directly to the user at once.

\* \* \* \* \*